US008473057B2

(12) United States Patent
Donofrio et al.

(10) Patent No.: US 8,473,057 B2
(45) Date of Patent: *Jun. 25, 2013

(54) SHUNT-CURRENT REDUCTION HOUSING FOR AN IMPLANTABLE THERAPY SYSTEM

(75) Inventors: William T. Donofrio, Andover, MN (US); William J. Havel, Maple Grove, MN (US); Chris C. Christiansen, Oakdale, MN (US); Paul G. Krause, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 609 days.

This patent is subject to a terminal disclaimer.

(21) Appl. No.: 12/609,901

(22) Filed: Oct. 30, 2009

(65) Prior Publication Data
US 2010/0114205 A1     May 6, 2010

Related U.S. Application Data

(60) Provisional application No. 61/196,731, filed on Jan. 30, 2009, provisional application No. 61/110,275, filed on Oct. 31, 2008.

(51) Int. Cl.
*A61N 1/375* (2006.01)
(52) U.S. Cl.
USPC .......................................................... 607/36
(58) Field of Classification Search
USPC .............................................. 607/2, 4, 36, 60
See application file for complete search history.

(56) References Cited

U.S. PATENT DOCUMENTS

| 3,421,511 A | 1/1969 | Schwartz et al. |
| 3,522,811 A | 8/1970 | Seymour et al. |
| 3,593,718 A | 7/1971 | Krasner et al. |
| 3,645,267 A | 2/1972 | Hagfors |
| 3,650,277 A | 3/1972 | Sjostrand et al. |
| 3,796,221 A | 3/1974 | Hagfors |

(Continued)

FOREIGN PATENT DOCUMENTS

| EP | 0228539 B1 | 11/1990 |
| EP | 0688577 A1 | 12/1995 |

(Continued)

OTHER PUBLICATIONS

"Common-mode interference" Wikipedia reference retrieved on Aug. 25, 2008, 1 pg.

(Continued)

*Primary Examiner* — Carl H Layno
*Assistant Examiner* — Paula J Stice
(74) *Attorney, Agent, or Firm* — Carol F. Barry

(57) ABSTRACT

Techniques for minimizing interference between first and second medical devices of a therapy system may include providing an outer housing for at least one of the medical devices that comprises an electrically insulative layer formed over at least the electrically conductive portions (e.g., an electrically conductive layer) of the housing, or providing an electrically insulative pouch around an electrically conductive housing of at least the first medical device. The electrically insulative layer or electrically insulative pouch may reduce or even eliminate shunt-current that flows into the medical device via the housing. The shunt-current may be generated by the delivery of electrical stimulation by the second medical device. In some examples, the techniques may also include shunt-current mitigation circuitry that helps minimize or even eliminate shunt-current that feeds into the first medical device via one or more electrodes electrically connected to the first medical device.

32 Claims, 17 Drawing Sheets

U.S. PATENT DOCUMENTS

| | | | |
|---|---|---|---|
| 3,878,564 A | 4/1975 | Yao et al. | |
| 3,888,260 A | 6/1975 | Fischell | |
| 4,044,774 A | 8/1977 | Corbin et al. | |
| 4,146,029 A | 3/1979 | Ellinwood, Jr. | |
| 4,340,063 A | 7/1982 | Maurer | |
| 4,374,382 A | 2/1983 | Markowitz | |
| 4,428,378 A | 1/1984 | Anderson et al. | |
| 4,458,696 A | 7/1984 | Larimore | |
| 4,485,813 A | 12/1984 | Anderson et al. | |
| 4,535,774 A | 8/1985 | Olson | |
| 4,549,556 A | 10/1985 | Tarjan et al. | |
| 4,686,988 A | 8/1987 | Sholder | |
| 4,694,835 A | 9/1987 | Strand | |
| 4,745,923 A * | 5/1988 | Winstrom | 607/9 |
| 4,750,495 A | 6/1988 | Moore et al. | |
| 4,787,389 A | 11/1988 | Tarjan | |
| 4,827,936 A | 5/1989 | Pless et al. | |
| 4,830,006 A | 5/1989 | Haluska et al. | |
| 4,880,005 A | 11/1989 | Pless et al. | |
| 4,903,701 A | 2/1990 | Moore et al. | |
| 4,998,974 A | 3/1991 | Aker | |
| 5,031,618 A | 7/1991 | Mullett | |
| 5,058,584 A | 10/1991 | Bourgeois | |
| 5,111,816 A | 5/1992 | Pless et al. | |
| 5,117,824 A | 6/1992 | Keimel et al. | |
| 5,135,004 A | 8/1992 | Adams et al. | |
| 5,149,713 A | 9/1992 | Bousquet | |
| 5,199,428 A | 4/1993 | Obel et al. | |
| 5,203,326 A | 4/1993 | Collins | |
| 5,213,098 A | 5/1993 | Bennett et al. | |
| 5,220,917 A | 6/1993 | Cammilli et al. | |
| 5,220,929 A | 6/1993 | Marquit | |
| 5,243,980 A | 9/1993 | Mehra | |
| 5,251,621 A | 10/1993 | Collins | |
| 5,255,691 A | 10/1993 | Otten | |
| 5,261,400 A | 11/1993 | Bardy | |
| 5,292,336 A | 3/1994 | Spence, Jr. et al. | |
| 5,292,338 A | 3/1994 | Bardy | |
| 5,330,505 A | 7/1994 | Cohen | |
| 5,330,507 A | 7/1994 | Schwartz | |
| 5,330,515 A | 7/1994 | Rutecki et al. | |
| 5,331,966 A | 7/1994 | Bennett et al. | |
| 5,334,221 A | 8/1994 | Bardy | |
| 5,342,409 A | 8/1994 | Mullett | |
| 5,345,376 A | 9/1994 | Nourbakhsh | |
| 5,360,441 A | 11/1994 | Otten | |
| 5,464,434 A | 11/1995 | Alt | |
| 5,496,363 A | 3/1996 | Burgio et al. | |
| 5,545,186 A | 8/1996 | Olson et al. | |
| 5,564,434 A | 10/1996 | Halperin et al. | |
| 5,607,418 A | 3/1997 | Arzbaecher | |
| 5,638,832 A | 6/1997 | Singer et al. | |
| 5,651,378 A | 7/1997 | Matheny et al. | |
| 5,690,681 A | 11/1997 | Geddes et al. | |
| 5,700,282 A | 12/1997 | Zabara | |
| 5,702,429 A | 12/1997 | King | |
| 5,755,736 A | 5/1998 | Gillberg et al. | |
| 5,776,170 A | 7/1998 | MacDonald et al. | |
| 5,792,187 A | 8/1998 | Adams | |
| 5,807,234 A | 9/1998 | Bui et al. | |
| 5,817,131 A | 10/1998 | Elsberry et al. | |
| 5,824,021 A | 10/1998 | Rise | |
| 5,859,578 A | 1/1999 | Arnold | |
| 5,913,876 A | 6/1999 | Taylor et al. | |
| 6,006,134 A | 12/1999 | Hill et al. | |
| 6,058,331 A | 5/2000 | King | |
| 6,073,048 A | 6/2000 | Kieval et al. | |
| 6,134,470 A | 10/2000 | Hartlaub | |
| 6,141,586 A | 10/2000 | Mower | |
| 6,178,349 B1 | 1/2001 | Kieval | |
| 6,198,972 B1 | 3/2001 | Hartlaub et al. | |
| 6,272,377 B1 | 8/2001 | Sweeney et al. | |
| 6,308,101 B1 | 10/2001 | Faltys et al. | |
| 6,358,281 B1 | 3/2002 | Berrang et al. | |
| 6,438,420 B1 | 8/2002 | Thompson | |
| 6,473,644 B1 | 10/2002 | Terry, Jr. et al. | |
| 6,587,726 B2 | 7/2003 | Lurie et al. | |
| 6,713,671 B1 * | 3/2004 | Wang et al. | 174/391 |
| 6,788,974 B2 | 9/2004 | Bardy et al. | |
| 6,885,888 B2 | 4/2005 | Rezai | |
| 6,901,292 B2 | 5/2005 | Hrdlicka et al. | |
| 6,944,489 B2 | 9/2005 | Zeijlemaker et al. | |
| 7,010,345 B2 | 3/2006 | Hill et al. | |
| 7,212,864 B2 | 5/2007 | Wahlstrand et al. | |
| 7,218,964 B2 | 5/2007 | Hill et al. | |
| 7,242,982 B2 | 7/2007 | Singhal et al. | |
| 7,305,266 B1 * | 12/2007 | Kroll | 607/28 |
| 7,369,898 B1 | 5/2008 | Kroll et al. | |
| 2001/0001126 A1 | 5/2001 | Cammilli et al. | |
| 2002/0042634 A1 | 4/2002 | Bardy et al. | |
| 2002/0068958 A1 | 6/2002 | Bardy et al. | |
| 2002/0107546 A1 | 8/2002 | Ostroff et al. | |
| 2002/0107553 A1 | 8/2002 | Hill et al. | |
| 2002/0161402 A1 | 10/2002 | Vogel et al. | |
| 2003/0120320 A1 | 6/2003 | Solom | |
| 2005/0017054 A1 | 1/2005 | Iverson et al. | |
| 2005/0267543 A1 | 12/2005 | Heruth et al. | |
| 2005/0288743 A1 | 12/2005 | Ahn et al. | |
| 2006/0217792 A1 * | 9/2006 | Hussein et al. | 607/122 |
| 2007/0055308 A1 | 3/2007 | Haller et al. | |
| 2007/0255332 A1 | 11/2007 | Cabelka et al. | |
| 2008/0015659 A1 | 1/2008 | Zhang et al. | |
| 2009/0281623 A1 | 11/2009 | Kast et al. | |

FOREIGN PATENT DOCUMENTS

| | | |
|---|---|---|
| WO | 02083236 A2 | 10/2002 |
| WO | 03063946 A2 | 8/2003 |
| WO | 2004047295 A1 | 6/2004 |
| WO | 2007/127705 A1 | 11/2007 |
| WO | 2007/149757 A2 | 12/2007 |
| WO | 2008/111986 A1 | 9/2008 |

OTHER PUBLICATIONS

U.S. Appl. No. 12/551,331, filed Aug. 31, 2009.
U.S. Appl. No. 12/551,409, filed Aug. 31, 2009.
U.S. Appl. No. 12/551,377, filed Aug. 31, 2009.
Office Action from U.S. Appl. No. 12/551,409, dated Apr. 23, 2012, 7 pp.
Office Action from U.S. Appl. No. 12/551,377, dated Apr. 23, 2012, 8 pp.
Bilgutay et al, "Vagal Tuning—A New Concept in the Treatment of Supraventricular Arrhythmias, Angina Pectoris, and Heart Failure," *Journal of Thoracic Cardiovascular Surgery* 56(1): 71-82, Jul. 1968.
Braunwald et al., "Carotid Sinus Nerve Stimulation in the Treatment of Angina Pectoris and Supraventricular Tachycardia," *California Medicine* 112(3): 41-50, Mar. 1970.
Armour, "Instant to Instant Reflex Cardiac Regulation," Cardiology 61: 309-328, 1976.
Schwartz et al., "Effect of dorsal root section on the arrhythmias associated with coronary occlusion," *American Journal of Physiology* 231(3): 923-928, Sep. 1976.
Blair et al., "Responses of Thoracic Spinothalamic Neurons to Intracardiac Injection of Bradykinin in the Monkey," *Circulation Research* 51(1): 83-94, Jul. 1982.
Ammons et al., "Vagal Afferent Inhibition of Spinothalamic Cell Responses to Sympathetic Afferents and Bradykinin in the Monkey," *Circulation Research* 53(5): 603-612, Nov. 1983.
Blair et al., "Responses of Thoracic Spinothalamic and Spinoreticular Cells to Coronary Artery Occlusion," *Journal of Neurophysiology* 51(4): 636-648, Apr. 1984.
Ammons et al., "Effects of intracardiac bradykinin on $T_2$-$T_5$ medial spinothalamic cells," *American Journal of Physiology* 249: R147-R152, 1985.
Blair et al., "Activation of Feline Spinal Neurones by Potentiated Ventricular Contractions and Other Mechanical Cardiac Stimuli," *Journal of Physiology* 404: 649-667, 1988.
Schwartz et al., "Autonomic Mechanisms and Sudden Death—New Insights From Analysis of Baroreceptor Reflexes in Conscious Dogs With and Without a Myocardial Infarction," *Circulation* 78(4): 969-979, Oct. 1988.
Hobbs et al., "Cardiac and Abdominal Vagal Afferent Inhibition of Primate $T_9$-$S_1$ Spinothalamic Cells," *The American Physiological Society* 257: R889-R895, 1989.

Butler et al., "Cardiac Responses to Electrical Stimulation of Discrete Loci in Canine Atrial and Ventricular Ganglionated Plexi," *The American Physiological Society* 259: H1365-H1373, 1990.

Hull et al., "Heart Rate Variability Before and After Myocardial Infarction in Conscious Dogs at High and Low Risk of Sudden Death," *The American College of Cardiology* 16(4): 978-985, Oct. 1990.

Armour, "Intrinsic Cardiac Neurons," *Journal of Cardiovascular Electrophysiology* 2(4): 331-341, Aug. 1991.

Chandler et al., "Effects of Vagal Afferent Stimulation on Cervical Spinothalamic Tract Neurons in Monkeys," *Pain* 44: 81-87, 1991.

Linderoth et al., "Effects of Sympathectomy on Skin and Muscle Microcirculation During Dorsal Column Stimulation: Animal Studies," *Neurosurgery* 29(6): 874-879, 1991.

Vanoli et al., "Vagal Stimulation and Prevention of Sudden Death in Conscious Dogs With a Healed Myocardial Infarction," *Circulation Research* 68(5): 1471-1481, May 1991.

Cardinal et al., "Distinct Activation Patterns of Idioventricular Rhythms and Sympathetically-Induced Ventricular Tachycardias in Dogs With Atrioventricular Block," *PACE* 15: 1300-1316, Sep. 1992.

Fu et al., "Vagal Afferent Fibers Excite Upper Cervical Neurons and Inhibit Activity of Lumbar Spinal Cord Neurons in the Rat," *Pain* 51: 91-100, 1992.

Hobbs et al., "Evidence That $C_1$ and $C_2$ Propriospinal Neurons Mediate the Inhibitory Effects of Viscerosomatic Spinal Afferent Input on Primate Spinothalamic Tract Neurons," *Journal of Neurophysiology* 67(4): 852-860, Apr. 1992.

Hobbs et al., "Segmental Organization of Visceral and Somatic Input Onto $C_3$-$T_6$ Spinothalamic Tract Cells of the Monkey," *Journal of Neurophysiology* 68(5): 1575-1588, Nov. 1992.

Chandler et al., "A Mechanism of Cardiac Pain Suppression by Spinal Cord Stimulation: Implications for Patients With Angina Pectoris," *European Heart Journal* 14: 96-105, 1993.

Huang et al., "Effects of Transient Coronary Artery Occlusion on Canine Intrinsic Cardiac Neuronal Activity," *Integrative Physiological and Behavioral Science* 28(1): 5-21, Jan.-Mar. 1993.

Adamson et al., "Unexpected Interaction Between β-Adrenergic Blockade and Heart Rate Variability Before and After Myocardial Infarction—A Longitudinal Study in Dogs at High and Low Risk for Sudden Death," *Circulation* 90(2): 976-982, Aug. 1994.

Ardell, "Structure and Function of Mammalian Intrinsic Cardiac Neurons," *Neurocardiology*: 95-114, 1994.

Armour, "Peripheral Autonomic Neuronal Interactions in Cardiac Regulation," *Neurocardiology*: 219-244, 1994.

Foreman, "Spinal Cord Neuronal Regulation of the Cardiovascular System," *Neurocardiology*: 245-276, 1994.

Hull et al., "Exercise Training Confers Anticipatory Protection From Sudden Death During Acute Myocardial Ischemia," *Circulation* 89(2): 548-552, Feb. 1994.

Linderoth et al., "Sympathetic Mediation of Peripheral Vasodilation Induced by Spinal Cord Stimulation: Animal Studies of the Role of Cholinergic and Adrenergic Receptor Subtypes," *Neurosurgery* 35(4): 711-719, Oct. 1994.

Yuan et al., "Gross and Microscopic Anatomy of the Canine Intrinsic Cardiac Nervous System," *The Anatomical Record* 239: 75-87, 1994.

Armour, "Intrinsic Cardiac Neurons Involved in Cardiac Regulation Possess alpha$_1$, alpha$_2$, beta$_1$ and beta$_2$-Adrenoreceptors," *Can. J. Cardiol.* 13(3): 277-284, Mar. 1997.

Cardinal et al., "Reduced Capacity of Cardiac Efferent Sympathetic Neurons to Release Noradrenaline and Modify Cardiac Function in Tachycardia-Induced Canine Heart Failure," *Can. J. Physiol. Pharmacol.* 74: 1070-1078, 1996.

Chandler et al., "Vagal, Sympathetic and Somatic Sensory Inputs to Upper Cervical ($C_1$-$C_3$) Spinothalamic Tract Neurons in Monkeys," *Journal of Neurophysiology* 76(4): 2555-2567, 1996.

Zhang et al., "Thoracic Visceral Inputs Use Upper Cervical Segments to Inhibit Lumbar Spinal Neurons in Rats" *Brain Research* 709: 337-342, 1996.

Armour et al., "Gross and Microscopic Anatomy of the Human Intrinsic Cardiac Nervous System," *The Anatomical Record* 247: 289-298, 1997.

Croom et al., "Cutaneous Vasodilation During Dorsal Column Stimulation Is Mediated by Dorsal Roots and CGRP," *Am. J. Physiol.* 272 (*Heart Circ. Physiol.* 41): H950-H957, 1997.

Hautvast et al., "Spinal Cord Stimulation in Chronic Intractable Angina Pectoris: A Randomized, Controlled Efficacy Study," *American Heart Journal*, 136(6): 1114-1120, 1998.

Barron et al., "Spinal Integration of Antidromic Mediated Cutaneous Vasodilation During Dorsal Spinal Cord Stimulation in the Rat," *Neuroscience Letters* 260: 173-176, 1999.

Foreman, "Mechanisms of Cardiac Pain," *Annu. Rev. Physiol.* 61: 143-167, 1999.

Linderoth et al., "Physiology of Spinal Cord Stimulation: Review and Update," *Neuromodulation* 2(3):150-164, 1999.

Qin et al., "Chemical Activation of Cervical Cell Bodies: Effects on Responses to Colorectal Distension in Lumbosacral Spinal Cord of Rats," *J Neurophysiol* 82: 3423-3433, 1999.

Chandler et al., "Intrapericardiac Injections of Algogenic Chemicals Excite Primate $C_1$-$C_2$ Spinothalamic Tract Neurons," *Am J. Physiol. Regulatory Integrative Comp. Physiol.* 279: R560-568, 2000.

Foreman et al., "Modulation of Intrinsic Cardiac Neurons by Spinal Cord Stimulation: Implications for Its Therapeutic Use in Angina Pectoris," *Cardiovascular Research* 47: 367-375, 2000.

Hopkins et al., "Pathology of Intrinsic Cardiac Neurons From Ischemic Human Hearts," *The Anatomical Record* 259: 424-436, 2000.

Kember et al., "Aperiodic Stochastic Resonance in a Hysteretic Population of Cardiac Neurons," *The American Physical Society Physical Review E* 61(2): 1816-1824, Feb. 2000.

Meyerson et al., "Spinal Cord Stimulation," *Bonica's Management of Pain*: 1857-1876, 2001.

Ardell, "Neurohumoral Control of Cardiac Function," *Heart Physiology and Pathophysiology, Fourth Edition*: 45-49, 2001.

Farrell et al., "Angiotensin II Modulates Catecholamine Release Into Interstitial Fluid of Canine Myocardium In Vivo," *Am. J. Physiol. Heart Cir. Physiol.* 281: H813-822, 2001.

Kingma, Jr. et al., "Neuromodulation Therapy Does Not Influence Blood Flow Distribution or Left-Ventricular Dynamics During Acute Myocardial Ischemia," *Autonomic Neuroscience: Basic & Clinical* 91: 47-54, 2001.

Tanaka et al., "Low Intensity Spinal Cord Stimulation May Induce Cutaneous Vasodilation Via CGRP Release," *Brain Research* 896: 183-187, 2001.

Qin et al., "Responses and Afferent Pathways of Superficial and Deeper $C_1$ -$C_2$ Spinal Cells to Intrapericardial Algogenic Chemicals in Rats," *J. Neurophysiol* 85:1522-1532, 2001.

Armour et al., "Long-Term Modulation of the Intrinsic Cardiac Nervous System by Spinal Cord Neurons in Normal and Ischaemic Hearts," *Autonomic Neuroscience: Basic & Clinical* 95: 71-79, 2002.

Chandler et al., "Spinal Inhibitory Effects of Cardiopulmonary Afferent Inputs in Monkeys: Neuronal Processing in High Cervical Segments," *J. Neurophysiol* 87: 1290-1302, 2002.

Cardinal et al., "Spinal Cord Activation Differentially Modulates Ischaemic Electrical Responses to Different Stressors in Canine Ventricles," *Autonomic Neuroscience: Basic & Clinical* 111: 37-47, 2004.

Ardell, "Intrathoracic Neuronal Regulation of Cardiac Function," *Basic and Clinical Neurocardiology* 118-152, 2004.

Siddons et al., "Special Considerations: Pacing in Acute Myocardial Infarction," *Cardiac Pacemakers* Chapter 11: 200-217, 1967.

Bluemel et al., "Parasympathetic Postganglionic Pathways to the Sinoatrial Node," *American Journal of Physiology* 259 (*Heart Circ. Physiol.* 28): H1504-HI510, 1990.

Cooper et al, "Neural Effects on Sinus Rate and Atrioventricular Conduction Produced by Electrical Stimulation from a Transvenous Electrode Catheter in the Canine Right Pulmonary Artery," *Circulation Research* 46(1): 48-57, Jan. 1980.

Randall et al, "Functional Anatomy of the Cardiac Efferent Innervation," *Neurocardiology* Chapter 1: 3-24, 1988.

International Search Report and Written Opinion of international application No. PCT/US2009/062839, mailed Apr. 21, 2010, 18 pp.

Invitation to Pay Additional Fees and, Where Applicable, Protest Fee from international application No. PCT/US2009/062839, mailed Jan. 20, 2010, 5 pp.

Office Action for U.S. Appl. No. 12/551,331, dated Mar. 16, 2012, 12 pp.
Office Action from U.S. Appl. No. 12/551,331, dated Aug. 22, 2012, 15 pp.
Office Action from U.S. Appl. No. 12/551,409, dated Oct. 2, 2012, 5 pp.
Response to Office Action dated Aug. 22, 2012, from U.S. Appl. No. 12/551,331, filed Oct. 22, 2012, 14 pp.
Response to Office Action dated Apr. 23, 2012, from U.S. Appl. No. 12/551,377, filed Sep. 21, 2012, 13 pp.
Response to Office Action dated Apr. 23, 2012, from U.S. Appl. No. 12/551,409, filed Sep. 21, 2012, 22 pp.
Office Action from U.S. Appl. No. 12/551,377, dated Oct. 11, 2012, 5 pp.
Response to Final Office Action dated Aug. 22, 2012 and Advisory Action dated Nov. 2, 2012, from U.S. Appl. No. 12/551,331, filed Nov. 19, 2012, 13 pp.
International Preliminary Report on Patentability from international application No. PCT/US2009/062839, mailed May 12, 2011, 11 pp.
Response to Office Action dated Mar. 16, 2012, from U.S. Appl. No. 12/551,331, filed Jun. 18, 2012, 9 pp.
Response to Office Action dated Oct. 2, 2012, from U.S. Appl. No. 12/551,409, and Terminal Disclaimer filed Feb. 1, 2013, 23 pp.
Response to Office Action dated Oct. 11, 2012, from U.S. Appl. No. 12/551,377, and Terminal Disclaimer filed Jan. 11, 2013, 3 pp.

\* cited by examiner

SHUNT-CURRENT REDUCTION HOUSING FOR AN IMPLANTABLE THERAPY SYSTEM

This application claims the benefit of U.S. Provisional Application No. 61/196,731, entitled, "SHUNT-CURRENT REDUCTION HOUSING FOR AN IMPLANTABLE THERAPY SYSTEM," and filed on Jan. 30, 2009, and U.S. Provisional Application No. 61/110,275, entitled, "SHUNT-CURRENT REDUCTION TECHNIQUES FOR AN IMPLANTABLE THERAPY SYSTEM," and filed on Oct. 31, 2008, the entire contents of which are incorporated herein by reference.

TECHNICAL FIELD

The disclosure relates to therapy systems, and more particularly, therapy systems including at least two therapy delivery modules.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry.

For example, implantable cardiac devices, such as cardiac pacemakers or implantable cardioverter defibrillators, provide therapeutic stimulation to the heart by delivering electrical therapy signals such as pulses or shocks for pacing, cardioversion or defibrillation pulses via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver cardioversion or defibrillation therapy to a patient's heart upon detecting ventricular fibrillation. Some proposed medical device systems include a neurostimulator in addition to the implantable cardiac device.

SUMMARY

In general, the disclosure is directed to therapy systems that deliver electrical stimulation therapy to a tissue site within a patient and cardiac rhythm management therapy to a heart of a patient. In some examples, the therapy system may include a first medical device that delivers electrical stimulation to a tissue site within a patient, such as proximate a nerve (e.g., a vagus nerve or a spinal cord) and/or an extravascular tissue site, and a second medical device that delivers cardiac rhythm management therapy, such as at least one of pacing, cardioversion or defibrillation therapy to a heart of the patient. In some examples, the first medical device may be referred to as an implantable neurostimulator (INS) or an electrical stimulator, and the second medical device may be referred to as an implantable cardiac device (ICD) or an external defibrillator.

Described herein are techniques for minimizing interference between the first and second medical devices. In some examples, the delivery of electrical stimulation by the second medical device may cause electrical current generated by the electrical stimulation to pass through a conductive pathway including a housing (e.g., an electrically conductive portion of the housing) of the first medical device and, in some examples, electrodes connected to the first medical device. The current flows through the conductive pathway to the first medical device may be referred to as "shunt-current." In some examples, the first medical device comprises an outer housing comprising exposed (e.g., an external or outer surface) electrically conductive portions that are substantially fully covered by an electrically insulative material. For example, the electrically conductive portions of the first medical device may be defined by an electrically conductive layer, such as titanium or stainless steel. In addition to or instead of the electrically insulative material that substantially fully covers exposed electrically conductive portions of the outer housing of the first medical device, the housing may also comprise an electrically insulative layer that substantially fully covers an internal surface of the electrically conductive layer or other electrically conductive portions of the outer housing. The electrically insulative layer may reduce or eliminate the shunt-current through the housing of the first medical device.

In other examples, the first medical device may include an electrically insulative pouch that substantially fully encapsulates at least the electrically conductive portions of the housing and reduces or eliminates the shunt-current through the housing of the first medical device. In some examples, instead of or in addition to an electrically insulative pouch that substantially fully encapsulates at least the electrically conductive portions of the housing, the first medical device may include an electrically insulative pouch that encapsulates circuitry and wiring enclosed by the housing of the first medical device. In this way, the electrically insulative pouch may provide insulation between circuitry and wiring inside of the housing and the housing. Reducing or eliminating the shunt-current may help reduce the current at an interface between the housing of the first medical device and tissue of the patient, may increase the current provided by the second medical device to the desired therapy site, e.g., may increase the defibrillation current provided by the second medical device to a patient's heart, or both. In addition, reducing the shunt-current may help limit the passage of undesirable currents to therapy components within a housing of the first medical device.

In some examples, the first medical device also may include shunt-current mitigation circuitry, which may reduce or eliminate shunt-current from passing through a conductive pathway including electrodes connected to the first medical device. Reducing the shunt-current in this manner may reduce the current at an interface between the electrodes connected to the first medical device and the tissue of the patient, may increase the current provided by the second medical device to the desired therapy site, or both. Additionally, reducing the shunt-current in this manner may help reduce or eliminate passage of undesirable currents to therapy components within the housing of the first medical device. In some examples, the first medical device may include both a housing comprising an electrically insulative layer and shunt-current mitigation circuitry, which together may substantially reduce or eliminate shunt-current from passing through a conductive pathway including electrodes connected to the first medical device or a housing of the first medical device.

In one aspect, the disclosure is directed to a system comprising a first implantable medical device (IMD) that delivers electrical stimulation to a first tissue site within a patient, and a second IMD that delivers electrical stimulation to a second tissue site within the patient. According to this aspect of the disclosure, the first IMD comprises an outer housing that comprises an electrically conductive layer including an internal surface and an external surface. The housing may further comprise an electrically insulative layer substantially fully covering at least one of the internal surface or the external surface of the electrically conductive layer. The electrically insulative layer is configured to mitigate shunt-current flowing through the outer housing of the first IMD.

In another aspect, the disclosure is directed to a system comprising a first IMD that delivers electrical stimulation to a first tissue site within a patient, and a second IMD that delivers electrical stimulation to a second tissue site within the patient. According to this aspect of the disclosure, the first IMD comprises an outer housing and an electrically insulative pouch substantially fully encapsulating at least the electrically conductive portions of the housing. In some examples, the electrically insulative pouch substantially fully encapsulates the entire housing. The electrically insulative pouch is configured to reduce shunt current to the electrically conductive layer.

In a further aspect, the disclosure is directed to a method of reducing shunt-current between a first IMD and a second IMD. According to this aspect of the disclosure, the method comprises substantially fully covering at least one of an internal surface or an external surface of an electrically conductive layer of a housing of the first IMD with at least one of an electrically insulative layer or an electrically insulative pouch.

In another aspect, the disclosure is directed to a method comprising implanting in a body of a patient a first IMD that delivers electrical stimulation to a first tissue site within the patient, and implanting in the body of the patient a second IMD that delivers electrical stimulation to a second tissue site within the patient. According to this aspect of the disclosure, the first IMD may comprise a housing, and the housing comprises an electrically conductive layer including an internal surface and an external surface. The housing may further include an electrically insulative layer substantially fully covering at least one of the internal surface or the external surface of the electrically conductive layer.

In another aspect, the disclosure is directed to a computer-readable medium comprising instructions that cause a programmable processor to perform any part of the techniques described herein.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
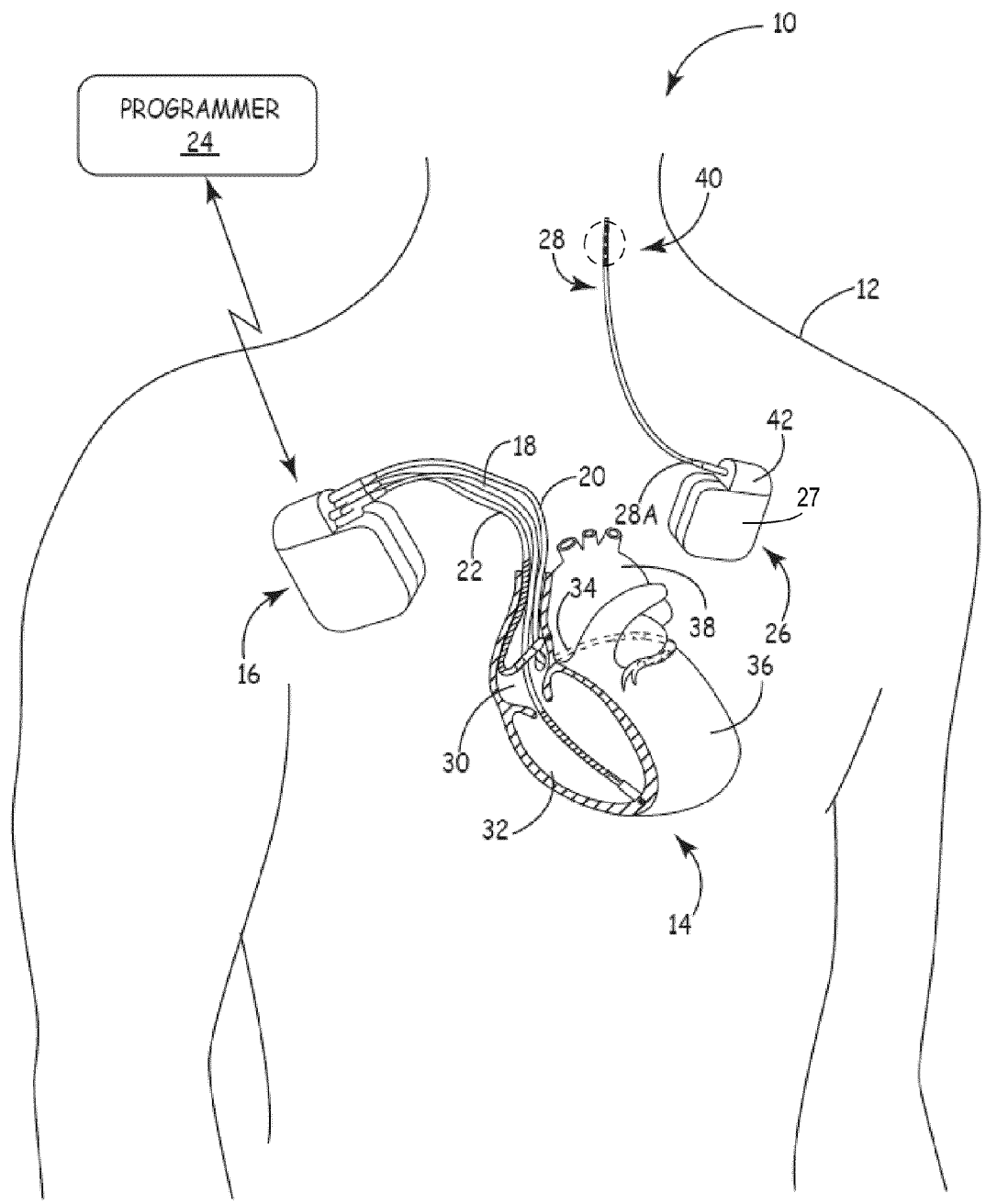
FIG. 1 is a conceptual diagram illustrating an example therapy system including an implantable cardiac device (ICD) and an implantable neurostimulator (INS).

Described herein are techniques for minimizing interference between first and second medical devices. The first and second medical devices may be enclosed in physically separate housings (e.g., as part of different medical devices) that may be separately implantable within a patient. As described with respect to FIG. 1, in some examples, the first medical device may comprise an implantable electrical stimulator that generates and delivers electrical stimulation therapy to a tissue site, which may be a nonmyocardial tissue site (e.g., tissue proximate a nerve) or a nonvascular cardiac tissue site (e.g., a cardiac fat pad). The second medical device may comprise a cardiac rhythm management device that provides at least one of pacing, cardioversion or defibrillation therapy to the heart of the patient. In some examples, the second medical device may be an implantable device (referred to herein as an implantable cardiac device (ICD)) or an external device that delivers at least one of pacing, cardioversion or defibrillation therapy to the heart of the patient via one or more external electrodes (e.g., electrodes located on the outer surface of the patient's skin) For example, the second medical device may comprise an automated external defibrillator (AED) or another type of external defibrillator. In some examples, the second medical device may also sense electrical cardiac signals of the heart of the patient.

In some examples, the techniques described herein may also minimize interference between the first medical device and other external current sources, such as an electrocautery device, a radiofrequency (RF) cautery device, another device that produces electromagnetic interference, or a magnetic resonance imaging (MRI) modality or radiotherapy scanner, which may induce currents in conductive material forming or connected to the first medical device. In examples in which the second medical device is configured to deliver a defibrillation shock to a patient, the techniques described herein may also facilitate faster recovery of the first medical device to normal function after delivery of a defibrillation shock by the second medical device.

The second medical device may generate and deliver a stimulation signal to tissue of the patient as part of the pacing, cardioversion or defibrillation therapy. In some examples, the delivery of the stimulation signal to tissue may result in undesired electrical current that flows through electrically conductive portions of the outer housing of the first medical device or implanted electrodes that are electrically connected to the first medical device. The electrical current may flow through an electrical path including the electrically conductive portions of the outer housing of the first medical device or the electrodes connected to the first medical device and into the housing of the first medical device. The current that flows into the first medical device as a result of the delivery of stimulation by the second medical device, or vice-versa, may be referred to as "shunt-current." Shunt-current may have adverse effects on the components of the current-receiving medical device. For example, the shunt-current may stress components within the first medical device, such as stimulation generation circuitry or sensing circuitry.

In some examples, the therapy delivery by the second medical device may be efficacious despite the flow of shunt-current to the first medical device. However, reducing the amount of shunt-current at the first medical device may increase the therapeutic efficacy of therapy delivery by the second medical device by increasing the intensity of stimulation delivered to patient 12. The intensity of stimulation may be a function of one or more parameters of the electrical stimulation signal, such as the current or voltage amplitude.

In addition, the shunt-current may have undesirable physiological effects on tissue of the patient through which the shunt-current flows. For example, the current that flows from the stimulation electrodes connected to the second medical device and into the first medical device through tissue of the patient may unintentionally stimulate tissue adjacent to the housing of the first medical device or tissue adjacent to the electrodes connected to the first medical device, depending on the conductive pathway through which the shunt-current flows. In some cases, the flow of the shunt-current through the housing of the first medical device or the electrodes connected to the first medical device may result in a concentration of the current in a relatively small area, which may unintentionally stimulate or stress the tissue. This may result in undesired physiological responses, such as interfering with stimulation provided by the first medical device.

Various techniques are described herein to reduce or eliminate a shunt-current that is introduced into a first medical device, where the shunt-current is at least partially attributable to the delivery of stimulation by a second medical device different than the first medical device. In accordance with some examples of the devices, systems, and techniques described herein, the shunt-current may be minimized without adversely affecting the intensity of stimulation delivered by the second medical device.

While techniques for reducing the shunt-current in therapy systems including physically separate implantable medical devices are primarily described herein, the techniques described herein are also applicable to a therapy system comprising at least one external medical device, such as an AED or another external defibrillator. The external medical device may generate the shunt-current. In addition, the techniques described herein, such as the use of an insulative coating or an insulative pouch that substantially fully encapsulates exposed (e.g., exposed to tissue when the medical device is implanted in a patient) electrically conductive portions of an outer housing or internal circuitry of an implantable medical device, may also be used in therapy systems that include a single medical device. The insulative coating or pouch may be comprised of an electrically insulative material or an electrically nonconductive material, such as a dielectric material. The delivery of stimulation by the single medical device may also generate shunt-current that may be introduced into the same medical device. Thus, the techniques described herein may also be used to reduce or eliminate a shunt-current that is introduced into the same medical device that generates the stimulation current providing the source for the shunt-current.

FIG. 1 is a conceptual diagram illustrating an example therapy system 10 that may be used to provide therapy to patient 12. Patient 12 ordinarily, but not necessarily, will be a human. Therapy system 10 includes ICD 16, which is connected to leads 18, 20, and 22, and programmer 24. ICD 16 may be, for example, a device that provides cardiac rhythm management therapy to heart 14, and may include, for example, an implantable pacemaker, cardioverter, and/or defibrillator that generates and delivers therapy to heart 14 of patient 12 via electrodes coupled to one or more of leads 18, 20, and 22. In some examples, ICD 16 may deliver pacing pulses, but not cardioversion or defibrillation pulses, while in other examples, ICD 16 may deliver cardioversion or defibrillation pulses, but not pacing pulses. In addition, in further examples, ICD 16 may deliver pacing, cardioversion, and defibrillation pulses. Pacing therapy delivered by ICD 16 may include any suitable type of pacing, such as cardiac resynchronization therapy.

Therapy system 10 further comprises implantable electrical stimulator 26, which is coupled to lead 28. Electrical stimulator 26 may also be referred to as an implantable neurostimulator (INS) 26, although INS 26 is also configured to deliver stimulation to tissue sites other than neural tissue. INS 26 may be any suitable implantable medical device (IMD) that includes a signal generator that generates electrical stimulation signals that may be delivered to a tissue site of patient 12, e.g., tissue proximate a vagus nerve, a spinal cord or heart 14 of patient 12. As previously indicated, in some examples, the tissue site may include at least one of a nonmyocardial tissue site or a nonvascular cardiac tissue site. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. The nonmyocardial tissue site may include extravascular tissue sites or intravascular tissue sites.

In the example shown in FIG. 1, electrodes of lead 28 are position to deliver electrical stimulation to target tissue site 40 proximate a vagus nerve of patient 12. The vagus nerve is primarily referred to herein as the target nerve for neurostimulation therapy. In some examples, the vagus nerve may be stimulated transvenously, e.g., via a stimulation lead located in a vein or artery. In other examples, the vagus nerve may be stimulated non-transvenously, e.g., via a stimulation lead located outside a vein or artery. However, in other examples, the target nerve may be other nerves within patient 12, such as nerves branching from the spinal cord, the vagus nerve, and the like.

In some examples, delivery of electrical stimulation to a tissue site proximate a nerve or a nonmyocardial tissue site that may not be proximate a nerve may help modulate an autonomic nervous system of patient 12. In some examples, INS 26 may deliver electrical stimulation therapy to a nerve of patient 12 via a lead implanted within vasculature (e.g., a blood vessel) of patient 12. In some examples, INS 26 may deliver electrical stimulation that is delivered to peripheral nerves that innervate heart 14, or fat pads on heart 14 that may contain nerve bundles. In the example shown in FIG. 1, electrodes of lead 28 are positioned outside the vasculature of patient 12 and positioned to deliver electrical stimulation to a vagus nerve (not shown) of patient 12. Stimulation may be delivered to extravascular tissue sites, for example, when lead 28 is not implanted within vasculature, such as within a vein, artery or heart 14. In other examples, stimulation may be delivered to a nonmyocardial tissue site via electrodes of an intravascular lead that is implanted within vasculature.

In the example shown in FIG. 1, the components of ICD 16 and INS 26 are enclosed in separate housings, such that ICD 16 and INS 26 are physically separate devices. For example, as shown in FIG. 1, INS 26 includes outer housing 27 that substantially encloses its components and a connector block 42 to which lead 28 mechanically connects to INS 26. In addition, connector block 42 includes electrical connectors with which conductors of lead 28 electrically couple to components of INS 26 enclosed in outer housing 27. In some examples, housing 27 may hermetically seal the components of INS 26 from exposure to an external environment, such as tissue or bodily fluids of patient 12. Both ICD 16 and INS 26 may comprise hermetically sealed housings that substantially enclose functional components of the respective device 16, 26, such as sensing circuitry and stimulation circuitry. The components of ICD 16 and INS 26 are described below with reference to FIGS. 6 and 7, respectively.

In some examples, at least a portion of housing 27 may be formed of a metal, such as, for example, titanium, stainless steel, or the like. Housing 27 may include electrically conductive portions, which may result in shunt-current flowing from electrodes carried by leads 18, 20, 22 connected to ICD 16 to housing 27 of INS 26 during therapy delivery by ICD 16. In some examples, the entire outer housing 27 may be electrically conductive. As described above, this shunt-current may result in undesirable physiological effects to patient 12, including, for example, unintended stimulation of tissue adjacent to housing 27. In some examples, the shunt-current may also interfere with operation of components of INS 26, including, for example, sensing circuitry or stimulation circuitry, may reduce the current provided by the electrodes carried by leads 18, 20, 22 to the desired therapy site, or both.

The shunt-current may flow into the sensing or stimulation circuitry of INS 26 through an electrical path that includes one or more electrodes carried by lead 28 or through an electrical path that includes electrically conductive portions of housing 27. In some examples, the sensing or stimulation circuitry may be directly electrically connected to housing 27 by a wire or an electronic component. In other examples, the sensing or stimulation circuitry may be electrically coupled to housing 27 by means of capacitive coupling via electrical feedthroughs connected to housing 27. In some examples, the sensing or stimulation circuitry may be electrically coupled to housing 27 due to the close proximity between the circuitry and housing 27. In any of these examples, it may be desirable to provide electrical insulation between housing 27 and the circuitry to reduce or substantially eliminate any shunt-current from flowing into the circuitry through an electrical path including housing 27.

INS 26 may include features that mitigate or substantially eliminate shunt-current from flowing from electrodes carried by leads 18, 20, 22 connected to ICD 16 to housing 27. For example, INS 26 may include a housing 27 that comprises a plurality of layers, at least one of which is nonconductive, i.e., electrically insulative. As another example, INS 26 may include an electrically insulative pouch that substantially fully encapsulates housing 27, fully encapsulates at least the electrically conductive portions of outer housing 27 that interface with tissue of patient 12 when INS 26 is implanted within patient 12, or substantially fully encapsulates circuitry or wiring inside of housing 27. In either case, housing 27 may include a conductive layer, which may include, for example, a biocompatible metal such as titanium or stainless steel. The conductive layer may be a part of the structure that defines outer housing 27.

In the example depicted in FIG. 1, the electrically insulative layer or electrically insulative pouch is described as substantially fully covering or substantially fully encapsulating housing 27, which does not include connector block 42. However, in other examples, the electrically insulative layer or electrically insulative pouch may at least partially cover or encapsulate connector block 42, in addition to substantially fully encapsulating housing 27. In some examples, the electrically insulative layer or electrically insulative pouch may substantially fully cover connector block 42 in addition to substantially fully encapsulating housing 27. In some examples, the electrically insulative layer or electrically insulative pouch may substantially fully encapsulate or substantially fully cover any electrically conductive portions (e.g. outer or inner surfaces) of housing 27 and/or connector block 42.

As used herein, the terms "substantially fully encapsulating" and "substantially fully covering" may be used to refer to a layer or pouch that fully encapsulates or covers housing 27, while also including a layer or pouch that defines at least one aperture that facilitates connection of conductors in lead 28 to components within housing 27, either directly or indirectly. For example, an electrically insulative layer or pouch may substantially fully cover housing 27 and may not fully encapsulate connector block 42, and the electrically insulative layer or pouch may define an aperture that allows conductors extending from connector block 42 to pass through an aperture or feedthrough in housing 27 and couple to components therein. As another example, an electrically insulative layer or pouch may substantially fully cover both housing 27 and connector block 42, and may define an aperture that allows at least one conductor within lead 28 to pass through and couple to a conductor within connector block 42.

The conductive layer of housing 27 may define an external surface (e.g., a surface that faces tissue when INS 26 is implanted within patient) and an internal surface. The internal surface may be a surface that is substantially opposite the tissue-facing surface. The internal surface may face components of INS 26, such as a stimulation generator (e.g., as described with respect to FIG. 7). In some examples, the electrically insulative layer may substantially fully cover or encapsulate the external surface of the conductive layer of housing 27, may substantially fully cover or line the internal surface of the conductive layer, or both. Substantially fully covering an external surface, internal surface, or both of the conductive layer may more effectively mitigate or substantially eliminate shunt-current from interfering with operation of INS 26 than partially covering a surface of the conductive layer. For example, in cases in which outer housing 27 of INS 26 does not include an electrically insulative layer that fully encapsulates or lines a surface of an electrically conductive layer, the shunt-current may result in unintentional stimulation of tissue of patient 12, may interfere with operation of INS 26, or may reduce the current provided by the electrodes carried by leads 18, 20, 22 to the desired therapy site. As described above, the electrically insulative layer may define at least one aperture that permits one or more conductors to pass through from connector block 42 to components within housing 27. However, despite defining an aperture, the electrically insulative layer may not expose any electrically conductive portions of outer housing 27 of INS 26.

Even in cases in which housing 27 includes an electrically conductive layer and an electrically insulative layer that partially encapsulates or lines the electrically conductive layer, the shunt-current may interfere with operation of INS 26 as a conductive path remains from electrodes carried by leads 18, 20, 22 to housing 27 and components of INS 26 within housing 27. A medical device housing that includes a conductive layer and an electrically insulative layer that partially, but not fully, encapsulates the conductive layer may increase the current of the shunt-current at the interface of the conductive layer and tissue of patient 12. This increased current may result in undesired stimulation to the tissue adjacent to the conductive layer. Hence, an electrically insulative layer that substantially fully encapsulates an external surface of the electrically conductive layer (or electrically conductive portions) of housing 27, substantially fully lines an internal surface of the electrically conductive layer of housing 27, or both, may more effectively mitigate or substantially eliminate shunt-current from undesirably affecting operation of INS 26 or tissue of patient 12 adjacent to housing 27.

In some examples, the electrically insulative layer of housing 27 may include an electrically insulative metal oxide, an electrically insulative metal nitride, an electrically insulative ceramic, or an electrically insulative sintered material. For example, the electrically insulative layer of housing 27 may include aluminum oxide ($Al_2O_3$), silicon dioxide ($SiO_2$), silicon nitride ($Si_3N_4$), aluminum nitride (AlN), glass, porcelain, diamond, or titanium dioxide ($TiO_2$). In some examples, the electrically insulative layer may be formed by oxidation of the material from which the conductive layer of housing 27 is formed (e.g., oxidation of titanium to form titanium dioxide). In other examples, the electrically insulative layer may be formed on or otherwise deposited on the conductive layer by ion-beam deposition, sputtering, or another atomic or molecular treatment.

As another example, the electrically insulative layer may include an electrically insulative plastic or polymer. The electrically insulative plastic or polymeric may include, for example, silicone, polyethylene, cross-linked polyethylene, polyvinylchloride (PVC), rubber-like polymers, parylene, polyimide, epoxy, polytetrafluoroethylene (PTFE), ethylene tetrafluoroehtylene (ETFE), polyurethane, a liquid crystal polymer (LCP), polycarbonate, a biocompatible thermoplastic, or the like. One example of a suitable silicone is available under the trade designation Silastic® Medical Adhesive Silicone, Type A, from Dow Corning, Midland, Mich. An example of a suitable polycarbonate is available under the trade designation Lexan HPM, from SABIC Innovative Plastics, Pittsfield, Mass. An example of a biocompatible thermoplastic is available under the trade designation PEEK-OPTIMA® from Invibio, Inc., West Conshohocken, Pa. In some examples, the electrically insulative plastic or polymer may be applied to the conductive layer of housing 27 by dip coating, molding, a laser treatment, an etching treatment, spraying, or the like.

In some examples, housing 27 may comprise more than two layers. For example, housing 27 may comprise an electrically conductive layer, a second layer formed over an internal surface or external surface of the electrically conductive layer, and a third layer formed over the second layer. In some examples, the second and third layers may comprise a respective one of the electrically insulative layers described above. For example, the second layer may comprise an electrically insulative metal oxide, an electrically insulative metal nitride, an electrically insulative ceramic, or an electrically insulative sintered material, and the third layer may comprise an electrically insulative plastic or polymer. In other examples, the second layer may comprise a first electrically insulative metal oxide, electrically insulative metal nitride, electrically insulative ceramic, or electrically insulative sintered material, and the third layer may comprise a second electrically insulative metal oxide, electrically insulative metal nitride, electrically insulative ceramic, or electrically insulative sintered material.

In some examples, the second layer may comprise an electrically insulative material, while the third layer comprises a material that provides another type of protection to the components of INS 26 or housing 27, such as, for example, chemical protection, physical protection, or the like. In other examples, the second layer may comprise a material that provides chemical protection, physical protection, or the like to components of INS 26 or housing 27, and the third layer may comprise an electrically insulative material. In some examples, the second layer or third layer may be metallic, and may comprise, for example, a metal coating, a metal film, metal stamping, metal enclosure, or metal shield.

Housing 27 may comprise one or more additional layers, which may be formed over the third layer. Each of the additional layers may comprise the same material as one of the second and third layers, or may comprise a different material. In some examples, one or more of the additional layers may provide physical protection to the other layers of housing 27. One or more of the additional layers also may, but need not, electrically insulate the other layers of housing 27.

In some examples, outer housing 27 of INS 26 may comprise one or more layers substantially fully covering an external surface of the electrically conductive layer and one or more layers substantially fully covering an internal surface of the electrically conductive layer. For example, housing 27 may comprise a first electrically insulative layer that substantially fully covers the external surface of the electrically conductive layer and a second electrically insulative layer that substantially fully covers the internal surface of the electrically conductive layer. In some examples, the first and second electrically insulative layers may comprise the same material, while in other examples, the first and second electrically insulative layers may comprise different materials. Further, housing 27 may include additional layers formed over one or both of the first and second electrically insulative layers.

In some examples, outer housing 27 of INS 26 may include an electrically insulative spacer between two adjacent layers, e.g., an inner layer and an outer layer. The inner layer may be a layer that is disposed closer to an interior of housing 27, in which components of INS 26 are housed, than the outer layer, while the outer layer may be a layer that is disposed closer to an exterior of housing 27 than the inner layer. The exterior layer may face tissue of patient 12 when INS 26 is implanted within patient 12. The electrically insulative spacer may be disposed between any two adjacent layers, and may electrically insulate the inner layer from the outer layer. For example, housing 27 may comprise an electrically conductive inner layer and a metallic outer layer (e.g., facing tissue of patient 12 when INS 26 is implanted within patient 12), which also may be electrically conductive. In examples such as these, housing 27 may comprise an electrically insulative spacer between the electrically conductive inner layer and the metallic outer layer. In some examples, the electrically insulative spacer may comprise a sleeve or other preformed object that fits around the electrically conductive inner layer, e.g., into which the electrically conductive inner layer is fitted. The electrically insulative spacer then may be attached to the inner layer by any suitable technique, such as, for example, an adhesive or a heat treatment. The outer layer then may be deposited over the insulative spacer.

In other examples, the electrically insulative spacer layer may be deposited over the electrically conductive inner layer by ion-beam deposition, sputtering, another atomic or molecular treatment, molding, dip coating, or the like. The electrically insulative spacer layer may comprise, for example, a polymer, plastic, electrically insulative metal oxide, electrically insulative metal nitride, electrically insulative ceramic, or electrically insulative sintered material, including any materials described above.

In some examples, instead of or in addition to a housing 27 comprising an electrically insulative layer or an electrically insulative spacer, INS 26 may comprise an electrically insulative pouch that substantially fully encapsulates housing 27 or at least the electrically conductive portions of outer housing 27. Similar to a housing 27 that includes an electrically insulative layer, the electrically insulative pouch may mitigate or substantially eliminate shunt-current from flowing from electrodes carried by leads 18, 20, 22 connected to ICD 16 to housing 27 of INS 26.

The electrically insulative pouch may comprise, for example, a preformed covering into which housing 27 of INS 26 fits. The electrically insulative pouch may be physically separate from housing 27 and positioned around housing 27. In some examples, the electrically insulative pouch may comprise a size and/or shape that substantially conforms to the size and/or shape of housing 27, so that the pouch forms an intimate fit with housing 27. For example, the preformed electrically insulative pouch may be sized and/or shaped to form a friction fit or otherwise engage with one or more surfaces of housing 27. In other examples, the preformed electrically insulative pouch may comprise a size and/or shape that does not substantially conform to the size and/or shape of housing 27. For example, the electrically insulative pouch may be sized larger than housing 27, so that there is not a friction fit between the pouch and housing 27, and the pouch fits more loosely around housing 27. The preformed electrically insulative pouch may be substantially flexible (e.g., substantially non-self supporting) or substantially rigid (e.g., substantially self supporting).

In any case, the electrically insulative pouch may substantially fully enclose or encapsulate housing 27 or at least the electrically conductive portions of housing 27, and may not encapsulate connector block 42. In some examples, the electrically insulative pouch may at least partially encapsulate connector block 42, in addition to substantially fully encapsulating housing 27. In other examples, the electrically insulative pouch may substantially fully encapsulate connector block 42 in addition to substantially fully encapsulating housing 27. The electrically insulative pouch may define an aperture that allows conductors extending from connector block 42 to pass through an aperture or feedthrough in housing 27 and electrically couple to components therein. As another example, the electrically insulative pouch may substantially fully cover both housing 27 and connector block 42, and may define an aperture which allows at least one conductor within lead 28 to pass through and couple to a conductor within connector block 42.

In this way, the electrically insulative pouch may mitigate or substantially prevent shunt-current from traveling from electrodes carried by leads 18, 20, 22 connected to ICD 16 to housing 27 of INS 26. In some examples, the insulative pouch may comprise a single piece of material, which comprises a slot or other opening into which the housing 27 is placed. The slot or other opening may then be closed using an adhesive, solvent welding, ultrasonic welding, thermal welding or any other suitable technique to form a continuous, unitary enclosure around housing 27. In some examples, the insulative pouch may be coupled or attached to housing 27 in one or more location to reduce or eliminate relative motion between housing 27 and the insulative pouch. The insulative pouch may be coupled or attached to housing 27 by an adhesive, such as a silicone or epoxy adhesive.

In other examples, the electrically insulative pouch may comprise two or more pieces of material that are arranged around at least the electrically conductive portions of outer housing 27 or the entire outer housing 27 and then coupled to each other and, optionally, to housing 27. For example, the electrically insulative pouch may comprise a first portion and a second portion. The first and second portions may be placed, for example, on a first side and a second side of housing 27 (the first and second sides may or may not be opposite each other). The first and second portions of the electrically insulative pouch may be coupled or attached to the first and second sides of housing 27, respectively, using an adhesive or another suitable technique. The first and second pieces of the electrically insulative pouch then may be coupled to each other using an adhesive, solvent welding, thermal welding, ultrasonic welding, or another suitable process.

The electrically insulative pouch may comprise, for example, a biocompatible polymer or plastic. In some examples, the electrically insulative pouch may comprise at least one of silicone, polyethylene, cross-linked polyethylene, parylene, polyimide, epoxy, polyurethane, polyvinylchloride (PVC), rubber-like polymers, polytetrafluoroethylene (PTFE), ethylene tetrafluoroehtylene (ETFE), polycarbonate, a biocompatible thermoplastic, or the like. The electrically insulative pouch may comprise a thickness of about 25.4 micrometers (about 0.001 inches) to a thickness of about 1016 micrometers (about 0.040 inches), or about 254 micrometers (about 0.01 inches) to a thickness of about 508 micrometers (about 0.02 inches).

The electrically insulative pouch may be assembled around housing 27 by a manufacturer of INS 26 at the time of manufacture or prior to shipping INS 26 to a wholesaler or the implanting clinician. In other examples, the electrically insulative pouch may be assembled with housing 27 by the implanting clinician at or before the time at which INS 26 is implanted in patient 12. In some examples, the implanting clinician may determine whether an electrically insulative pouch around housing 27 of INS 26 may be useful for the particular therapy system implanted within patient 12 at or before the time of implant. Accordingly, the clinician may or may not assemble the pouch around housing 27 depending on his or her determination at or near the time of implant within a particular patient 12. For example, the implanting clinician may consider the implant location of INS 26, ICD 16, and any leads coupled to INS 26 or ICD 16 when determining whether INS 26 would benefit from an electrically insulative pouch. When the implanting clinician determines that INS 26 would benefit from an electrically insulative pouch, the clinician may assemble the electrically insulative pouch around housing 27 of INS 26.

In some examples, the electrically insulative pouch is disposed inside of housing 27 and substantially fully encapsulates components housed in housing 27, such as, for example, electrical circuitry and/or wiring. In some cases, the electrical circuitry and/or wiring may not be electrically connected to housing 27, and the electrically insulative pouch may provide electrical insulation of the circuitry and/or wiring from housing 27. In this way, the electrically insulative pouch may eliminate any direct electrical connection between the circuitry and or/wiring and housing 27, and may reduce any capacitive or inductive electrical coupling between the circuitry and wiring and housing 27. In some examples, INS 26 includes an electrically insulative layer or electrically insulative pouch that substantially fully covers or encapsulates an outer surface of housing 27 in addition to an electrically insulative pouch that encapsulates components housed in housing 27. In other example, INS 26 may not include an electrically insulative layer or electrically insulative pouch that substantially fully covers or encapsulates an outer surface of housing 27 in addition to an electrically insulative pouch that encapsulates components housed in housing 27.

In some examples, INS 26 may include a conformal coating or encapsulant over components such as circuitry and/or wiring enclosed within housing 27, such that the coating or encapsulant is positioned between the operative components of housing 27 (e.g., stimulation or sensing circuitry) and the electrically conductive portions of outer housing 27. For example, the circuitry and/or wiring may be coated or encapsulated with a polymer such as parylene, silicone, or epoxy. The encapsulant or coating may provide an electrically insulative barrier between housing 27 and the circuitry and/or wiring. In some examples, INS 26 may include an electrically insulative layer or electrically insulative pouch that substantially fully covers or encapsulates an outer surface of housing 27 in addition to a conformal coating or encapsulant that encapsulates components housed in housing 27. In other example, INS 26 may not include an electrically insulative layer or electrically insulative pouch that substantially fully covers or encapsulates an outer surface of housing 27 in addition to a conformal coating or encapsulant that encapsulates components housed in housing 27.

As shown in FIG. 1, leads 18, 20, 22 extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. As described in further detail with reference to FIG. 5, in other examples, ICD 16 may deliver stimulation therapy to heart 14 by delivering stimulation to an extravascular tissue site in addition to or instead of delivering stimulation via electrodes of intravascular leads 18, 20, 22.

ICD 16 may sense electrical signals attendant to the depolarization and repolarization of heart 14 via electrodes (not shown in FIG. 1) coupled to at least one of the leads 18, 20, 22. In some examples, ICD 16 provides pacing pulses to heart 14 based on the electrical signals sensed within heart 14. These electrical signals sensed within heart 14 may also be referred to as cardiac signals or electrical cardiac signals. The configurations of electrodes used by ICD 16 for sensing and pacing may be unipolar or bipolar. ICD 16 may also provide defibrillation therapy and/or cardioversion therapy via electrodes located on at least one of the leads 18, 20, 22. ICD 16 may detect arrhythmia of heart 14, such as fibrillation of ventricles 28 and 32, and deliver defibrillation therapy to heart 14 in the form of electrical pulses. In some examples, ICD 16 may be programmed to deliver a progression of therapies, e.g., pulses with increasing energy levels, until a fibrillation of heart 14 is stopped. ICD 16 detects fibrillation employing one or more fibrillation detection techniques known in the art.

In the example of FIG. 1, INS 26 has been implanted in patient 12 proximate to an extravascular target stimulation site 40, such as a tissue site proximate a vagus nerve. For example, INS 26 may be subcutaneously or submuscularly implanted in the body of a patient 12 (e.g., in a chest cavity, lower back, lower abdomen, or buttocks of patient 12). INS 26 provides a programmable stimulation signal (e.g., in the form of electrical pulses or a continuous signal) that is delivered to target stimulation site 40 by implantable medical lead 28, and more particularly, via one or more stimulation electrodes carried by lead 28. Proximal end 28A of lead 28 may be both electrically and mechanically coupled to connector block 42 of INS 26 either directly or indirectly (e.g., via a lead extension). In particular, conductors disposed in the lead body may electrically connect stimulation electrodes (and sense electrodes, if present) of lead 28 to INS 26.

INS 26 may also be referred to as a signal generator. In some examples, lead 28 may also carry one or more sense electrodes to permit INS 26 to sense electrical signals from target stimulation site 40. Furthermore, in some examples, INS 26 may be coupled to two or more leads, e.g., for bilateral or multi-lateral stimulation. In examples where lead 28 carries one or more sense electrodes, the sense electrodes may be coupled to a sensing module within INS 26. The sensing module may be configured to withstand without damage approximately 500 volts at its inputs, e.g., inputs that couple to the sense electrodes.

Proximal end 28A of lead 28 may be both electrically and mechanically coupled to connector block 42 of INS 26 either directly or indirectly (e.g., via a lead extension). Conductors disposed in the lead body of lead 28 may electrically connect stimulation electrodes (and sense electrodes, if present) carried by lead 28 to INS 26. In some examples, in addition to conductors, the lead body of lead 28 may comprise a plurality of resistors that electrically couple electrodes of lead 28 to components of INS 26. The resistors may be positioned, for example, between a respective electrode of lead 28 and a sensing module within INS 26. In some examples, a first side of a resistor may be coupled to at least one of the electrodes of lead 28, and a second side the resistor may be electrically coupled to components within INS 26 via a respective conductor, e.g., a conductive wire.

The size of the resistor may be selected to be sufficiently low to permit INS 26 to deliver stimulation to patient 12 via lead 28, but sufficiently high to mitigate or substantially eliminate shunt-current for a given size, location, and configuration of electrodes of lead 28. In some examples, the resistance of the resistor may be selected to be an order of magnitude (e.g., about 10 times) less than the highest impedance of an electrode electrically connected to lead 28. In addition, the resistance of the resistor may be selected to be substantially equal to or less than the lowest impedance of an electrode electrically connected to lead 28. However, in some examples, the resistance of the resistors may be selected to be greater than the highest impedance of an electrode electrically connected to lead 28. In some examples, the resistors of lead 28 may be between approximately 10 ohms and approximately 10 kiloohms each. In other examples, the resistors of lead 28 may be greater than approximately 10 kiloohms or greater. However, any suitable resistor value may be utilized.

In other examples, at least one of the electrodes of lead 28 may be coupled to an inductor, which may slow relatively large, substantially instantaneous pulses of current while allowing smaller pulses of current to pass. In one example, the inductor may comprise a coiled conductor with a relative high coiling pitch.

In some examples, in addition to the plurality of resistors, the lead body of lead 28 comprises a plurality of switches. Each switch of the plurality of switches may be coupled in parallel a respective resistor. A first side of each switch may be coupled to at least one of the electrodes of lead 28 and a second side of each switch may be coupled to INS 26 (e.g., a signal generator or a sensing module of INS 26). INS 26 may close the switch during delivery of a stimulation signal via electrodes of lead 28. In all other instances, the switch may remain open. During delivery of stimulation signal by INS 26, the closed switch may provide a relatively lower impedance path from INS 26 to the at least one electrode of lead 28, as compared to the electrical path through an open switch and/or resistor. In all other instances, the switch may remain open and the resistor may limit the shunt-current into INS 26. In other examples, there is no resistor connected in parallel across each switch. When the switch opens, an open circuit results, and thus shunt-current is minimized or even eliminated.

In some examples, instead of or in addition to a plurality of resistors, the lead body may comprise resistive wires. The lead body may comprise the resistive wires instead of or in addition to the conductors of lead 28. In some cases, the resistive wires may electrically couple the electrodes or the second side of each resistor to components (e.g., a stimulation generator or sensing module) within INS 26. In some examples, the resistive wires may provide approximately 10 kiloohms to approximately 10 kiloohms of resistance each. In some examples, the resistive wires may provide approximately 10 ohms to 100 ohms of resistance each, or approximately 3.5 kiloohms to approximately 10 kiloohms of resistance each. However, any resistive value may be utilized by this disclosure. In other examples, the wire itself may be resistive and/or an integral resistor may be present within the lead.

In some examples, in addition to the resistive wires, the lead body of lead 28 comprises a plurality of switches. Each switch of the plurality of switches may be coupled in parallel with each one of the resistive wires. In such examples, INS 26 may close the plurality of switches during delivery of a stimulation signal. In all other instances, the switches may remain open. During delivery of stimulation signal by INS 26, the closed switches may provide a relatively lower impedance path from INS 26 to the electrodes of lead 28, as compared to the electrical path through an open switch and/or resistor wires. In all other instances, the switches may remain open and the resistive wires may limit the shunt-current into INS 26.

The resistive wires and/or the resistors may increase the impedance of an electrical path including electrodes carried by lead 28, through which shunt-current may travel from ICD 16 to INS 26. Increasing the impedance of the electrical path including electrodes carried by lead 28 may help reduce the amount of shunt-current that flows into the stimulation generation circuitry or sensing circuitry within INS 26 via the electrodes coupled to INS 26. The amount of shunt-current that flows into tissue near the electrodes carried by lead 28 may be reduced because the amount of shunt-current that flows into the stimulation generation circuitry or sensing circuitry within INS 26 is reduced. In this way, reducing the amount of shunt-current that flows through tissue proximate electrodes of lead 28 may help decrease the possibility that tissue near the electrodes may be unintentionally stimulated. Although the resistors, inductors, resistive wires, and/or switches are described as being located within lead 28, in some examples, the resistors, inductors, resistive wires, and/or switches may be located within housing 27 of INS 26, connector block 42 of INS 26 or a lead connector (e.g., a lead extension) coupled to INS 26. The resistors, inductors, resistive wires, and/or switches coupled to one or more electrodes of lead 28 may be referred to as shunt-current mitigation circuitry that is coupled to the stimulation and/or sensing electrodes of lead 28.

Delivery of electrical stimulation by INS 26 to a nonmyocardial tissue or a nonvascular cardiac tissue site (e.g., one or more tissue sites proximate to a nerve, nerve site, cardiac fat pad, or an extravascular target tissue site) that is not proximate a nerve may provide cardiovascular benefits to patient 12. As previously indicated, an extravascular tissue site may be outside of heart 14 and outside of arteries, veins, or other vasculature of patient 12. For example, delivery of neurostimulation by INS 26 may help treat heart failure. In addition, in some examples, delivery of electrical stimulation to the tissue site may help reduce or eliminate cardiovascular conditions such as tachycardia, unhealthy cardiac contractions, ischemia, inefficient heart pumping, inefficient collateral circulation of heart 14 or cardiac muscle trauma.

In the example shown in FIG. 1, INS 26 provides electrical stimulation therapy of a parasympathetic nerve, such as a vagus nerve, of patient 12. Stimulation of a parasympathetic nerve of patient 12 may help slow intrinsic rhythms of heart 14, which may improve heart failure disease status of the patient 12. In this way, neurostimulation by INS 26 may help control a heart rate of patient 12 or otherwise control cardiac function.

In other examples, electrodes of lead 28 may be positioned to deliver electrical stimulation to any other suitable nerve, organ, muscle or muscle group in patient 12, which may be selected based on, for example, a therapy regimen selected for a particular patient. In some examples, INS 26 may deliver electrical stimulation to other parasympathetic nerves, baroreceptors, the carotid sinus or a cardiac branch of the vagal trunk of patient 12 in order to facilitate the delivery of therapy by ICD 16.

The electrical stimulation signals generated and delivered by INS 26 may be referred to as neurostimulation signals. However, in some examples, INS 26 may deliver electrical stimulation to a target tissue site 40 that is not proximate to a nerve. For example, INS 26 may deliver electrical stimulation to a peripheral nerve field site, and electrodes 124 (FIG. 7) electrically connected to INS 26 may be implanted in a region where patient 12 experiences pain. The pain may be related to stimulation delivered by ICD 16 or a patient condition, such as angina or chronic back pain. As other examples, INS 26 may deliver electrical stimulation to a muscle, muscle group, organ, or other sites that may not be proximate a nerve. Thus, while "neurostimulation" signals are primarily referred to herein, the disclosure is also applicable to examples in which INS 26 delivers electrical stimulation to other sites than tissue sites proximate a nerve. A tissue site proximate a nerve may be a neural tissue site to which delivery of electrical stimulation may activate the nerve. In some examples, a tissue site proximate a nerve may be in a range of about zero centimeters to about 10 centimeters from the nerve, although other distance ranges are contemplated and may depend upon the nerve.

Figure 2:
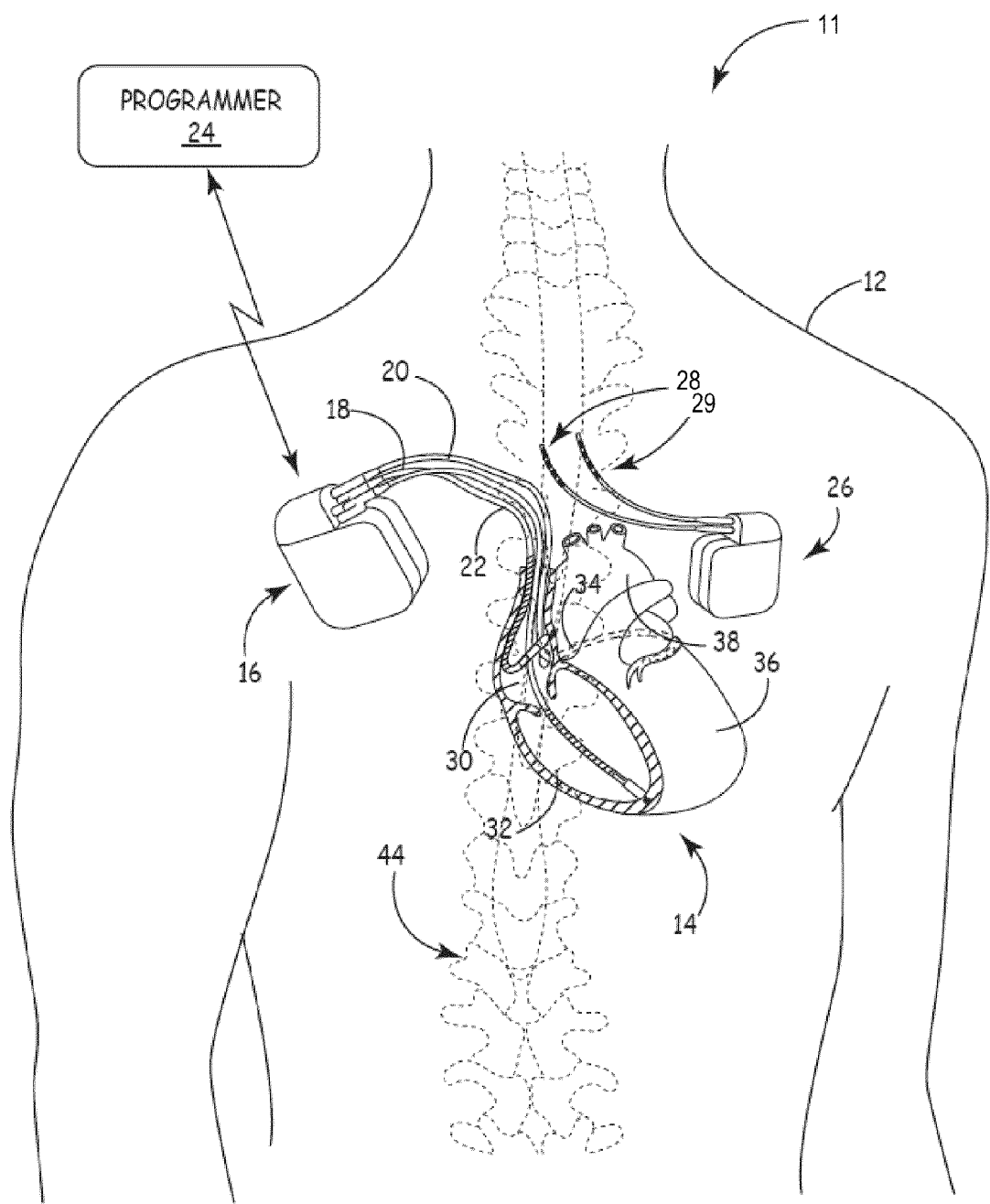
FIG. 2 is a conceptual diagram illustrating another example therapy system that includes the ICD and the INS.

As another example, as shown in FIG. 2, INS 26 may be positioned to deliver electrical stimulation to spinal cord 44 of patient 12. Stimulation of spinal cord 44 or nerves branching therefrom by INS 26 may help prevent or mitigate occurrences of tachyarrhythmias and may facilitate reduction of the level of aggressiveness of the cardiac therapy, such as pacing, cardioversion or defibrillation, delivered by ICD 16. In this way, ICD 16 and INS 26 may operate in conjunction with each other to help prevent arrhythmias of heart 14 of patient 12, as well as to terminate detected arrhythmias.

In some examples, depending upon the neurostimulation target, the delivery of electrical stimulation by INS 26 may also mitigate perceptible discomfort generated from the delivery of pacing pulses or cardioversion/defibrillation shocks by ICD 16. For example, if INS 26 delivers electrical stimulation to spinal cord 44 of patient 12, the neurostimulation may produce paresthesia, which may help reduce the discomfort felt by patient 12 from the delivery of stimulation by ICD 16.

In the example shown in FIG. 2, therapy system 11 includes INS 26, which is coupled to two leads 28, 29 to provide bilateral stimulation of spinal cord 44. Leads 28, 29 may be introduced into spinal cord 44 in the thoracic region, as shown in FIG. 2. In other examples, leads 28, 29 may be introduced into spinal cord 44 in the cervical or lumbar regions. Electrodes of leads 28, 29 may be positioned within an intrathecal space or epidural space of spinal cord 44, or, in some examples, adjacent nerves that branch off spinal cord 44. In some examples, leads 28, 29 are implanted within patient 12 and positioned such that electrodes of leads 28, 29 deliver electrical stimulation to locations proximate to the T1 to T6 thoracic vertebrae of the vertebral column of patient 12. For example, electrodes of at least one of the leads 28, 29 may span the T3 to T6 thoracic vertebrae or deliver electrical stimulation to a tissue site proximate at least one of the T3 to T6 thoracic vertebrae. In other examples, leads 28, 29 may be implanted to deliver electrical stimulation to other regions proximate or within spinal cord 44, such as over or near other vertebrae.

In some examples, the shunt-mitigation circuitry may include a monitor that determines an electrical parameter value at the stimulation or sensing electrodes, i.e. therapeutic electrodes, of leads 28, 29 and a switch coupled to the monitor. The switch, which opens or closes the electrical path between the one or more electrodes of leads 28, 29, e.g. the therapeutic electrodes, and the stimulation or sensing circuitry of INS 26, may be opened or closed based on the electrical parameter value. A processor of INS 26 may control the switch based on the electrical parameter value measured by the monitor. In other examples, the monitor controls the switch based on the electrical parameter value measured by the monitor.

The monitor may include, for example, a voltage monitor or a current monitor electrically coupled to one or more of the leads 28, 29. The voltage monitor or current monitor may be coupled to a switch that is coupled in series to circuitry within INS 26. In other words, the switch may be located between the voltage monitor or current monitor and the circuitry within INS 26. At least some of the stimulation and sensing electrodes of leads 28, 29 may be electrically coupled to a first side of a current or voltage monitor. A second side of the current or voltage monitor may be electrically coupled to a first side of a switch, and a second side of the switch may be coupled to circuitry within INS 26, e.g. the stimulation generation circuitry or sensing circuitry within INS 26. In this way, the electrical path between at least some of the electrodes of leads 28, 29 and the stimulation generation circuitry and sensing circuitry within INS 26 may be selectively opened or closed.

In some examples, a voltage monitor coupled to an electrode may monitor the voltage at a respective one of the stimulation or sensing electrodes. If the voltage is greater than or equal to a threshold voltage value, the voltage monitor may cause the switch to toggle open, such that no current can flow from the respective stimulation or sensing electrodes to the circuitry within INS 26. In this manner, the shunt-current that feeds into the circuitry within INS 26 through an electrical path including an electrode carried by lead 28 may be minimized or even eliminated. The threshold voltage may be stored within the voltage monitor or may be stored within INS 26.

In some examples, the threshold voltage value may range from about 10 volts to about 1000 volts, such as about 10 volts to about 50 volts, although other threshold voltage values are contemplated. A relatively high threshold voltage value may be useful if INS 26 includes a high voltage blocking circuit that may be able to withstand high voltages that INS 26 may be exposed to. However, because there may be a possibility for INS 26 to be exposed to higher voltages than the high voltage blocking circuit is designed to withstand, INS 26 may include shunt-current mitigation circuitry 119, as described herein. In some examples, when the switch is opened to limit shunt current, stimulation may be temporarily disabled. The cessation of stimulation may be sufficiently brief to not appreciably affect the stimulation therapy. Examples of switches that may be coupled to voltage monitors include, but are not limited to, electronic switches, field effect transistor (FET) switches, reed switches, optical isolations, silicon controlled rectifier (SCR), other silicon-based clamping structures, or other electrical components.

If a current monitor is electrically coupled to a stimulation or sensing electrode of leads 28, 29, the current monitor may monitor the current through the respective stimulation or sensing electrode. If the current exceeds a threshold current value, the current monitor may cause the switch to toggle open such that no current can flow to the circuitry within INS 26. Alternatively, a processor within INS 26 may cause the switches to toggle open. Just as with the voltage monitor, toggling the switch to an open position may help limit or even eliminate the amount of shunt-current that feeds into the circuitry within INS 26 through an electrical path including an electrode carried by lead 28. The threshold voltage may be stored within the current monitor or may be stored within INS 26.

In some examples, the threshold current value limit is in a range from about 1 milliamps to about 100 amps, such as about 10 milliamps to about 50 milliamps or 1 milliamps to 10 amps, although other threshold current values are contemplated. As one non-limiting example, the total shunt-current that flows through all therapeutic electrodes of leads 28, 29 may range from 10 milliamps to about 100 amps. However, the amount of shunt-current that flows through each electrode may range from 1 milliamp to about 50 milliamps. Examples of switches that may be coupled to the current monitor include, but are not limited to, electronic switches, FET switches, reed switches, optical isolations, SCRs, and the like.

The threshold voltage value and threshold current values may be selected based on a number of factors. For example, the threshold voltage value and/or threshold current value may depend upon how much current or energy the circuitry (e.g., stimulation or sensing circuitry) within INS 26 may tolerate without substantial stress on the circuitry (e.g., stress that may affect operation). In addition, in some cases, the threshold voltage value and/or threshold current value may be selected to minimize unintentional stimulation of the patient's tissue. In these examples, the threshold voltage value and/or threshold current value may depend upon the size of electrodes that are electrically connected to INS 26 and the location of the electrodes because different types of tissue (e.g., subcutaneous tissue, muscle tissue, and the like) may have different current limitations.

In some examples, INS 26 delivers therapy to patient 12 with a voltage amplitude of about 0.2 volts to about 12 volts, a pulse duration of about 40 microseconds (μs) to about 600 μs, such as about 50 μs to about 500 μs), and a pulse rate of 1 to 100 Hz (e.g., 10 Hz to 100 Hz). However, other stimulation parameter values for INS 26 are contemplated. INS 26 may deliver electrical stimulation to patient 12 substantially continuously or periodically. In some examples, INS 26 may deliver electrical stimulation to patient 12 based on the timing of electrical stimulation by ICD 16, such as prior to the delivery of electrical stimulation (e.g., antitachycardia pacing or a defibrillation or cardioversion pulse) by ICD 16, during the delivery of electrical stimulation by ICD 16, subsequent to the delivery of electrical stimulation by ICD 16 or any combination of the aforementioned times.

In addition, in some examples, INS 26 may deliver electrical stimulation to patient 12 based on a sensed event, such as atrial or ventricular depolarization, or based on a sensed physiological condition. The event or physiological condition may be sensed by ICD 16, INS 26 or another sensing device. ICD 16 and INS 26 may communicate with each other in order for INS 26 to time the delivery of electrical stimulation based on the delivery of stimulation pulses by ICD 16, where the stimulation pulses delivered by ICD 16 may be pacing pulses or cardioversion/defibrillation pulses. ICD 16 and INS 26 may communicate directly or indirectly (e.g., via an intermediate device, such as programmer 24) using any suitable communication technique. Examples communication techniques that may be implemented to facilitate communication between ICD 16 and INS 26 may include, for example, radiofrequency (RF) communication techniques, optical communication techniques, ultrasonic communication techniques, and the like. Communication between ICD 16 and INS 26 may be periodic, e.g., according to a regular schedule, or on an as needed basis, e.g., when INS 26 delivers electrical stimulation to a tissue site within patient 12.

In other examples, INS 26 may deliver electrical stimulation to patient 12 independently of the electrical stimulation delivered by ICD 16. For example, INS 26 may be programmed to deliver electrical stimulation to patient 12 according to a schedule that is determined independently of the actual delivery of stimulation by ICD 16. The schedule may be determined, for example, by a clinician based on a trial stimulation period in which multiple therapy schedules for INS 26 are tested on patient 12. The schedule may dictate when INS 26 actively delivers electrical stimulation to patient 12 and when INS 26 does not actively deliver electrical stimulation to patient 12. For example, the schedule may include a mandatory sleep period for INS 26 during which INS 26 reverts to a relatively low-power sleep mode and does not deliver therapy to patient 12. The sleep period may be, for example, when patient 12 is sleeping or otherwise has a relatively low activity level. The sleep period may be useful for conserving the power within the power source of INS 26.

In some examples, communication between ICD 16 and INS 26 may also be used to trigger implementation of a shunt-current mitigation mode of INS 26. Prior to delivery of a stimulation signal by ICD 16, ICD 16 may communicate with INS 26 to indicate the prospective stimulation delivery by ICD 16. For example, ICD 16 may transmit a communication signal to INS 26 that indicates that ICD 16 is intending on delivering a stimulation signal (e.g., a defibrillation shock) to patient 12, e.g., within about five seconds or less. The communication signal may be an electrical signal that does not provide any therapeutic benefits to patient 12 or may be an electrical signal that provides therapeutic benefits to patient, e.g., may be a stimulation signal. Based on the indication that ICD 16 is about to provide a stimulation signal, e.g., a defibrillation shock, INS 26 may change an operating mode to a shunt-current mitigation mode. In some examples, the shunt-current mitigation mode may be implemented by shunt-current mitigation circuitry that includes switches that may help limit the current flow into the stimulation generation circuitry or sensing circuitry within of INS 26 through an electrical path including electrodes carried by lead 28.

For example, the sensing and stimulation electrodes electrically connected to one or more therapy modules within housing 27 of INS 26 may be coupled to a first side of a switch, and a second side of the switch may be coupled to the one or more therapy modules. Upon receiving the indication of prospective cardiac rhythm management therapy delivery by ICD 16 to patient 12, INS 26 may toggle the switches open to limit or even eliminate shunt-current flow through the sensing and stimulation electrodes electrically connected to the sensing or stimulation modules of INS 26. In some examples, a monitor (e.g., current and/or voltage monitor), as described above, may be coupled to the switches. In such examples, the switches may toggle open whenever the voltage or current monitor senses a voltage or current, respectively, that is greater than a threshold value, or the switches may toggle open in response to a signal indicative of the prospective cardiac rhythm management therapy delivery by ICD 16.

The values for the therapy parameters that define the electrical stimulation delivered by INS 26 may be organized into a group of parameter values referred to as a "therapy program" or "therapy parameter set." "Therapy program" and "therapy parameter set" are used interchangeably herein. In the case of electrical stimulation, the therapy parameters may include an electrode combination, and an amplitude, which may be a current or voltage amplitude, and, if INS 26 delivers electrical pulses, a pulse width, and a pulse rate for stimulation signals to be delivered to the patient. An electrode combination may include a selected subset of one or more electrodes of lead 28, as well as lead 29 in the case of therapy system 11 of FIG. 2. The electrode combination may also refer to the polarities of the electrodes in the selected subset. By selecting particular electrode combinations, a clinician may target particular anatomic structures within patient 12. In some cases, INS 26 may deliver stimulation to patient 12 according to a program group that includes more than one therapy program. The stimulation signals according to the different therapy programs in a therapy group may be delivered on a time-interleaved basis or substantially simultaneously.

If INS 26 delivers therapy to patient 12 according to two or more electrode combinations, e.g., according to a therapy program group including two or more therapy programs defining at least two different electrode combinations, time-interleaving the stimulation signals defined each of the therapy programs may result in stimulation that is sequentially applied to different electrodes.

Programmer 24 may include a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with ICD 16 and/or INS 26. For example, the user may interact with programmer 24 to retrieve physiological or diagnostic information from ICD 16 and/or INS 26. A user may also interact with programmer 24 to program ICD 16 and INS 26, e.g., select values for operational parameters of ICD 16 and INS 26, respectively.

For example, the user may use programmer 24 to retrieve information from ICD 16 regarding the rhythm of heart 14, trends therein over time, or tachyarrhythmia episodes. As another example, the user may use programmer 24 to retrieve information from ICD 16 regarding other sensed physiological parameters of patient 12, such as electrical depolarization/repolarization signals from the heart (referred to as "electrogram" or EGM), intracardiac or intravascular pressure, activity, posture, respiration, or thoracic impedance. As another example, the user may use programmer 24 to retrieve information from ICD 16 regarding the performance or integrity of ICD 16 or other components of system 10, such as leads 18, 20, and 22, or a power source of ICD 16.

The user may use programmer 24 to program a therapy progression, select electrodes used to deliver defibrillation pulses, select waveforms for the defibrillation pulse, or select or configure a fibrillation detection algorithm for ICD 16. The user may also use programmer 24 to program aspects of other therapies provided by INS 26, such as cardioversion or pacing therapies. In some examples, the user may activate certain features of ICD 16 by entering a single command via programmer 24, such as depression of a single key or combination of keys of a keypad or a single point-and-select action with a pointing device.

As another example, the user may use programmer 24 to retrieve information from INS 26 regarding the performance or integrity of INS 26 or lead 28 (and lead 29 if the therapy system includes lead 29), or a power source of INS 26. With the aid of programmer 24 or another computing device, a user may select values for therapy parameters for controlling therapy delivery by INS 26. By selecting values for amplitude, pulse width, and pulse rate, the clinician can attempt to generate an efficacious therapy for patient 12 that is delivered via the selected electrode subset.

Programmer 24 may communicate with ICD 16 and INS 26 via wireless communication using any techniques known in the art. Examples of communication techniques may include, for example, low frequency or RF telemetry, but other techniques are also contemplated. In some examples, programmer 24 may include a programming head that may be placed proximate to the patient's body near the ICD 16 and INS 26 implant sites in order to improve the quality or security of communication between ICD 16 or INS 26, respectively, and programmer 24.

Figure 3:
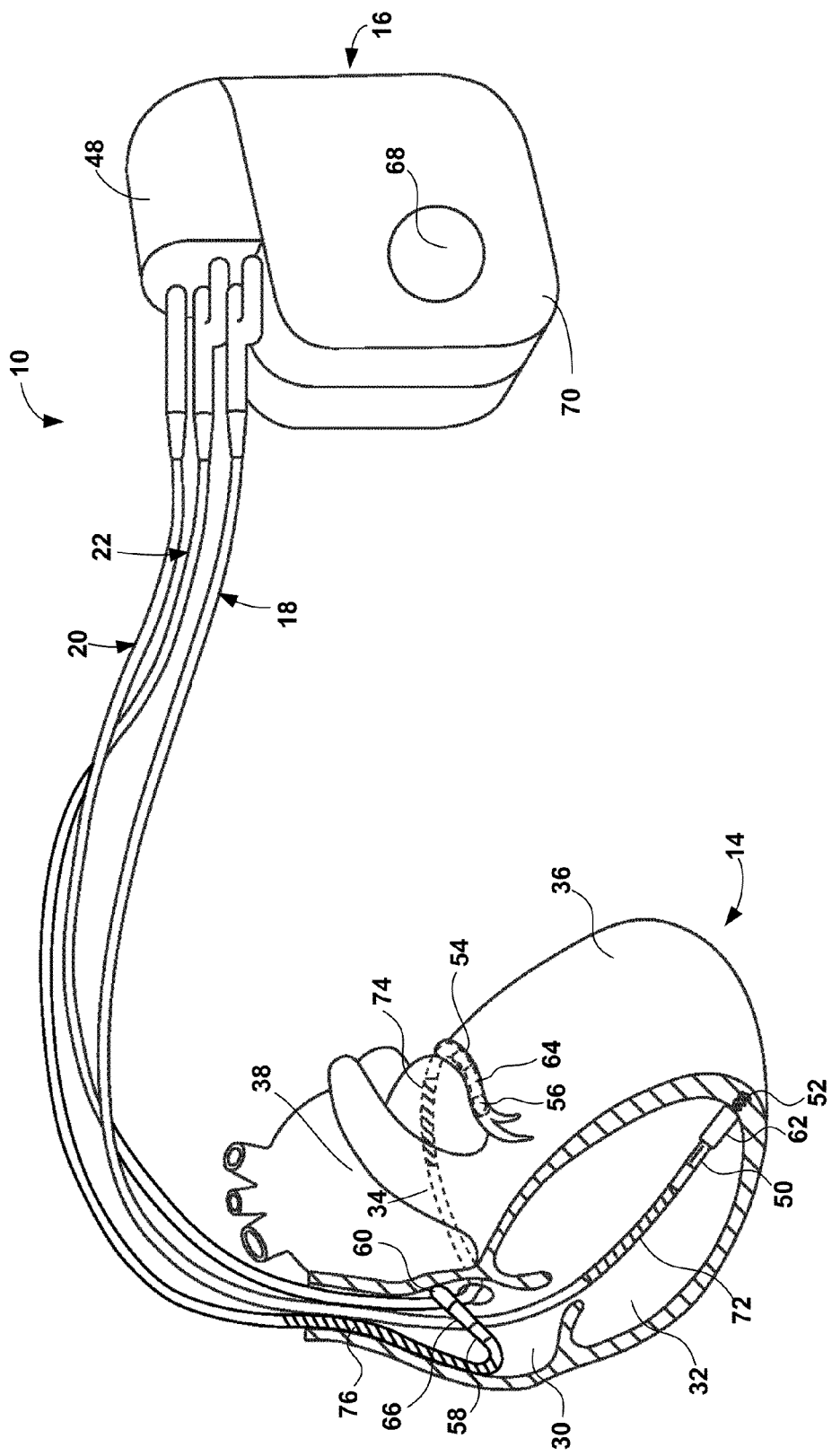
FIG. 3 is a conceptual diagram illustrating the ICD of FIGS. 1 and 2 and the respective leads in greater detail.

FIG. 3 is a conceptual diagram illustrating ICD 16 and leads 18, 20, and 22 of therapy system 10 in greater detail. Leads 18, 20, 22 may be electrically coupled to a stimulation generator, a sensing module, or other modules ICD 16 via connector block 48. In some examples, proximal ends of leads 18, 20, 22 may include electrical contacts that electrically couple to respective electrical contacts within connector block 48. In addition, in some examples, leads 18, 20, 22 may be mechanically coupled to connector block 48 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. Other lead configurations are also contemplated, such as configurations that do not include coiled conductors. In the illustrated example, bipolar electrodes 40 and 42 are located proximate to a distal end of lead 18. In addition, bipolar electrodes 54 and 56 are located proximate to a distal end of lead 20 and bipolar electrodes 58 and 60 are located proximate to a distal end of lead 22.

Electrodes 50, 54, and 58 may take the form of ring electrodes, and electrodes 52, 56, and 60 may take the form of extendable helix tip electrodes mounted retractably within insulative electrode heads 62, 64, and 66, respectively. Each of the electrodes 50, 52, 54, 56, 58, and 60 may be electrically coupled to a respective one of the coiled conductors within the lead body of its associated lead 18, 20, 22, and thereby coupled to respective ones of the electrical contacts on the proximal end of leads 18, 20 and 22.

Electrodes 50, 52, 54, 56, 58, and 60 may sense electrical signals attendant to the depolarization and repolarization of heart 14. The electrical signals are conducted to ICD 16 via the respective leads 18, 20, 22. In some examples, ICD 16 also delivers pacing pulses via electrodes 50, 52, 54, 56, 58, and 60 to cause depolarization of cardiac tissue of heart 14. In some examples, as illustrated in FIG. 2, ICD 16 includes one or more housing electrodes, such as housing electrode 68, which may be formed integrally with an outer surface of hermetically-sealed housing 70 of ICD 16 or otherwise coupled to housing 70. In some examples, housing electrode 68 is defined by an uninsulated portion of an outward facing portion of housing 70 of ICD 16. Other division between insulated and uninsulated portions of housing 70 may be employed to define two or more housing electrodes. In some examples, housing electrode 68 comprises substantially all of housing 70. Any of the electrodes 50, 52, 54, 56, 58, and 60 may be used for unipolar sensing or pacing in combination with housing electrode 68. As described in further detail with reference to FIG. 4, housing 70 may enclose a stimulation generator that generates cardiac pacing pulses and defibrillation or cardioversion shocks, as well as a sensing module for monitoring the patient's heart rhythm.

Leads 18, 20, 22 also include elongated electrodes 72, 74, 76, respectively, which may take the form of a coil. ICD 16 may deliver defibrillation pulses to heart 14 via any combination of elongated electrodes 72, 74, 76, and housing electrode 68. Electrodes 68, 72, 74, 76 may also be used to deliver cardioversion pulses to heart 14. Electrodes 72, 74, 76 may be fabricated from any suitable electrically conductive material, such as, but not limited to, platinum, platinum alloy or other materials known to be usable in implantable defibrillation electrodes.

The configurations of therapy system 10 illustrated in FIGS. 1-3 are merely examples. In other examples, a therapy system may include epicardial leads and/or patch electrodes instead of or in addition to the transvenous leads 18, 20, 22 illustrated in FIG. 1. Further, ICD 16 and INS 26 need not be implanted within patient 12. In examples in which ICD 16 is not implanted in patient 12, ICD 16 may deliver defibrillation pulses and other therapies to heart 14 via percutaneous leads that extend through the skin of patient 12 to a variety of positions within or outside of heart 14 or via electrodes external to patient 12 (e.g., external patch electrodes). In examples in which INS 26 is not implanted in patient 12, INS 26 may deliver electrical stimulation to target tissue sites within patient 12 via external electrodes or via percutaneous leads that extend through the skin of patient 12.

In other examples of therapy systems that provide electrical stimulation therapy to heart 14, a therapy system may include any suitable number of leads coupled to ICD 16, and each of the leads may extend to any location within or proximate to heart 14. Other examples of therapy systems may include three transvenous leads located as illustrated in FIGS. 1 and 3, and an additional lead located within or proximate to left atrium 38. Alternatively, other examples of therapy systems may include a single lead that extends from ICD 16 into right atrium 30 or right ventricle 32, or two leads that extend into a respective one of the right ventricle 32 and right atrium 30. An example of this type of therapy system is shown in FIG. 4.

Figure 4:
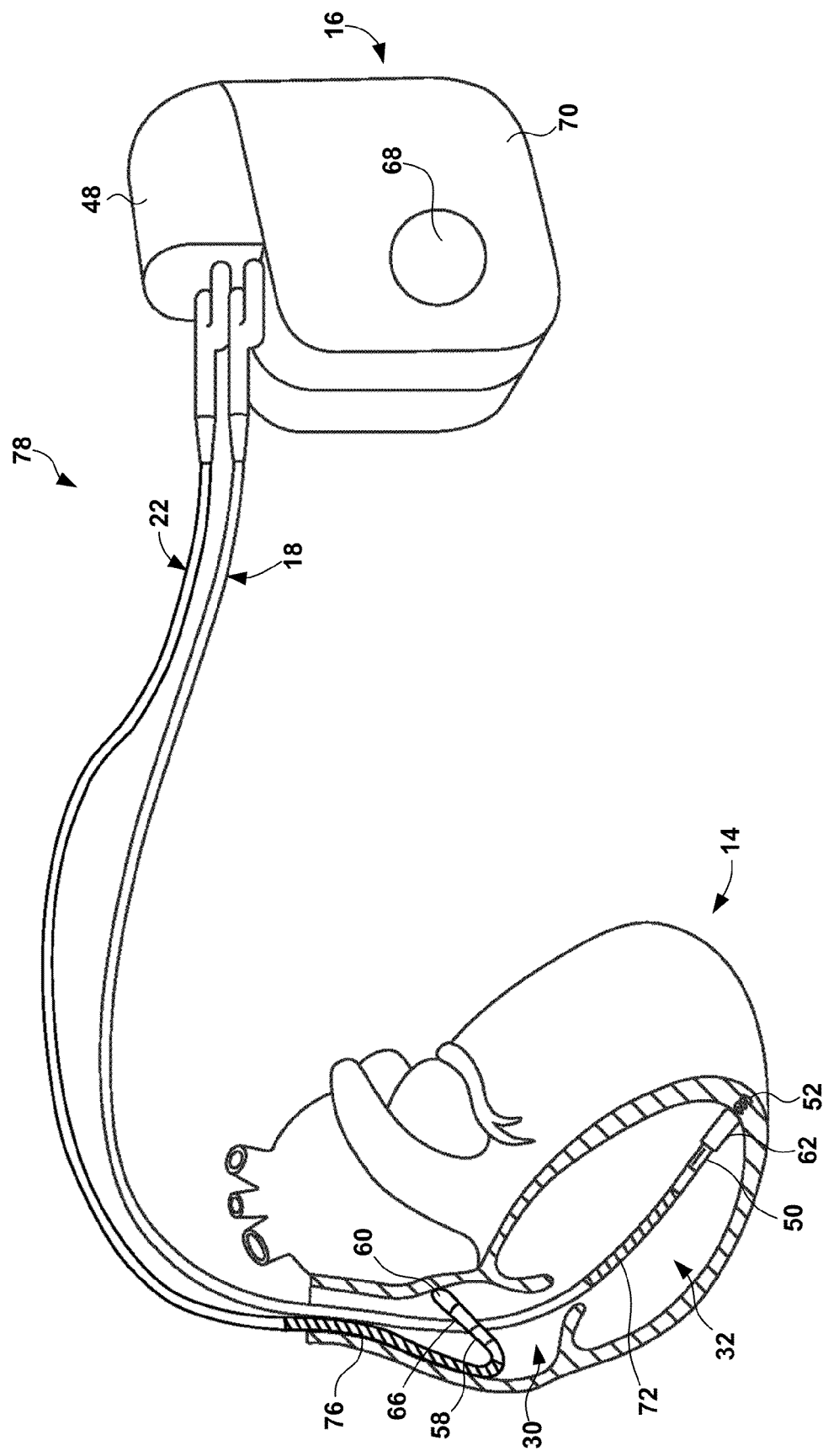
FIG. 4 is a conceptual diagram illustrating another example of the ICD of FIGS. 1 and 2 and the respective leads in greater detail.

FIG. 4 is a conceptual diagram illustrating another example of therapy system 78, which is similar to therapy system 10 of FIGS. 1 and 2, but includes two leads 18, 22, rather than three leads. Leads 18, 22 are implanted within right ventricle 32 and right atrium 30, respectively. Therapy system 78 shown in FIG. 4 may be useful for providing defibrillation and pacing pulses to heart 14. Therapy system 78 may further include INS 26 (not shown in FIG. 4), which is configured to deliver electrical stimulation therapy in order to help prevent or mitigate an arrhythmia of patient 12. As previously indicated, INS 26 may deliver stimulation therapy to modulate an autonomic nervous system of patient 12.

Figure 5:
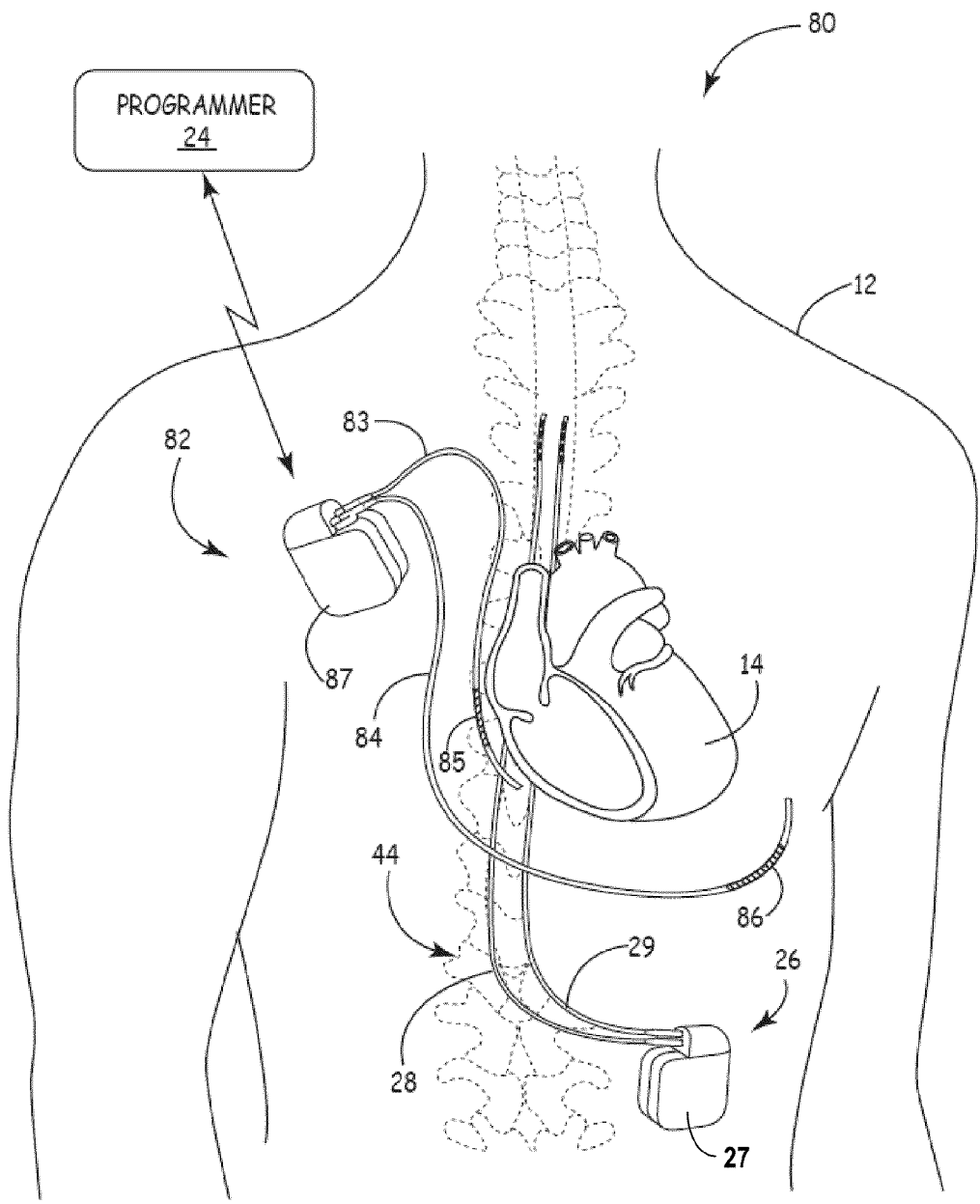
FIG. 5 is a conceptual diagram illustrating another example therapy system that includes an ICD and an INS.

FIG. 5 is a conceptual diagram of another example therapy system 80 that includes two medical devices that provide therapy to patient 12, e.g., to manage a cardiac condition such as heart failure. In addition to INS 26, therapy system 80 includes ICD 82, which delivers electrical stimulation to heart 14 without intravascular leads. ICD 82 is coupled to extravascular leads 83, 84, that each include at least one electrode 85, 86. Electrodes 85, 86 may be subcutaneous coil electrodes, which may be positioned within a subcutaneous tissue layer of patient 12. In other examples, electrodes 85, 86 may comprise any other suitable type of extravascular electrode. For example, electrodes 85, 86 may include any other type of subcutaneous electrode, such as subcutaneous ring electrodes, subcutaneous plate electrodes, subcutaneous patch or pad electrodes, a submuscular electrode, an epicardial electrode or an intramural electrode.

Electrodes 85 may be located within the thoracic cavity of patient 12 proximate to right ventricle 32 (FIG. 1), on the patient's side or back, or any other portion of the body appropriate for providing electrical stimulation to heart 14. Electrode 86 may be located within the thoracic cavity of patient 12 proximate left ventricle 36 (FIG. 1), on the patient's side or back, or any other portion of the body appropriate for providing electrical stimulation to the heart. Similar extravascular electrodes are disclosed in commonly-assigned U.S. Pat. No. 5,261,400 to Bardy, which is entitled "DEFIBRILLATOR EMPLOYING TRANSVENOUS AND SUBCUTANEOUS ELECTRODES AND METHOD OF USE" and issued Nov. 16, 1993, and U.S. Pat. No. 5,292,338 to Bardy, which is entitled "ATRIAL DEFIBRILLATOR EMPLOYING TRANSVENOUS AND SUBCUTANEOUS ELECTRODES AND METHOD OF USE" and issued Mar. 8, 1994. U.S. Pat. Nos. 5,261,400 and 5,292,338 are incorporated herein by reference in their entireties.

Leads 83, 84 may be electrically coupled to stimulation modules, and, in some cases, sensing modules, that are enclosed within housing 87 of ICD 82. As with housing 70 of ICD 16 (FIG. 3), housing 87 may comprise a hermetic housing that substantially encloses the components of ICD 16, such as a sensing module, stimulation generator, processor and the like. Components of an example ICD 16 or ICD 82 are described with respect to FIG. 6. ICD 82 may deliver electrical stimulation (e.g., pacing, cardioversion or defibrillation pulses) to heart 14 between electrodes 85, 86 e.g., in a bipolar configuration. In other examples, ICD 82 may deliver electrical stimulation to heart 14 between electrodes 85 and housing 87, or between electrode 86 and housing 87, e.g., in a unipolar configuration.

Just as with ICD 16 (FIG. 1) that delivers cardiac rhythm management therapy to heart 14 via intravascular electrodes, the delivery of electrical stimulation by ICD 82 may cause a shunt-current to flow through the electrodes electrically connected to INS 26 or through electrically conductive portions of outer housing 27 of INS 26. Thus, in therapy system 80, INS 26 may include a housing 27 including an electrically insulative layer or an electrically insulative pouch that substantially fully encapsulates housing 27 or at least the electrically conductive portions of outer housing 27, and, optionally, shunt-current mitigation circuitry, e.g., as described above with respect to FIG. 1.

In some examples, the delivery of electrical stimulation by INS 26 may cause a shunt-current to flow through a housing of ICD 16 or the electrodes of leads 18, 20, and 22 electrically connected to ICD 16 (FIG. 1), or through housing 87 or leads 83, 84 electrically connected to ICD 82 (FIG. 5). In accordance with this disclosure, the various shunt-current mitigation techniques (e.g., a housing 87 including an electrically insulative layer, an insulative pouch that substantially fully encapsulates housing 87, or shunt-current mitigation circuitry) described herein may be used to mitigate the shunt-current that may flow through electrodes connected to ICD 16 or the housing of ICD 16. For purposes of clarity and illustration, the housing 27 including the electrically insulative layer, the electrically insulative pouch that substantially fully encapsulates housing 27, and shunt-current mitigation circuitry are described with respect to INS 26. However, the various shunt-current mitigation techniques described herein may be coupled to the housing or the electrodes of leads that couple to ICD 16 or ICD 82. While the disclosure primarily refers to therapy system 10 including ICD 16 (FIG. 1) and INS 26, the description of the techniques, systems, and devices herein are also applicable to therapy system 80 including ICD 82 and INS 26.

In some examples, stimulation signals delivered by an AED may cause shunt-current to flow into INS 26 or ICD 16. The housing including the electrically insulative layer, the electrically insulative pouch that substantially fully encapsulates the housing, and/or the shunt-mitigation circuitry described herein may also be used to limit that amount of shunt-current generated by a stimulation from an AED that feeds into INS 26 or ICD 16. In some examples in which an AED generates a shunt-current, only one of the implantable medical devices, e.g., either INS 26 or ICD 16, may be implanted within patient 12.

Figure 6:
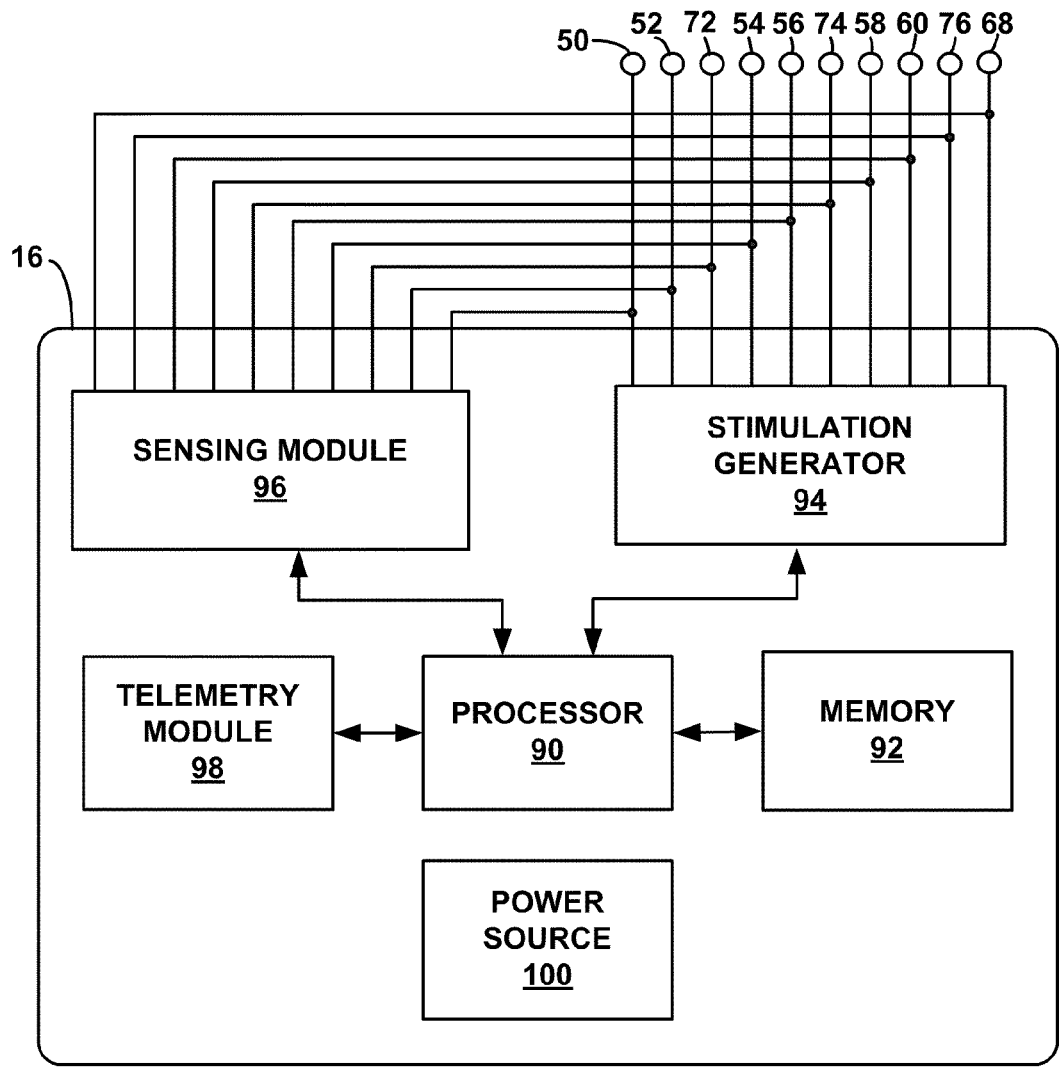
FIG. 6 is a functional block diagram of an example ICD that generates and delivers electrical stimulation to a heart of a patient.

FIG. 6 is a functional block diagram of an example configuration of ICD 16 (FIG. 1), which includes processor 90, memory 92, stimulation generator 94, sensing module 96, telemetry module 98, and power source 100. The block diagram shown in FIG. 6 may also illustrate an example configuration of ICD 82 (FIG. 5). Memory 92 includes computer-readable instructions that, when executed by processor 90, cause ICD 16 and processor 90 to perform various functions attributed to ICD 16 and processor 90 herein. Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 90 may include any one or more of a microprocessor, a controller, a digital signal processor (DSP), an application specific integrated circuit (ASIC), a field-programmable gate array (FPGA), or equivalent discrete or integrated logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof. Processor 90 controls stimulation generator 94 to deliver stimulation therapy to heart 14 (FIG. 1) according to a selected one or more of therapy programs, which may be stored in memory 92. Specifically, processor 90 may control stimulation generator 94 to deliver electrical pulses with the amplitudes, pulse widths, frequency, or electrode polarities specified by the selected one or more therapy programs.

Stimulation generator 94 is electrically coupled to electrodes 50, 52, 54, 56, 58, 60, 68, 72, 74, and 76, e.g., via conductors of the respective lead 18, 20, 22, or, in the case of housing electrode 68, via an electrical conductor disposed within housing 70 of ICD 16. Stimulation generator 94 is configured to generate and deliver cardiac rhythm management therapy to heart 14. For example, stimulation generator 94 may deliver defibrillation shocks to heart 14 via at least two electrodes 68, 72, 74, 76. Stimulation generator 94 may deliver pacing pulses via ring electrodes 50, 54, 58 coupled to leads 18, 20, and 22, respectively, and/or helical electrodes 52, 56, and 60 of leads 18, 20, and 22, respectively. In some examples, stimulation generator 94 delivers pacing, cardioversion, or defibrillation stimulation in the form of electrical pulses. In other examples, stimulation generator 94 may deliver one or more of these types of stimulation in the form of other signals, such as sine waves, square waves, or other substantially continuous time signals.

In some examples, stimulation generator 94 may include a switch module (not shown in FIG. 6) and processor 90 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes. In other examples, however, stimulation generator 94 may independently deliver stimulation to electrodes 50, 52, 54, 56, 58, 60, 68, 72, 74, and 76 or selectively sense via one or more of electrodes 50, 52, 54, 56, 58, 60, 68, 72, 74, and 76 without a switch matrix.

Sensing module 96 monitors signals from at least one of electrodes 50, 52, 54, 56, 58, 60, 68, 72, 74, and 76 in order to monitor electrical activity of heart 14, e.g., via an EGM signal. Sensing module 96 may also include a switch module (not shown in FIG. 6) to select a particular subset of available electrodes to sense the heart activity. In some examples, processor 90 may select the electrodes that function as sense electrodes via the switch module within sensing module 96, e.g., by providing signals via a data/address bus. In some examples, sensing module 96 includes one or more sensing channels, each of which may comprise an amplifier. In response to the signals from processor 90, the switch module of within sensing module 96 may couple the outputs from the selected electrodes to one of the sensing channels.

In some examples, shunt-current mitigation circuitry described herein with respect to INS 26 may also be used to electrically connect electrodes 50, 52, 54, 56, 58, 60, 68, 72, 74, and 76 to stimulation generator 94 and sensing module 96. The shunt-current mitigation circuitry may be located between ICD 16 and the electrodes. In addition, at least the electrically conductive portions of the outer housing of ICD 16 may include in some examples an electrically insulative layer as described in this disclosure with respect to housing 27 of INS 26, and/or the housing of ICD 16 or circuitry within the housing of ICD 16 may be substantially fully encapsulated in an electrically insulative pouch.

One channel of sensing module 96 may include an R-wave amplifier that receives signals from electrodes 50 and 52, which are used for pacing and sensing in right ventricle 32 of heart 14. Another channel may include another R-wave amplifier that receives signals from electrodes 54 and 56, which are used for pacing and sensing proximate to left ventricle 36 of heart 14. In some examples, in one operating mode of sensing module 96, the R-wave amplifiers may take the form of an automatic gain controlled amplifier that provides an adjustable sensing threshold as a function of the measured R-wave amplitude of the heart rhythm.

In addition, in some examples, one channel of sensing module 96 may include a P-wave amplifier that receives signals from electrodes 58 and 60, which are used for pacing and sensing in right atrium 30 of heart 14. In some examples, in one operating mode of sensing module 96, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 96 may be selectively coupled to housing electrode 68, or elongated electrodes 72, 74, or 76, with or instead of one or more of electrodes 50, 52, 54, 56, 58 or 60, e.g., for unipolar sensing of R-waves or P-waves in any of chambers 30, 32, or 36 of heart 14.

In some examples, sensing module 96 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 92 as an EGM. In some examples, the storage of such EGMs in memory 92 may be under the control of a direct memory access circuit. Processor 90 may employ digital signal analysis techniques to characterize the digitized signals stored in memory 92 to detect and classify the patient's heart rhythm from the electrical signals. Processor 90 may detect and classify the heart rhythm of patient 12 by employing any of the numerous signal processing methodologies known in the art.

If ICD 16 is configured to generate and deliver pacing pulses to heart 14, processor 90 may include pacer timing and control module, which may be embodied as hardware, firmware, software, or any combination thereof. The pacer timing and control module may comprise a dedicated hardware circuit, such as an ASIC, separate from other components of processor 90, such as a microprocessor, or a software module executed by a component of processor 90, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided. In some examples, when the third letter is a "D," it may indicate that the signal is used for tracking purposes (e.g., DDD uses atrial sensing to trigger ventricular pacing).

Intervals defined by the pacer timing and control module within processor 90 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 96 to blank one or more channels, e.g., amplifiers, for a period during and after delivery of electrical stimulation to heart 14. The durations of these intervals may be determined by processor 90 in response to stored data in memory 92. The pacer timing and control module of processor 90 may also determine the amplitude of the cardiac pacing pulses.

During pacing, escape interval counters within the pacer timing/control module of processor 90 may be reset upon sensing of R-waves and P-waves. Stimulation generator 94 may include pacer output circuits that are coupled, e.g., selectively by a switching module, to any combination of electrodes 50, 52, 54, 56, 58, 60, 68, 72, 74, and 76 appropriate for delivery of a bipolar or unipolar pacing pulse to one of the chambers of heart 14. Processor 90 may reset the escape interval counters upon the generation of pacing pulses by stimulation generator 94, and thereby control the basic timing of cardiac pacing functions, including anti-tachyarrhythmia pacing.

The value of the count present in the escape interval counters when reset by sensed R-waves and P-waves may be used by processor 90 to measure the durations of R-R intervals, P-P intervals, P-R intervals and R-P intervals, which are measurements that may be stored in memory 92. Processor 90 may use the count in the interval counters to detect a tachyarrhythmia event, such as ventricular fibrillation event or ventricular tachycardia event. Upon detecting a threshold number of tachyarrhythmia events, processor 90 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode. In the case of a NST, however, the count in the interval counters may not meet the requirements for triggering a therapeutic response.

In some examples, processor 90 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 90 and any updating of the values or intervals controlled by the pacer timing and control module of processor 90 may take place following such interrupts. A portion of memory 92 may be configured as a plurality of recirculating buffers, capable of holding series of measured intervals, which may be analyzed by processor 90 in response to the occurrence of a pace or sense interrupt to determine whether heart 14 of patient 12 is presently exhibiting atrial or ventricular tachyarrhythmia.

In some examples, an arrhythmia detection method may include any suitable tachyarrhythmia detection algorithms. In one example, processor 90 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 90 in other examples.

In the examples described herein, processor 90 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 92 of ICD 16. In addition, the number of tachyarrhythmia events that are detected to confirm the presence of a tachyarrhythmia episode may be stored as a number of intervals to detect (NID) threshold value in memory 92. In some examples, processor 90 may also identify the presence of the tachyarrhythmia episode by detecting a variability of the intervals between tachycardia events. For example, if the interval between successive tachyarrhythmia events varies by a particular percentage or the differences between the coupling intervals are higher than a given threshold over a predetermined number of successive cycles, processor 90 may determine that the tachyarrhythmia is present.

If processor 90 detects an atrial or ventricular tachyarrhythmia based on signals from sensing module 96, and an anti-tachyarrhythmia pacing regimen is desired, timing intervals for controlling the generation of anti-tachyarrhythmia pacing therapies by stimulation generator 94 may be loaded by processor 90 into the pacer timing and control module to control the operation of the escape interval counters therein and to define refractory periods during which detection of R-waves and P-waves is ineffective to restart the escape interval counters.

If ICD 16 is configured to generate and deliver defibrillation pulses to heart 14, stimulation generator 94 may include a high voltage charge circuit and a high voltage output circuit. In the event that generation of a cardioversion or defibrillation pulse is required, processor 90 may employ the escape interval counter to control timing of such cardioversion and defibrillation pulses, as well as associated refractory periods. In response to the detection of atrial or ventricular fibrillation or tachyarrhythmia requiring a cardioversion pulse, processor 90 may activate a cardioversion/defibrillation control module, which may, like pacer timing and control module, be a hardware component of processor 90 and/or a firmware or software module executed by one or more hardware components of processor 90. The cardioversion/defibrillation control module may initiate charging of the high voltage capacitors of the high voltage charge circuit of stimulation generator 94 under control of a high voltage charging control line.

Processor 90 may monitor the voltage on the high voltage capacitor, e.g., via a voltage charging and potential (VCAP) line. In response to the voltage on the high voltage capacitor reaching a predetermined value set by processor 90, processor 90 may generate a logic signal that terminates charging. Thereafter, timing of the delivery of the defibrillation or cardioversion pulse by stimulation generator 94 is controlled by the cardioversion/defibrillation control module of processor 90. Following delivery of the fibrillation or tachycardia therapy, processor 90 may return stimulation generator 94 to a cardiac pacing function and await the next successive interrupt due to pacing or the occurrence of a sensed atrial or ventricular depolarization.

Stimulation generator 94 may deliver cardioversion or defibrillation pulses with the aid of an output circuit that determines whether a monophasic or biphasic pulse is delivered, whether housing electrode 68 serves as cathode or anode, and which electrodes are involved in delivery of the cardioversion or defibrillation pulses. Such functionality may be provided by one or more switches or a switching module of stimulation generator 94.

Telemetry module 98 includes any suitable hardware, firmware, software or any combination thereof for communicating with another device, such as programmer 24 (FIG. 1). Under the control of processor 90, telemetry module 98 may receive downlink telemetry from and send uplink telemetry to programmer 24 with the aid of an antenna, which may be internal and/or external. Processor 90 may provide the data to be uplinked to programmer 24 and the control signals for the telemetry circuit within telemetry module 98, e.g., via an address/data bus. In some examples, telemetry module 98 may provide received data to processor 90 via a multiplexer. Moreover, in some examples, processor 90 may cause telemetry module 98 to transmit a signal to INS 26 that is indicative of prospective therapy delivery by ICD 16, e.g., a signal that indicatives ICD 16 is about to deliver a stimulation signal to patient 12.

In some examples, processor 90 may transmit atrial and ventricular heart signals (e.g., EGM signals) produced by atrial and ventricular sense amp circuits within sensing module 96 to programmer 24. Programmer 24 may interrogate ICD 16 to receive the heart signals. Processor 90 may store heart signals within memory 92, and retrieve stored heart signals from memory 92. Processor 90 may also generate and store marker codes indicative of different cardiac episodes that sensing module 96 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. In some examples, data from sensing module 96 may be uploaded to a remote server, from which a clinician or another user may access the data to determine whether a potential sensing integrity issue exists. An example of a remote server includes the CareLink Network, available from Medtronic, Inc. of Minneapolis, Minn.

The various components of ICD 16 are coupled to power source 100, which may include a rechargeable or non-rechargeable battery. A non-rechargeable battery may be selected to last for several years, while a rechargeable battery may be inductively charged from an external device, e.g., on a daily or weekly basis.

Figure 7:
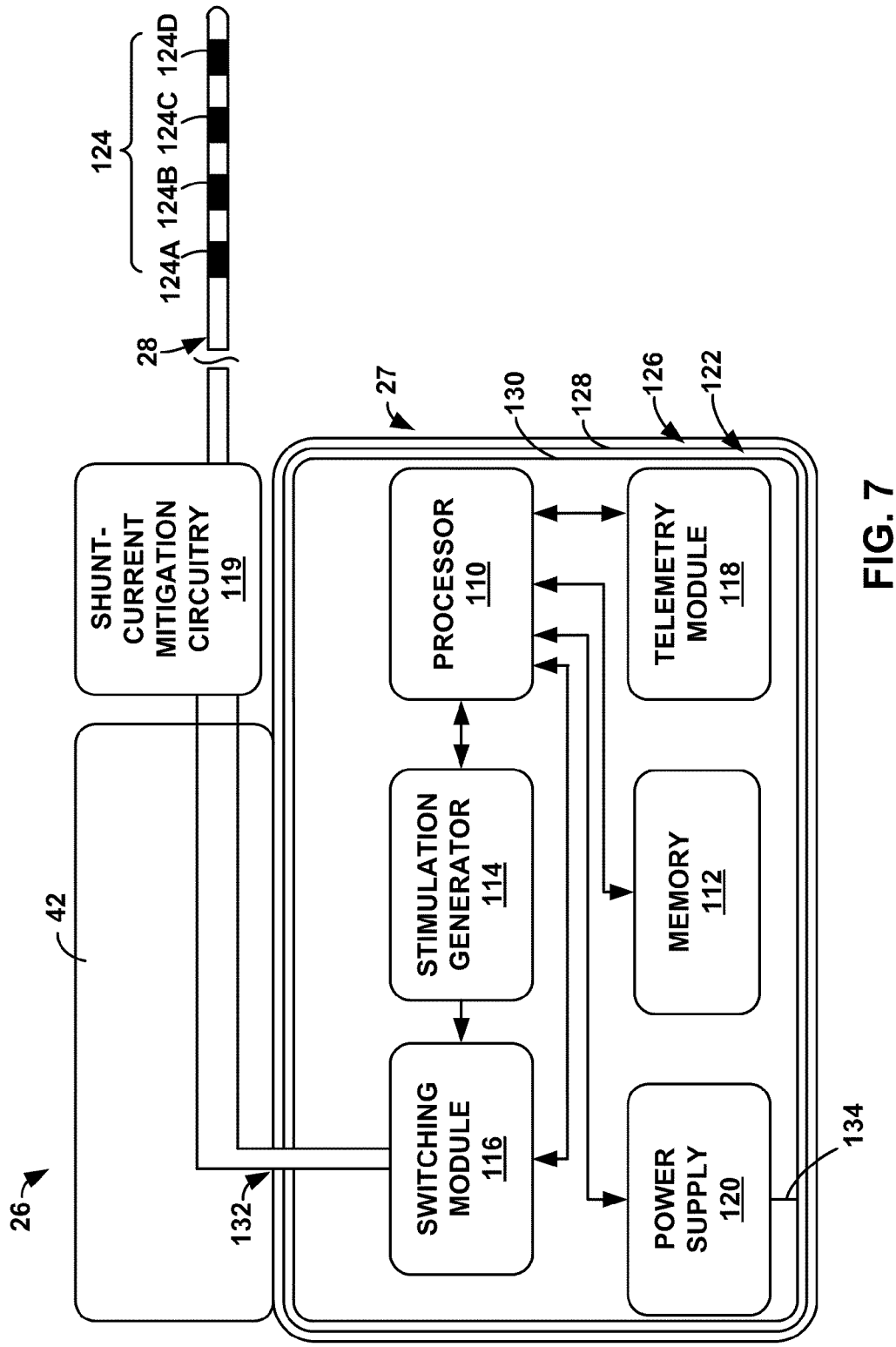
FIG. 7 is a functional block diagram of an example INS that generates and delivers electrical stimulation signals to a target tissue site other than a heart of a patient.

FIG. 7 is a functional block diagram of an example INS 26. INS 26 includes processor 110, memory 112, stimulation generator 114, switching module 116, telemetry module 118, and power source 120. In the example shown in FIG. 7, processor 110, memory 112, stimulation generator 114, switching module 116, telemetry module 118, and power source 120 are enclosed within housing 27, which may be, for example a hermetic housing.

As shown in FIG. 7, stimulation generator 114 is electrically coupled to lead 28 via shunt-current mitigation circuitry 119. Shunt-current mitigation circuitry 119 may be coupled to lead 28 either directly or indirectly (e.g., via a lead extension). Alternatively, shunt-current mitigation circuitry 119 may be coupled more than one lead directly or indirectly (e.g., via a lead extension, such as a bifurcating lead extension that may electrically and mechanically couple to two leads) as needed to provide neurostimulation therapy to patient 12. In some examples, a lead body of lead 28 may comprise shunt-current mitigation circuitry 119. Although FIG. 7 illustrates an example in which shunt-current mitigation circuitry 119 is external to housing 27, e.g., external to INS 26, aspects of this disclosure are not so limited. In some examples, shunt-current mitigation circuitry 119 may be enclosed within housing 27 and electrically coupled to stimulation generator 114. In some examples, a connector, e.g. connector 42 (FIG. 1), coupled to INS 26 that is used to electrically and mechanically connect lead 28 to stimulation generator may comprise shunt-mitigation circuitry 119.

In the example illustrated in FIG. 7, lead 28 includes electrodes 124A-124D (collectively referred to as "electrodes 124"). Electrodes 124 may comprise ring electrodes. In other examples, electrodes 124 may be partial-ring or sectional electrodes arranged in a complex electrode array that includes multiple non-contiguous electrodes at different angular positions about the outer circumference of lead 28, as well as different levels of electrodes spaced along a longitudinal axis of lead 28. The configuration, type, and number of electrodes 124 illustrated in FIG. 7 are merely exemplary. In other examples, INS 26 may be coupled to any suitable number of leads with any suitable number and configuration of electrodes. Moreover, lead 28 may comprise a shape other than a cylindrical shape. As an example, lead 28 may comprise a paddle-shaped portion that carries electrodes 124. In some examples, housing 27 of INS 26 may also include one or more electrodes.

Each of the electrodes 124 may be electrically coupled to the stimulation generator 114 via shunt-current mitigation circuitry 119. That is, shunt-current mitigation circuitry 119 is located between stimulation generator 114 and electrodes 124. In general, shunt-current mitigation circuitry 119 may help limit the passage of shunt-current through an electrical path including electrodes 124, conductors within lead 28, and stimulation generator 114. In examples in which INS 26 includes a sensing module (not shown in FIG. 7) for sensing one or more physiological parameters of patient 12 (e.g., ECG signals) via electrodes 124, shunt-current mitigation circuitry 119 may be electrically coupled to the sensing module and electrodes 124.

As previously discussed, the delivery of cardiac rhythm therapy to heart 14 of patient 12 by ICD 16 may generate a voltage gradient in the patient's body. This voltage gradient may generate a flow of shunt-current through an electrical path including electrodes 124, 125 or housing 27. Shunt-current mitigation circuitry 119 may reduce the shunt-current that flows through the electrical path by increasing the impedance of the electrical path including electrodes 124. In this way, the shunt-current mitigation circuitry may reduce the current at the interface between electrodes 124 and tissue, which may help prevent the inadvertent stimulation of tissue that may be disposed between ICD 16 and electrodes 124 by, for example, decreasing the possibility that current with the ability to stimulate tissue (e.g., because of the amplitude of the current) may flow through the tissue. This may help prevent the inadvertent stimulation of tissue that is not intended to be stimulated.

Examples of shunt-current mitigation circuitry 119 include, but are not limited to, a resistor, a resistive wire, a switch, an inductor, and a monitor coupled to the switch that monitors one or more electrical parameter values at electrodes 124. Examples of shunt-mitigation circuitry 119 are described in further detail with respect to FIGS. 15-20. As described in more detail with respect to FIG. 15, shunt-current mitigation circuitry 119 may comprise a plurality of resistors and/or resistive wires. The resistors and/or resistive wires provide a high impedance path for the shunt-current. The resistors and/or resistive wires provide a high impedance path for the shunt-current thereby reducing the amount of shunt-current that may flow through electrodes 124 into circuitry within INS 26. As described with respect to FIG. 16, shunt-current mitigation circuitry 119 may comprise a plurality of inductors, which may provide a high impedance path for the shunt-current. As described with respect to FIG. 17, shunt-mitigation circuitry 119 may comprise a plurality of diodes, such as transient absorber diodes, Zener diodes, or high voltage diodes. The diodes may allow current to flow in one direction, and limit the amount of current that may flow in the opposite direction. In some examples, the diodes are leaky diodes that may allow a certain amount of current to leak through so that the charge on the electrodes is balanced. A leaky diode may be realized, in some examples, by using a non-leaky regular diode connected in parallel with a high impedance resistor, e.g., about 1 mega-ohm to 100 mega-ohms.

Figure 18:
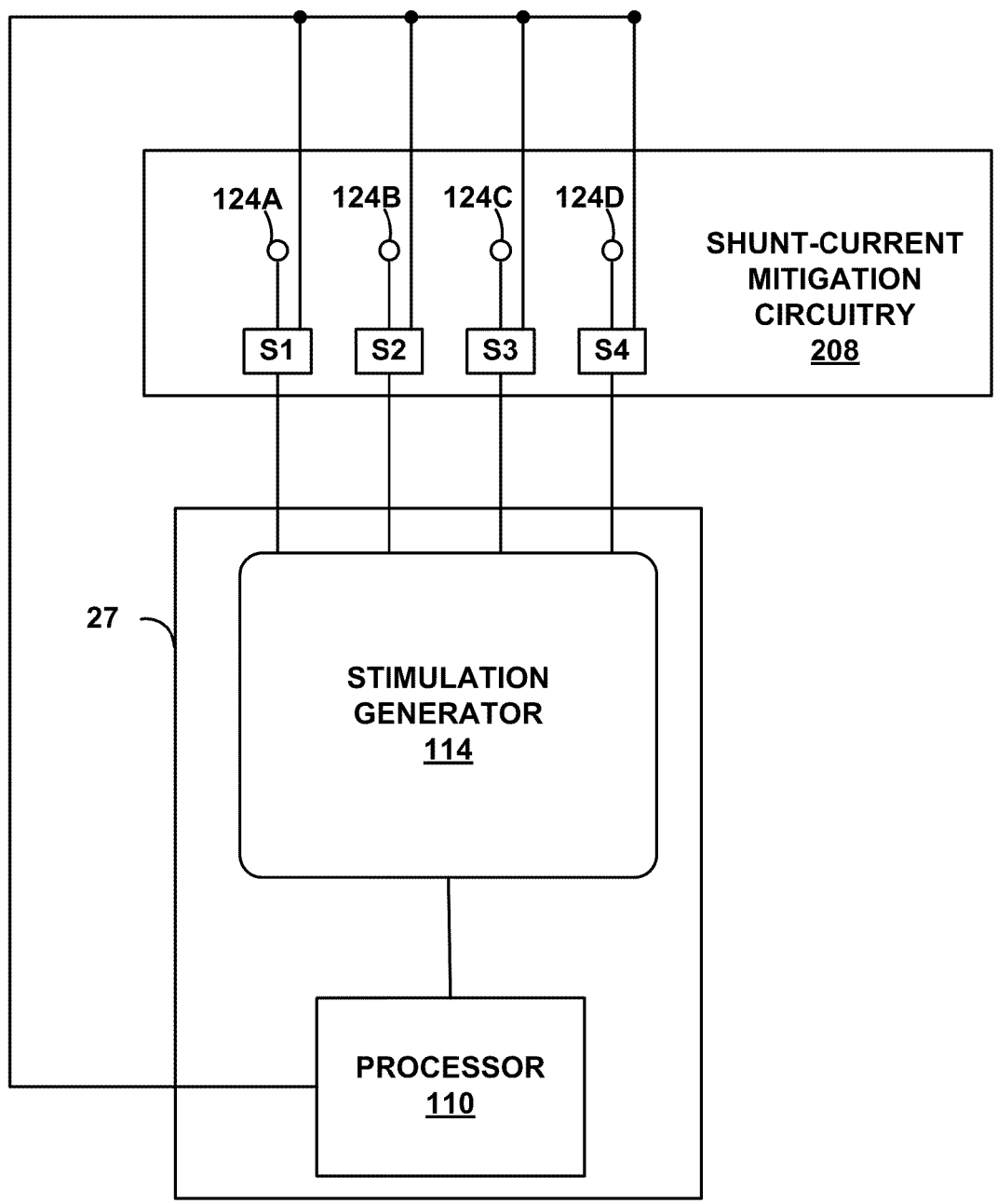
FIG. 18 is a block diagram illustrating another example IMD that includes shunt-current mitigation components.

As described with respect to FIG. 18, shunt-current mitigation circuitry 119 may comprise a plurality of switches that toggle open to generate a high impedance path for the shunt-current, thereby reducing the amount of shunt-current that may flow through electrodes 124 into circuitry within INS 26. The switches may be opened in response to receiving a communication signal from ICD 16 (FIG. 1) indicative of prospective therapy delivery by ICD 16. As described in more detail with respect to FIG. 19, shunt-current mitigation circuitry 119 may also comprise a plurality of switches and one or more monitors. The monitors may monitor a voltage or current at electrodes 124. If the voltage or current exceeds a threshold value, the switches may toggle open to create a high impedance path for the shunt-current, thereby reducing the amount of shunt-current that may flow through electrodes 124 into circuitry within INS 26. In addition, using multiple switches connected in series, and in some examples with resistors across each switch, may increase the ability to switch at higher voltages. As described in more detail with respect to FIG. 20, shunt-current mitigation circuitry 119 may also comprise a plurality of current limiters such as fuses, bimetallic circuit breakers, and the like. Current limiters may limit the amount of current that may flow through electrodes 124. Accordingly, if the shunt-current is greater than the limit of the current limiters, the current limiters may limit the amount of shunt-current that may flow from electrodes 124.

Memory 112 includes computer-readable instructions that, when executed by processor 110, cause INS 26 to perform various functions described herein. Memory 112 may include any volatile, non-volatile, magnetic, optical, or electrical media, such as a RAM, ROM, NVRAM, EEPROM, flash memory, or any other digital media. Memory 112 may store therapy programs, which may be stored in therapy program groups, and operating instructions. The therapy programs may define a particular program of therapy in terms of respective values for electrical stimulation parameters, such as electrode combination, electrode polarity, current or voltage amplitude, pulse width and pulse rate. A program group may comprise a plurality of therapy programs that may be delivered together on an overlapping or non-overlapping basis. The stored operating instructions may guide the general operation of INS 26 under control of processor 110, and may include instructions for measuring the impedance of electrodes 124.

Stimulation generator 114 generates stimulation signals, which may be pulses as primarily described herein, or continuous time signals, such as sine waves, for delivery to patient 12 via selected combinations of electrodes 124. Processor 110 controls stimulation generator 114 according to stored therapy programs and/or program groups in memory 112 to apply particular stimulation parameter values specified by one or more of programs, such as amplitude, pulse width, and pulse rate. Processor 110 may include any one or more microprocessors, controllers, a DSPs, ASICs, FPGAs, or equivalent discrete or integrated digital or analog logic circuitry, and the functions attributed to processor 110 herein may be embodied as software, firmware, hardware or any combination thereof.

Processor 110 may also control switching module 116 to apply the stimulation signals generated by stimulation generator 114 to selected combinations of electrodes 124. In particular, switching module 116 couples stimulation signals to selected conductors within leads 28 which, in turn, deliver the stimulation signals across selected electrodes 124. Switching module 116 may include a switch array, switch matrix, multiplexer, or any other type of switching device suitable to selectively couple stimulation energy to selected electrodes. Hence, stimulation generator 114 is coupled to electrodes 124 via switching module 116 and conductors within leads 28. In some examples, INS 26 does not include switching module 116.

Stimulation generator 114 may be a single or multi-channel stimulation generator. In particular, stimulation generator 114 may be capable of delivering a single stimulation pulse, multiple stimulation pulses, or a continuous signal at a given time via a single electrode combination or multiple stimulation pulses at a given time via multiple electrode combinations. In some examples, however, stimulation generator 114 and switching module 116 may be configured to deliver multiple channels on a time-interleaved basis. In this case, switching module 116 serves to time division multiplex the output of stimulation generator 114 across different electrode combinations at different times to deliver multiple programs or channels of stimulation energy to patient 12. In some examples, stimulation generator 114 may be electrically coupled either directly (e.g., by a wire) or indirectly (e.g., capacitive coupling) to electrically conductive layer 122 of housing 27.

Telemetry module 118 supports wireless communication between INS 26 and an external programmer 24 (FIG. 1) or another computing device, as well as between INS 26 and ICD 16 under the control of processor 110. Processor 110 of INS 26 may receive, as updates to programs, values for various stimulation parameters such as amplitude and electrode combination, from programmer 24 via telemetry module 118. The updates to the therapy programs may be stored within memory 112. Furthermore, in some examples, INS 26 may receive a signal directly from ICD 16 via telemetry module 118, whereby the signal may indicate prospective therapy delivery by ICD 16, e.g., when ICD is about to transmit a stimulation signal. In some examples, INS 26 may receive signals from ICD 16 via programmer 24. For example, ICD 16 may transmit a signal to programmer 24, and programmer 24 may transmit the signal to INS 26. INS 26 may receive the signal from programmer 24 via telemetry module 118. Telemetry module 118 may provide such information to processor 110. In response, processor 110 may toggle switches within the shunt-current mitigation circuitry 119 to an open position so that the shunt-current flowing into stimulation generator 114 of INS 26 is reduced or even eliminated.

The various components of INS 26 are coupled to power supply 120, which may include a rechargeable or non-rechargeable battery. A non-rechargeable battery may be selected to last for several years, while a rechargeable battery may be inductively charged from an external device, e.g., on a daily or weekly basis. In other examples, power supply 120 may be powered by proximal inductive interaction with an external power supply carried by patient 12. In some examples, as illustrated in FIG. 7, power supply 120 or another component of INS 26 may be electrically coupled to electrically conductive layer 122 by a wire 134 or other conductive element.

In the example shown in FIG. 7, outer housing 27 of INS 26 comprises an electrically conductive layer 122 and an electrically insulative layer 126 substantially fully encapsulating electrically conductive layer 122. In this way, electrically insulative layer 126 substantially fully electrically insulates electrically conductive portions of housing 27 that may contact tissue of patient 12 when INS 26 is implanted within patient 12. Electrically conductive layer 122 may comprise, for example, a metal, such as titanium, stainless steel, or the like. In some examples, electrically conductive layer 122 may be more electrically conductive, i.e., have a lower electrical impedance, than surrounding tissue of patient 12. In the absence of electrically insulative layer 126, this lower impedance may result in shunt-current flowing to housing 27 and lead electrodes of INS 26 from electrodes carried by, for example, leads 18, 20, 22 (FIG. 3) connected to ICD 16. As described above, this shunt-current may result in undesirable physiological effects to patient 12, including, for example, stress to tissue adjacent to housing 27 or unintended stimulation of tissue adjacent to housing 27. In some examples, the shunt-current also may interfere with operation of components of INS 26, such as sensing circuitry or stimulation circuitry.

In some examples, as shown in FIG. 7, electrically insulative layer 126 may substantially fully cover or encapsulate an external surface 128 of electrically conductive layer 122. In other examples, electrically insulative layer 126 may substantially fully cover or line an internal surface 130 of conductive layer 122, or housing 27 may include a first electrically insulative layer that covers external surface 128 and a second electrically insulative layer that covers internal surface 130. Substantially fully covering either external surface 128, internal surface 130, or both of electrically conductive layer 122 may more effectively mitigate or substantially eliminate shunt-current from interfering with operation of INS 26 compared to partially covering a surface 128 or 130 of conductive layer 122. For example, in cases in which housing 27 does not include an electrically insulative layer 126 that fully encapsulates or lines a surface 128, 130 of electrically conductive layer 122, the shunt-current may result in undesirable unintentional physiological effects to patient 12, may interfere with operation of INS 26, and may even minimize the intensity of stimulation delivered to heart 14 of patient 12 by ICD 16.

Even in cases in which outer housing 27 includes electrically conductive layer 122 and an electrically insulative layer that partially encapsulates or lines either outer surface 128 or inner surface 130 of electrically conductive layer 122, the shunt-current may interfere with operation of INS 26 because a conductive path remains from electrodes carried by leads 18, 20, 22 to housing 27 and components (e.g., stimulation generator 114 or processor 110) of INS 26 within housing 27. Moreover, a housing 27 that includes electrically conductive layer 122 and an electrically insulative layer that partially, but not fully, encapsulates electrically conductive layer 122 may increase the current of the shunt-current at the interface of electrically conductive layer 122 and tissue of patient 12. This increased current may result in undesired stimulation to the tissue adjacent to the electrically conductive layer 122 or stress the adjacent tissue. Hence, an electrically insulative layer 126 that substantially fully encapsulates external surface 128 of electrically conductive layer 122, substantially fully lines internal surface 130 of electrically conductive layer 122, or both, may more effectively mitigate or substantially eliminate shunt-current from undesirably affecting operation of INS 26 or tissue of patient 12 adjacent to housing 27.

As described above with respect to FIG. 1, electrically insulative layer 126 may substantially fully cover or substantially fully encapsulate conductive layer 122, and INS 26 may include a separate connector block 42. However, in other examples, electrically insulative layer 126 may at least partially cover or encapsulate connector block 42, in addition to substantially fully encapsulating conductive layer 122 of housing 27. In some examples, electrically insulative layer 126 may substantially fully cover connector block 42 in addition to substantially fully covering conductive layer 122 of housing 27.

Electrically insulative layer 126 may define an aperture 132 that allows conductors extending from connector block 42 to pass through an aperture or feedthrough in housing 27 and couple to conductors in lead 28 components therein, such as switching module 116. In other examples, electrically insulative layer 126 may substantially fully cover housing 27 and connector block 42, and may define an aperture that allows at least one conductor within lead 28 to pass through and couple to a conductor within connector block 42.

In examples in which electrically conductive layer 122 only forms a part of housing 27, insulative layer 126 may only encapsulate the electrically conductive portions of housing 27, including electrically conductive layer 122. However, in other examples, electrically insulative layer 126 can insulate the entire exterior surface of outer housing 27.

In some examples, electrically insulative layer 126 may include an electrically insulative metal oxide, an electrically insulative metal nitride, an electrically insulative ceramic, or an electrically insulative sintered material. For example, the electrically insulative layer of housing 27 may include aluminum oxide ($Al_2O_3$), silicon dioxide ($SiO_2$), silicon nitride ($Si_3N_4$), aluminum nitride (AlN), glass, porcelain, diamond, or titanium dioxide ($TiO_2$). In some examples, electrically insulative layer 126 may be formed by oxidation of the material from which electrically conductive layer 122 is formed (e.g., oxidation of titanium to form titanium dioxide). In other examples, electrically insulative layer 126 may be formed on or otherwise deposited on electrically conductive layer 122 by ion-beam deposition, sputtering, or another atomic or molecular treatment.

As another example, electrically insulative layer 126 may include an electrically insulative plastic or polymer. The electrically insulative plastic or polymer may include, for example, silicone, polyethylene, cross-linked polyethylene, parylene, polyimide, epoxy, polyurethane, polyvinylchloride (PVC), rubber-like polymers, polytetrafluoroethylene (PTFE), ethylene tetrafluoroehtylene (ETFE), polycarbonate, a biocompatible thermoplastic, or the like. One example of a suitable silicone is available under the trade designation Silastic® Medical Adhesive Silicone, Type A, from Dow Corning, Midland, Mich. An example of a suitable polycarbonate is available under the trade designation Lexan HPM, from SABIC Innovative Plastics, Pittsfield, Mass. An example of a biocompatible thermoplastic is available under the trade designation PEEK-OPTIMA from Invibio, Inc., West Conshohocken, Pa. In some examples, the electrically insulative plastic or polymer may be applied to electrically conductive layer 122 by molding, dip coating, a laser treatment, etching treatment, or the like.

Electrically insulative layer 126 may comprise a range of thicknesses, and in some examples may comprise a thickness of approximately 2.54 micrometers (0.1 mils) to approximately 1016 micrometers (40 mils), or may comprise a thickness of approximately 254 micrometers (10 mils) to approximately 508 micrometers (20 mils). In other examples, electrically insulative layer 126 may comprise a thickness less than approximately 2.54 micrometers (0.1 mils) or greater than approximately 1016 micrometers.

Although not shown in FIG. 7, housing 27 may comprise more than two layers. For example, housing 27 may comprise electrically conductive layer 122, a second layer formed over internal surface 130 or external surface 128, and a third layer formed over the second layer, such that the second layer is positioned between the electrically conductive layer 122 and the third layer. In some examples, the second and third layers may comprise a respective one of the electrically insulative layers described above. For example, the second layer may comprise an electrically insulative metal oxide, electrically insulative metal nitride, electrically insulative ceramic, or electrically insulative sintered material, and the third layer may comprise an electrically insulative plastic or polymer. In other examples, the second layer may comprise a first electrically insulative metal oxide, electrically insulative metal nitride, electrically insulative ceramic, or electrically insulative sintered material, and the third layer may comprise a second electrically insulative metal oxide, electrically insulative metal nitride, electrically insulative ceramic, or electrically insulative sintered material. In some examples, the second layer may comprise an electrically insulative material, while the third layer comprises a material that provides another type of protection to the components of INS 26 or housing 27, such as, for example, chemical protection, physical protection, or the like. In other examples, the second layer may comprise a material that provides chemical protection, physical protection, or the like to components of INS 26 or housing 27, and the third layer may comprise an electrically insulative material. In some examples, the second layer may be metallic, and may comprise, for example, a metal coating, a metal film, metal stamping, metal enclosure, or metal shield.

In some examples, housing 27 comprises one or more additional layers, which may be formed over the third layer. Each of the additional layers may comprise the same material as one of the second and third layers, or may comprise a different material. In some examples, one or more of the additional layers may provide physical protection to the other layers of housing 27. One or more of the additional layers also may electrically insulate the other layers of housing 27.

In some examples, housing 27 comprises one or more layers substantially fully covering external surface 128 and one or more layers substantially fully covering internal surface 130. For example, housing 27 may comprise a first electrically insulative layer that substantially fully covers the external surface of electrically conductive layer 122 and a second electrically insulative layer that substantially fully covers the internal surface of electrically conductive layer 122. In some examples, the first and second electrically insulative layers may comprise the same material, while in other examples, the first and second electrically insulative layers may comprise different materials. Further, housing 27 may include additional layers formed over one or both of the first and second electrically insulative layers.

In some examples, housing 27 includes an electrically insulative spacer between two adjacent layers, e.g., an inner layer and an outer layer. An example of an electrically insulative spacer is described with respect to FIG. 13. The electrically insulative spacer may be disposed between any two adjacent layers, and may electrically insulate the inner layer from the outer layer. For example, housing 27 may comprise an electrically conductive inner layer and a metallic outer layer, which also may be electrically conductive. In examples such as these, housing 27 may comprise an electrically insulative spacer between the electrically conductive inner layer and the metallic outer layer. In some examples, the electrically insulative spacer may comprise a sleeve or other preformed object that fits around the electrically conductive inner layer, e.g., into which the electrically conductive inner layer is fitted. The electrically insulative spacer then may be attached to the inner layer by, for example, an adhesive or a heat treatment. Continuing the example, the outer layer then may be deposited over the insulative spacer. In other examples, the electrically insulative spacer layer may be deposited over the electrically conductive inner layer by ion-beam deposition, sputtering, another atomic or molecular treatment, molding, or the like. The electrically insulative spacer layer may comprise, for example, a polymer, plastic, electrically insulative metal oxide, electrically insulative metal nitride, electrically insulative ceramic, or electrically insulative sintered material, including any materials described above.

Although not shown in FIG. 7, in some examples, instead of or in addition to a housing 27 comprising an electrically insulative layer or an electrically insulative spacer, INS 26 may comprise an electrically insulative pouch that substantially fully encapsulates housing 27. An example of an electrically insulative pouch is described with respect to FIG. 14. Similar to a housing 27 that includes an electrically insulative layer 126, the electrically insulative pouch that substantially surrounds an outer surface of medical device housing 27 may mitigate or substantially eliminate shunt-current from flowing from electrodes carried by leads 18, 20, 22 connected to ICD 16 to housing 27 of INS 26.

The electrically insulative pouch may comprise, for example, a preformed covering into which housing 27 of INS 26 fits. As discussed above, the pouch may be separate from housing 27 and configured (e.g., shaped and sized) to receive housing 27. In some examples, the electrically insulative pouch may comprise a size and/or shape that substantially conforms to the size and/or shape of housing 27, so that the pouch forms an intimate fit with housing 27. For example, the electrically insulative pouch may be sized and/or shaped to form a friction fit with one or more surfaces of housing 27. In other examples, the electrically insulative pouch may comprise a size and/or shape that does not substantially conform to the size and/or shape of housing 27. For example, the electrically insulative pouch may be sized larger than housing 27, so that there is not a friction fit between the pouch and housing 27, and the pouch fits more loosely around housing 27.

The electrically insulative pouch may substantially fully enclose or encapsulate housing 27, and may not encapsulate connector block 42. In some examples, the electrically insulative pouch may at least partially encapsulate connector block 42, in addition to substantially fully encapsulating housing 27. In some examples, the electrically insulative pouch may substantially fully encapsulate connector block 42 in addition to substantially fully encapsulating housing 27. The electrically insulative pouch may define an aperture that allows conductors extending from connector block 42 to pass through an aperture or feedthrough into housing 27 and couple to components (e.g., stimulation generator 114, switching module 116, processor 110, and the like) therein. As another example, the electrically insulative pouch may substantially fully cover housing 27 and connector block 42, and may define an aperture which allows at least one conductor within lead 28 to pass through and couple to a conductor within connector block 42. In this way, the electrically insulative pouch may mitigate or substantially prevent shunt-current from traveling from electrodes carried by leads 18, 20, 22 connected to ICD 16 to housing 27 of INS 26. As discussed above, the insulative pouch may comprise a single piece of material or two or more pieces of material that are coupled to each other and, optionally, to housing 27.

In some examples, the electrically insulative pouch is disposed inside of housing 27 and encapsulates components housed by (e.g., enclosed by) housing 27, such as, for example, electrical circuitry and/or wiring. In some cases, the electrical circuitry and/or wiring may not be electrically connected to housing 27, and the electrically insulative pouch electrical insulates the circuitry and/or wiring from housing 27. In this way, the electrically insulative pouch may eliminate any direct electrical connection between the circuitry and or/wiring and housing 27, and may reduce any capacitive or inductive electrical coupling between the circuitry and wiring and housing 27. In some examples, INS 26 includes an electrically insulative layer or electrically insulative pouch that substantially fully covers or encapsulates an outer surface of housing 27 in addition to an electrically insulative pouch that encapsulates components housed in housing 27. In other example, INS 26 may not include an electrically insulative layer or electrically insulative pouch that substantially fully covers or encapsulates an outer surface of housing 27 in addition to an electrically insulative pouch that encapsulates components housed in housing 27.

The electrically insulative pouch may comprise, for example, a biocompatible polymer or plastic, which may or may not be flexible. In some examples, the electrically insulative pouch may comprise at least one of silicone, polyethylene, cross-linked polyethylene, parylene, polyimide, epoxy, polyurethane, polyvinylchloride (PVC), rubber-like polymers, polytetrafluoroethylene (PTFE), ethylene tetrafluoroehtylene (ETFE), polycarbonate, a biocompatible thermoplastic, or the like. The electrically insulative pouch may comprise a thickness of about 25.4 micrometers (about 0.001 inches) to a thickness of about 1016 micrometers (about 0.040 inches), or about 254 micrometers (about 0.01 inches) to a thickness of about 508 micrometers (about 0.02 inches). In other examples, the electrically insulative pouch may comprise a thickness of about 0.102 centimeters (about 0.04 inches) to about 0.508 centimeters (about 0.2 inches).

The electrically insulative pouch may be assembled around housing 27 by a manufacturer of INS 26 at the time of manufacture or prior to shipping INS 26 to a wholesaler or implanting physician, or may be assembled by the implanting physician at or before the time at which INS 26 is implanted in patient 12. In some examples, the implanting physician may determine whether INS 26 would benefit from an electrically insulative pouch at or before the time of implant, and may or may not assembled the pouch around housing 27 depending on his or her determination. For example, the implanting physician may consider the implant location of INS 26, ICD 16, and any leads coupled to INS 26 or ICD 16 when determining whether INS 26 would benefit from an electrically insulative pouch. When the implanting physician determines that INS 26 would benefit from an electrically insulative pouch, the physician or a technician may then assemble the electrically insulative pouch around housing 27 of INS 26.

Figure 8:
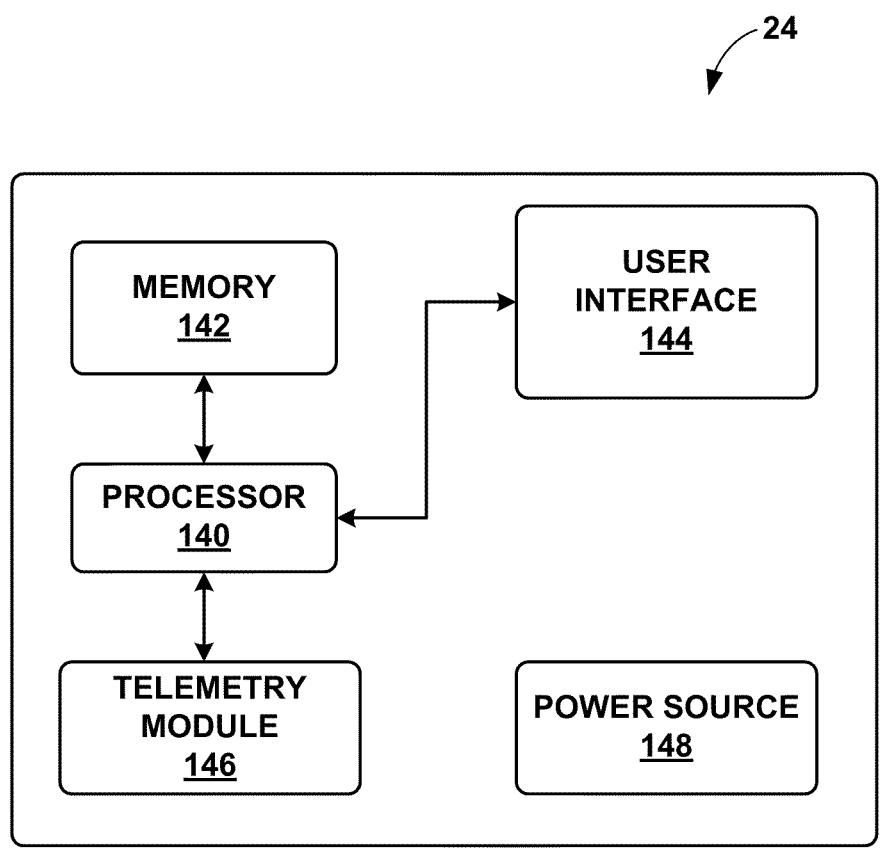
FIG. 8 is a functional block diagram of an example medical device programmer.

FIG. 8 is block diagram of an example programmer 24. As shown in FIG. 8, programmer 24 includes processor 140, memory 142, user interface 144, telemetry module 146, and power source 148. Programmer 24 may be a dedicated hardware device with dedicated software for programming of ICD 16 and INS 26. Alternatively, programmer 24 may be an off-the-shelf computing device running an application that enables programmer 24 to program ICD 16 and INS 26. In some examples, separate programmers may be used to program ICD 16 and INS 26. However, a common programmer 24 that is configured to program both ICD 16 and INS 26 may provide a more streamlined programming process for a user, such as a clinician or patient 12.

A user may use programmer 24 to select therapy programs (e.g., sets of stimulation parameters), generate new therapy programs, modify therapy programs through individual or global adjustments or transmit the new programs to a medical device, such as ICD 16 or INS 26 (FIG. 1). The clinician may interact with programmer 24 via user interface 144, which may include a display to present graphical user interface to a user, and a keypad or another mechanism for receiving input from a user.

Processor 140 can take the form one or more microprocessors, DSPs, ASICs, FPGAs, programmable logic circuitry, or the like, and the functions attributed to processor 140 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein.

Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by ICD 16 and INS 26, such as stimulation parameter values.

Programmer 24 may communicate wirelessly with ICD 16 and INS 24, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 14, as described above with reference to FIG. 1. Telemetry module 146 may be similar to telemetry module 98 of ICD 16 (FIG. 6) or telemetry module 118 of INS 26 (FIG. 7).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 148 delivers operating power to the components of programmer 24. Power source 148 may include a battery and a power generation circuit to produce the operating power. In some examples, the battery may be rechargeable to allow extended operation. Recharging may be accomplished by electrically coupling power source 148 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 148 may include circuitry to monitor power remaining within a battery. In this manner, user interface 144 may provide a current battery level indicator or low battery level indicator when the battery needs to be replaced or recharged. In some cases, power source 148 may be capable of estimating the remaining time of operation using the current battery.

Figure 9:
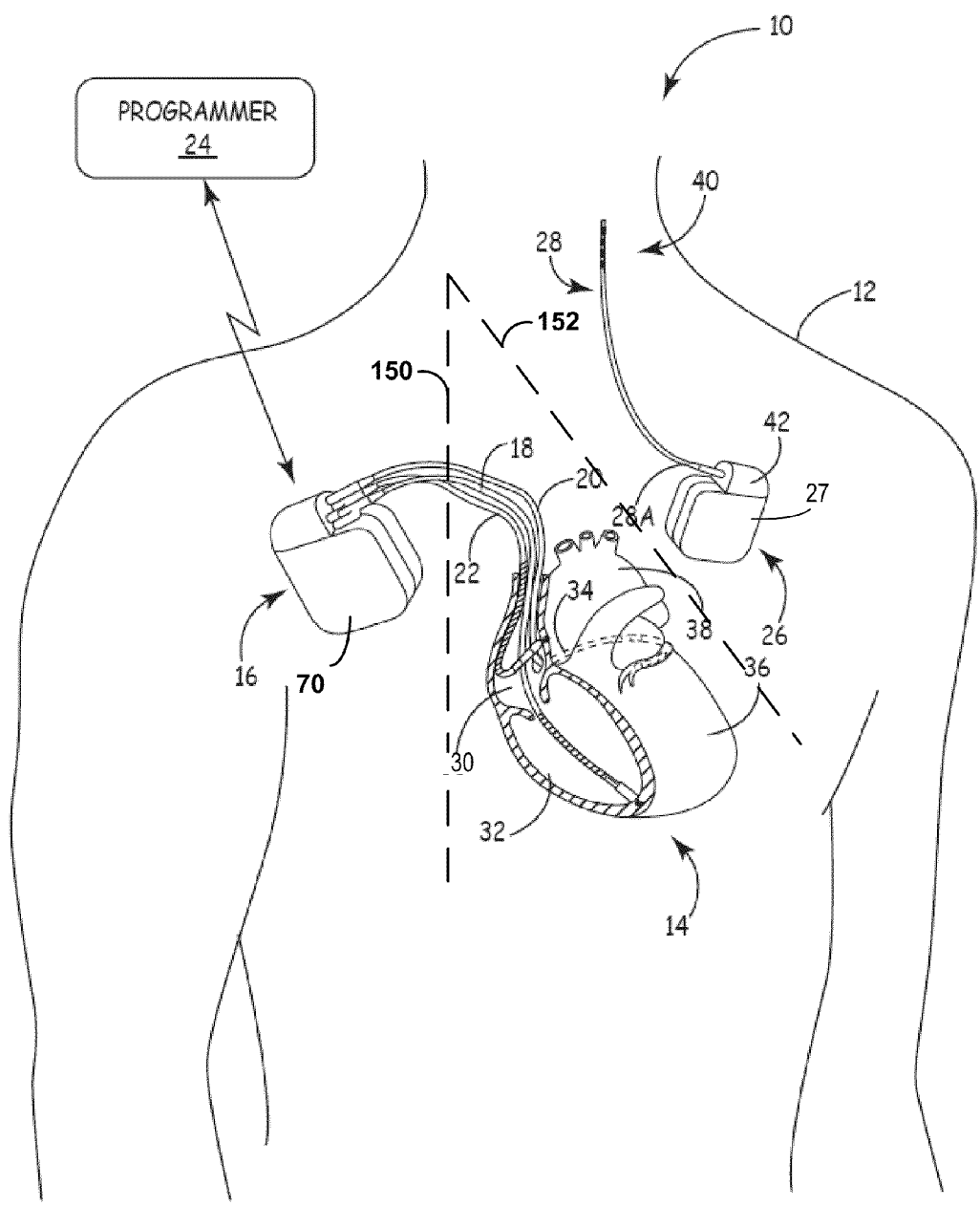
FIG. 9 is a conceptual diagram illustrating an example placement of the ICD and INS within a patient.

In some cases, the placement of ICD 16 and INS 26 relative to each other within patient 12 may help reduce the amount of shunt-current that flows through electrodes 124 (FIG. 7) and into INS 26. For example, the shunt-current to INS 26 from ICD 16 may be reduced by placing INS 26 and lead 28 substantially outside of the current path generated by the delivery of stimulation by ICD 16 (e.g., as far from ICD 16 and leads 18, 20, 22 as feasible). FIG. 9 is a conceptual diagram that helps illustrate this concept. FIG. 9 is substantially similar to FIG. 1 but illustrates marker lines 150, 152.

As FIG. 9 illustrates, shunt-current to INS 26 may be mitigated by placing INS 26 such that electrodes 124 of lead 28 are not positioned between housing 70 of ICD 16 and electrodes 50, 52, 54, 56, 58, 60, 68, 72, 74, and 76 of leads 18, 20, and 22, or, specifically between housing 70 and electrodes 68, 72, 74, 76 that may be used to deliver a cardioversion or defibrillation shock to heart 14. In some applications, such as, for example, lower back pain stimulation, sacral nerve stimulation, or deep brain stimulation, INS 26 and lead 28 may be able to be positioned sufficiently far from ICD 16 and leads 18, 20, 22 such that there is little or no chance of shunt-current interfering with operation of INS 26. In other applications, such as, for example, upper back or cervical pain stimulation, a relatively higher risk of shunt-current may be present due to proximity of INS 26 and/or lead 28 and ICD 16 and leads 18, 20, 22.

In the example shown in FIG. 9, the current path of the stimulation signal delivered by ICD 16 is between marker line 150 and marker line 152 (e.g., the space including heart 14), and INS 26 is outside the current path of the stimulation signal, e.g., outside of the area marked by marker line 150 and 152. Marker lines 140 and 142 are a two dimensional representation of marker lines for purposes of illustrations. In some examples, housing 27 of INS 26 maybe positioned between lines 150, 152, while electrodes 124 may remain outside of the current path, e.g., outside of the spaced defined between lines 150, 152. During implantation of INS 26 and lead 28 within patient 12, the clinician may determine the approximate current path of the stimulation delivered by ICD 16 based on the stimulation parameter values, such as the number of electrodes and their respective implant locations, the amplitude or energy of the stimulation, as well as the known characteristics of tissue proximate leads 18, 20, 22 and housing 70.

INS 26 may be located on either marker 142 or within about 2.5 to 10.2 centimeters on either side of marker 142. ICD 16 may be within the area marked by markers 150 and 152. By placing INS 26 outside of the stimulation current path of ICD 16 the shunt-current may be reduced or eliminated because no stimulation current may feed into INS 26.

Figure 10:
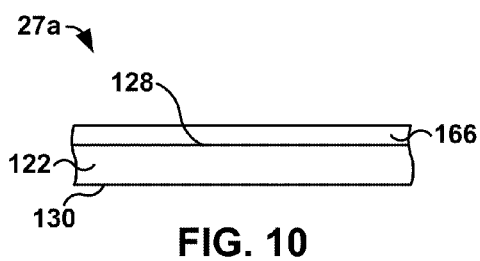
FIG. 10 is a schematic cross-sectional diagram illustrating an example medical device housing that includes an electrically conductive layer and an electrically insulative layer formed over an external surface of the electrically conductive layer.

FIG. 10 is a schematic cross-sectional diagram illustrating an example medical device outer housing 27a that includes electrically conductive layer 122 and electrically insulative layer 166 formed over an exterior surface 128 of electrically conductive layer 122. The exterior surface of electrically conductive layer 122 may be the surface opposite the surface facing the interior of housing 27a, which encloses operative components of INS 26 (e.g., a processor, stimulation generator, and the like). Housing 27a may be an example of housing 27 (FIG. 7) of INS 26. Electrically insulative layer 166 may substantially fully cover or encapsulate exterior surface 128 of housing 27a or at least the electrically conductive portions of housing 27a, which may be defined by electrically conductive layer 122 alone or electrically conductive layer 122 and other portions of housing 27. As discussed above with respect to FIG. 7, electrically conductive layer 122 may comprise, for example, a biocompatible metal, such as titanium, stainless steel, or the like.

In some examples, implantation of INS 26 including outer housing 27a with electrically conductive layer 122 may result in shunt-current flowing to housing 27a from electrodes carried by, for example, leads 18, 20, 22 connected to ICD 16. As described above, this shunt-current may result in undesirable physiological effects to patient 12, including, for example, unintended stimulation of tissue adjacent to housing 27a. In some examples, the shunt-current also may interfere with operation of components of INS 26, such as sensing circuitry or stimulation circuitry, may reduce the current provided by the electrodes carried by leads 18, 20, 22 to the desired cardiac therapy site, or both.

Electrically insulative layer 166 may comprise an electrically insulative material that increases the effective impedance of housing 27a and decreases the amount of shunt-current that flows through housing 27a, or may even substantially eliminate shunt-current from flowing through housing 27a. In some examples, the electrically insulative layer 166 may increase the impedance of housing 27a to such an extent that the impedance of housing 27a is greater than the impedance of tissue surrounding housing 27a, so that electrical current encounters less resistance flowing through the tissue than through housing 27a.

In some examples, electrically insulative layer 166 may comprise an electrically insulative metal oxide, an electrically insulative metal nitride, an electrically insulative ceramic, or an electrically insulative sintered material. For example, the electrically insulative layer of housing 27 may include aluminum oxide ($Al_2O_3$), silicon dioxide ($SiO_2$), silicon nitride ($Si_3N_4$), aluminum nitride (AlN), glass, porcelain, diamond, or titanium dioxide ($TiO_2$). In some examples, electrically insulative layer 166 may be formed by oxidation of the material from which electrically conductive layer 122 is formed (e.g., oxidation of titanium to form titanium dioxide). In other examples, electrically insulative layer 166 may be formed on or otherwise deposited onto electrically conductive layer 122 by ion-beam deposition, sputtering, or another atomic or molecular treatment.

In other examples, electrically insulative layer 166 may comprise an electrically insulative plastic or polymer. The electrically insulative plastic or polymer may include, for example, silicone, polyethylene, cross-linked polyethylene, parylene, polyimide, epoxy, polyurethane, polyvinylchloride (PVC), rubber-like polymers, polytetrafluoroethylene (PTFE), ethylene tetrafluoroehtylene (ETFE), polycarbonate, a biocompatible thermoplastic, or the like. In some examples, the electrically insulative plastic or polymer may be applied to electrically conductive layer 122 by a molding, dip coating or another coating method, laser treatment, spraying, etching treatment, or the like.

In some examples, housing 27a may comprise at least one additional layer formed over electrically insulative layer 166. Each of the additional layers may comprise materials described above, or may comprise other materials that provide one or more desired properties to housing 27a, such as electrical insulation, thermal insulation, mechanical protection, chemical protection, biocompatibility, or the like. For example, electrically insulative layer 166 may comprise a first electrically insulative material, and the one or more additional layers formed over electrically insulative layer 166 may comprise a different electrically insulative material. For example, electrically insulative layer 166 may comprise an electrically insulative metal oxide, an electrically insulative metal nitride, an electrically insulative ceramic, or an electrically insulative sintered material, while an additional layer comprises an electrically insulative plastic or polymer. As another example, electrically insulative layer 166 may comprise a first electrically insulative metal oxide, electrically insulative metal nitride, electrically insulative ceramic, or electrically insulative sintered material, and an additional layer may comprise a second electrically insulative metal oxide, electrically insulative metal nitride, electrically insulative ceramic, or electrically insulative sintered material, which may be different than the material from which the electrically insulative layer 166 is formed. Other combinations of materials for electrically insulative layer 166 and any additional layers formed over electrically insulative layer 166 are also contemplated.

Electrically insulative layer 166 may comprise may comprise a range of thicknesses, and in some examples electrically insulative layer 166 may comprise a thickness of approximately 2.54 micrometers (0.1 mils) to approximately 762 micrometers (30 mils). In other examples, electrically insulative layer 166 may comprise a thickness less than approximately 2.54 micrometers (0.1 mils) or greater than approximately 762 micrometers.

Figure 11:
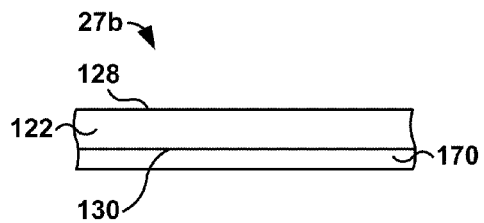
FIG. 11 is a schematic cross-sectional diagram illustrating an example medical device housing that includes an electrically conductive layer and an electrically insulative layer formed over an internal surface of the electrically conductive layer.

FIG. 11 is a schematic cross-sectional diagram illustrating an example medical device outer housing 27b that includes an electrically conductive layer 122 and an electrically insulative layer 170 formed over an interior surface 130 of electrically conductive layer 122. As previously indicated, interior surface 130 of electrically conductive layer 122 is closer to the components enclosed within outer housing 27b (e.g., processor, memory, and the like) than the exterior surface 128. Housing 27b may be an example of housing 27 (FIG. 7) of INS 26. Electrically insulative layer 170 may substantially fully cover or line interior surface 130 of electrically conductive layer 122, as well as other electrically conductive portions of an interior surface of housing 27b. As described above, electrically conductive layer 122 may comprise, for example, a biocompatible metal, such as titanium, stainless steel, or the like, and may be more electrically conductive than surrounding tissue of patient 12. Electrically conductive layer 122 may define the space in which outer housing 27b substantially encloses operative components of INS 26, such as those shown in FIG. 7.

First layer 170 may increase the effective impedance of housing 27b and decrease the amount of shunt-current that flows through housing 27b into an interior of the housing 27b, or may even substantially eliminate shunt-current from flowing through housing 27b. In some examples, the electrically insulative material may increase the impedance of housing 27b to such an extent that the impedance of housing 27b is greater than the impedance of tissue surrounding housing 27b, so that electrical current encounters less resistance flowing through the tissue than through housing 27b. In this way, first layer 170 may help reduce or even eliminate the shunt-current that flows through housing 27b and into the components of the medical device, such as stimulation generation circuitry or sensing circuitry. Reducing or eliminating the shunt-current that is introduced into the components of the medical device that are enclosed within housing 27b may help maintain the integrity and functionality of the medical device.

In some examples, the electrically insulative layer 170 may include an electrically insulative metal oxide, an electrically insulative metal nitride, an electrically insulative ceramic, or an electrically insulative sintered material. For example, the electrically insulative layer of housing 27 may include aluminum oxide ($Al_2O_3$), silicon dioxide ($SiO_2$), silicon nitride ($Si_3N_4$), aluminum nitride (AlN), glass, porcelain, diamond, or titanium dioxide ($TiO_2$). In some examples, electrically insulative layer 170 may be formed by oxidation of the material from which electrically conductive layer 122 is formed (e.g., oxidation of titanium to form titanium dioxide). In other examples, electrically insulative layer 170 may be formed on or otherwise deposited on electrically conductive layer 122 by ion-beam deposition, sputtering, or another atomic or molecular treatment.

In other examples, the electrically insulative layer 170 may include an electrically insulative plastic or polymer. The electrically insulative plastic or polymer may include, for example, silicone, polyethylene, cross-linked polyethylene, parylene, polyimide, epoxy, polyurethane, polyvinylchloride (PVC), rubber-like polymers, polytetrafluoroethylene (PTFE), ethylene tetrafluoroehtylene (ETFE), polycarbonate, a biocompatible thermoplastic, or the like. In some examples, the electrically insulative plastic or polymer may be applied to electrically conductive layer 122 by a molding, dip coating or another coating method, laser treatment, spraying, etching treatment, or the like.

In some examples, housing 27b may comprise one or more additional electrically insulative layers formed over electrically insulative layer 170, which may comprise the same or different electrically insulative materials. For example, electrically insulative layer 170 may comprise an electrically insulative metal oxide, an electrically insulative metal nitride, an electrically insulative ceramic, or an electrically insulative sintered material, while an additional layer formed over electrically insulative layer 170 comprises an electrically insulative plastic or polymer. As another example, electrically insulative layer 170 may comprise a first electrically insulative metal oxide, electrically insulative metal nitride, electrically insulative ceramic, or electrically insulative sintered material, and an additional layer formed over electrically insulative layer 170 may comprise a second electrically insulative metal oxide, electrically insulative metal nitride, electrically insulative ceramic, or electrically insulative sintered material, which may be different than the material from which electrically insulative layer 170 is formed. Other combinations of materials for electrically insulative layer 170 and any additional layers formed over electrically insulative layer 170 are also contemplated.

Electrically insulative layer 170 may comprise may comprise a range of thicknesses, and in some examples may comprise a thickness of approximately 2.54 micrometers (0.1 mils) to approximately 762 micrometers (30 mils). In other examples, electrically insulative layer 170 may comprise a thickness less than approximately 2.54 micrometers (0.1 mils) or greater than approximately 762 micrometers (30 mils).

Figure 12:
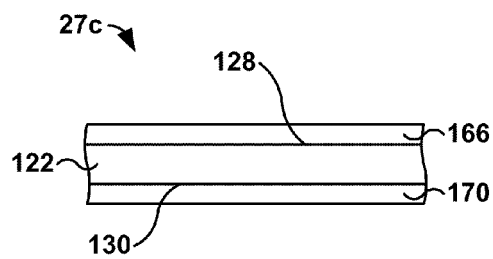
FIG. 12 is a schematic cross-sectional diagram illustrating an example medical device housing that includes an electrically conductive layer, an electrically insulative layer formed over an internal surface of the electrically conductive layer, and an electrically insulative layer formed over an external surface of the electrically conductive layer.

FIG. 12 is a schematic cross-sectional diagram illustrating an example medical device outer housing 27c including an electrically conductive layer 122, and both insulative layers 166 and 170 of housings 27a (FIG. 10) and housing 27b (FIG. 11), respectively. In particular, electrically insulative layer 166 is formed over an exterior surface 128 of electrically conductive layer 122, and an electrically insulative layer 170 is formed over an interior surface 130 of electrically conductive layer 122. At least one of first electrically insulative layer 166 and second electrically insulative layer 170 may substantially fully cover a respective surface 130, 128 of electrically conductive layer 122. Housing 27c may be an example of housing 27 (FIG. 7) of INS 26. In some examples, first electrically insulative layer 166 and second electrically insulative layer 170 comprise the same electrically insulative material, while in other examples, first electrically insulative layer 166 and second electrically insulative layer 170 may comprise different electrically insulative materials. For example, first electrically insulative layer 166 may comprise an electrically insulative metal oxide, electrically insulative metal nitride, electrically insulative ceramic, or electrically insulative sintered material, while second electrically insulative layer 170 may comprise an electrically insulative plastic or polymer. As another example, first electrically insulative layer 166 may comprise a first electrically insulative metal oxide, electrically insulative metal nitride, electrically insulative ceramic, or electrically insulative sintered material, and second electrically insulative layer 170 may comprise a second electrically insulative metal oxide, electrically insulative metal nitride, electrically insulative ceramic, or electrically insulative sintered material, which may be different than the material from which the first electrically insulative layer 166 is formed. Other combinations of materials for first electrically insulative layer 166 and second electrically insulative layer 170 are also contemplated.

In some examples, housing 27c may comprise one or more additional electrically insulative layers formed over at least one of first electrically insulative layer 166 and second electrically insulative layer 170, which may comprise the same or different electrically insulative materials as first electrically insulative layer 166 and/or second electrically insulative layer 170. For example, first electrically insulative layer 166 may comprise an electrically insulative metal oxide, electrically insulative metal nitride, electrically insulative ceramic, or electrically insulative sintered material, while an additional layer formed over first electrically insulative layer 166 comprises an electrically insulative plastic or polymer. As another example, second electrically insulative layer 170 may comprise a first electrically insulative metal oxide, electrically insulative metal nitride, electrically insulative ceramic, or electrically insulative sintered material, and an additional layer formed over second electrically insulative layer 170 may comprise a second electrically insulative metal oxide, electrically insulative metal nitride, electrically insulative ceramic, or electrically insulative sintered material, which may be different than the material from which second electrically insulative layer 170 is formed. Other combinations of materials for first electrically insulative layer 166 and second electrically insulative layer 170 and any additional layers formed over first electrically insulative layer 166 and second electrically insulative layer 170 are also contemplated.

Each of first electrically insulative layer 166 and second electrically insulative layer 170 may comprise may comprise a range of thicknesses, and in some examples may one or both of first electrically insulative layer 166 and second electrically insulative layer 170 comprise a thickness of approximately 2.54 micrometers (0.1 mils) to approximately 762 micrometers (30 mils). In other examples, one or both of first electrically insulative layer 166 and second electrically insulative layer 170 may comprise a thickness less than approximately 2.54 micrometers (0.1 mils) or greater than approximately 762 micrometers (30 mils). However, other thicknesses are contemplated and may also provide sufficient electrical insulation of electrically conductive layer 122.

Figure 13:
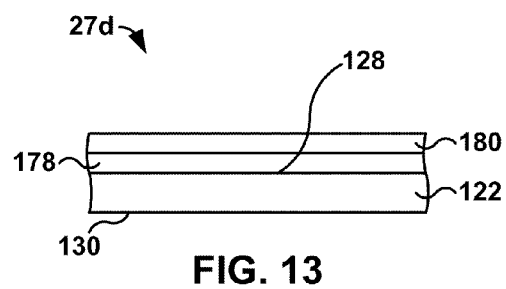
FIG. 13 is a schematic cross-sectional diagram illustrating an example medical device housing that includes an electrically conductive layer, an electrically insulative spacer formed over an external surface of the electrically conductive layer, and a third layer formed over the electrically insulative spacer.

FIG. 13 is a schematic cross-sectional diagram illustrating an example medical device outer housing 27d that includes an electrically conductive layer 122, an electrically insulative spacer 178 formed over an exterior surface 128 of electrically conductive layer 122, and a third layer 180 formed over electrically insulative spacer 178. Housing 27d may be an example of housing 27 (FIG. 7) of INS 26. Again, electrically conductive layer 122 may comprise a biocompatible metal, such as, for example, titanium or stainless steel.

In some examples, third layer 180 comprises at least one of the electrically insulative materials described above, such as, for example, an electrically insulative metal oxide, electrically insulative metal nitride, electrically insulative ceramic, electrically insulative sintered material, electrically insulative polymer or plastic, or the like. In other examples, third layer 180 comprises a material that provides another property to housing 27d, such as, for example, chemical protection, physical protection, or the like. In some examples, third layer 180 may be metallic, and may comprise, for example, a metal coating, a metal film, metal stamping, metal enclosure, or metal shield. In cases in which third layer 180 comprises a metal, the metal may be biocompatible, such as, for example, titanium, stainless steel, or the like. Other electrically insulative materials are contemplated.

In the example shown in FIG. 13, electrically insulative spacer 178 is disposed between electrically conductive layer 122 and third layer 180, and electrically insulates electrically conductive layer 122. In examples in which third layer 180 comprises metal, electrically insulative spacer 178 may electrically insulate electrically conductive layer 122 from third layer 180. In this way, even if an outer layer of medical device housing 27d that interfaces with tissue comprises an electrically conductive material, housing 27d may still help reduce or even eliminate the shunt-current that is introduced into the medical device components of housing 27d. In other examples, as described above, third layer 180 may comprise an electrically insulative material, and both electrically insulative spacer 178 and third layer 180 may help to electrically insulate electrically conductive layer 122 from tissue of patient 12 adjacent to housing 27d.

In some examples, electrically insulative spacer 178 may comprise a sleeve or other preformed object that fits around electrically conductive inner layer 122, e.g., into which electrically conductive inner layer 122 is fitted. Components of INS 26, such as processor 110 (FIG. 7), stimulation generator 114 (FIG. 7), and power supply 120 (FIG. 7), may be substantially enclosed by electrically conductive inner layer 122 prior to positioning electrically insulative spacer 178 around electrically conductive layer 122. Electrically insulative spacer 178 then may be attached to the inner layer by, for example, an adhesive or a heat treatment. Third layer 180 then may be formed over electrically insulative spacer 178. In other examples, electrically insulative spacer 178 may be formed over or otherwise deposited on electrically conductive layer 122 by ion-beam deposition, sputtering, another atomic or molecular treatment, molding, or the like.

In some examples, electrically insulative spacer 178 may not fully cover electrically conductive inner layer 122. Instead, electrically insulative spacer 178 may comprise one or more spacers that separate electrically conductive inner layer 122 from third layer 180 and provide an air gap between electrically conductive inner layer 122 and third layer 180. The air gap, along with electrically insulative spacer 178, may then provide the electrical insulation between electrically conductive inner layer 122 and third layer 180. In some examples, the air gap may be filled with nitrogen or another inert gas.

In some examples, third layer 180 defines the outermost layer of housing 27d that interfaces with tissue of patient 12 when INS 26 is implanted within patient 12. However, as described with respect to FIGS. 10-12, in some examples, housing 27d may comprise one or more additional layer formed over third layer 180, such that third layer 180 is not the outermost layer of outer housing 27d. For example, housing 27d may comprise one or more additional electrically insulative layers formed over third layer 180, which may comprise the same or different electrically insulative materials as electrically insulative spacer 178. For example, electrically insulative spacer 178 may comprise an electrically insulative metal oxide, electrically insulative metal nitride, electrically insulative ceramic, or electrically insulative sintered material, while an additional layer formed over third layer 180 comprises an electrically insulative plastic or polymer. As another example, electrically insulative spacer 178 may comprise a first electrically insulative metal oxide, electrically insulative metal nitride, electrically insulative ceramic, or electrically insulative sintered material, and an additional layer formed over third layer 180 may comprise a second electrically insulative metal oxide, metal electrically insulative nitride, electrically insulative ceramic, or electrically insulative sintered material, which may be different than the material from which electrically insulative spacer 178 is formed. Other combinations of materials for electrically insulative spacer 178, third layer 180, and any additional layers formed over third layer 180 are also contemplated.

Figure 14:
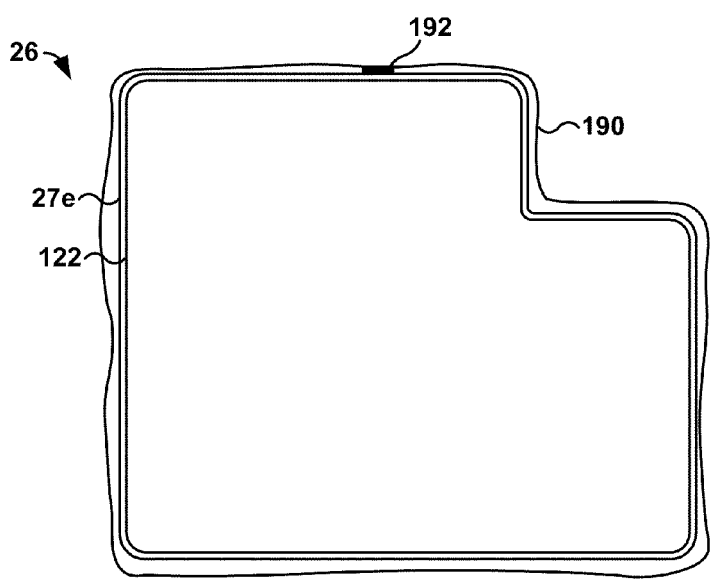
FIG. 14 is a conceptual diagram illustrating an example INS including an electrically insulative pouch that substantially fully encapsulates a housing of the INS.

FIG. 14 is a conceptual diagram illustrating an example INS 26 including an electrically insulative pouch 190 that encapsulates an outer housing 27e of INS 26. Housing 27e is an example of housing 27 (FIG. 7) of INS 26. Accordingly, housing 27e may substantially enclose therapy components of INS 26, such as a stimulation generator, sensing circuitry, a processor, and the like. In some examples, housing 27e may hermetically enclose at least some or all of the therapy components of INS 26. In some examples, instead of or in addition to a housing 27 comprising an electrically insulative layer (e.g., electrically insulative layer 126, FIG. 7) or an electrically insulative spacer 178 (FIG. 13), INS 26 may comprise an electrically insulative pouch 190 that substantially fully encapsulates housing 27e. Similar to a housing 27 that includes an electrically insulative layer 126 (FIG. 7), the electrically insulative pouch 190 may mitigate or substantially eliminate shunt-current from flowing from electrodes carried by leads 18, 20, 22 connected to ICD 16 to housing 27e of INS 26.

Electrically insulative pouch 190 may comprise, for example, a preformed covering into which housing 27e of INS 26 fits. In some examples, electrically insulative pouch 190 may comprise a size and/or shape that does not substantially conform to the size and/or shape of housing 27e, as shown in FIG. 14. For example, electrically insulative pouch 190 may be sized larger than housing 27e, so that there is not a friction fit between pouch 190 and housing 27e, and the pouch 190 fits more loosely around housing 27e. Although not shown in FIG. 14, in other examples, electrically insulative pouch 190 may comprise a size and/or shape that substantially conforms to the size and/or shape of housing 27e, so that the pouch 190 forms an intimate fit with housing 27e. For example, electrically insulative pouch 190 may be sized and/or shaped to form a friction fit with one or more surfaces of housing 27e. Electrically insulative pouch 190 may be substantially flexible or rigid.

In any case, electrically insulative pouch 190 may substantially fully enclose or encapsulate housing 27e. In this way, electrically insulative pouch 190 may mitigate or substantially prevent shunt-current from traveling from electrodes carried by leads 18, 20, 22 connected to ICD 16 to housing 27e of INS 26. In addition, by substantially fully encapsulating the outer surface of housing 27e, pouch 190 may help reduce the concentration of shunt-current at one or more portions of housing 27e by reducing the possibility that any electrically conductive portions of housing 27e are exposed to the shunt-current. In some examples, electrically insulative pouch 190 may comprise a single piece of material, which comprises a slot or other opening into which the housing 27e is placed. The slot or opening may then be closed using an adhesive, solvent welding, ultrasonic welding, thermal welding, or the like to form a continuous, unitary enclosure around housing 27e. In some examples, electrically insulative pouch 190 may be coupled or attached to housing 27e in one or more location to reduce or eliminate relative motion between housing 27e and electrically insulative pouch 190. Electrically insulative pouch 190 may be coupled or attached to housing 27e by an adhesive 192, such as a silicone or epoxy adhesive, although other attachment mechanisms may also be used. Although adhesive 192 is shown to be at one part of the interface between pouch 190 and housing 27e, in other examples, adhesive 192 may be positioned substantially fully between housing 27e and pouch 190.

In other examples, electrically insulative pouch 190 may comprise two or more pieces of material that are arranged around housing 27e and then coupled to each other and, optionally, to housing 27e. For example, electrically insulative pouch 190 may comprise a first portion and a second portion. The first and second portions may be placed, for example, on a first side and a second side of housing 27e (the first and second sides may or may not be opposite each other). The first and second portions of electrically insulative pouch 190 may be coupled or attached to the first and second sides of housing 27, respectively, using adhesive 192 or another suitable attachment mechanism. The first and second portions of electrically insulative pouch 190 then may be coupled to each other using an adhesive, solvent welding, thermal welding, or another suitable process.

Electrically insulative pouch 190 may comprise, for example, a biocompatible polymer or plastic, which may or may not be flexible. In some examples, electrically insulative pouch 190 may comprise at least one of silicone, polyethylene, cross-linked polyethylene, parylene, polyimide, epoxy, polyurethane, polyvinylchloride (PVC), rubber-like polymers, polytetrafluoroethylene (PTFE), ethylene tetrafluoroethylene (ETFE), polycarbonate, a biocompatible thermoplastic, or the like. Electrically insulative pouch 190 may comprise a thickness of about 25.4 micrometers (about 0.001 inches) to a thickness of about 1016 micrometers (about 0.040 inches), or about 254 micrometers (about 0.01 inches) to a thickness of about 508 micrometers (about 0.02 inches).

Electrically insulative pouch 190 may be assembled around housing 27e by a manufacturer of INS 26 at the time of manufacture or prior to shipping INS 26 to a wholesaler or the implanting clinician. In other examples, electrically insulative pouch 190 may be assembled with housing 27e by the implanting clinician at or before the time at which INS 26 is implanted in a patient 12. In some examples, the implanting clinician may determine at or before the time of implant whether an electrically insulative pouch around housing 27 of INS 26 may be useful for the particular therapy system implanted within patient 12. Accordingly, the clinician may or may not assemble insulative pouch 190 around housing 27 depending on his or her determination at or near the time of implant within a particular patient 12. For example, the implanting clinician may consider the implant location of INS 26, ICD 16, and any leads coupled to INS 26 or ICD 16 when determining whether INS 26 would benefit from electrically insulative pouch 190. When the implanting clinician determines that INS 26 would benefit from electrically insulative pouch 190, the clinician may assemble electrically insulative pouch 190 around housing 27 of INS 26.

In some examples, electrically insulative pouch 190 may be shaped and/or sized to fit a single type or class of implantable devices (e.g., a single type of INS 26), and the manufacturer, implanting physician or technician may select an electrically insulative pouch 190 that is appropriate for the type (e.g., model) of INS 26 being implanted in patient 12. In other examples, electrically insulative pouch 190 may comprise a more generic size and/or shape, and may be configured to be used with a wider range of implantable devices. In this case, the manufacturer, implanting physician or technician may utilize the same electrically insulative pouch regardless of the type of implantable device being implanted in patient 12. In this way, only a single configuration of electrically insulative pouch 190, or a small number of configurations of pouch 190 need be made, which may be used with a large number of implantable devices.

Electrically insulative pouch 190 may also facilitate manufacture of INS 26 or other implantable devices with which pouch 190 may be used. In particular, use of an electrically insulative pouch 190 may allow housing 27e of INS 26 to be a simple metal housing, e.g., titanium of stainless steel, as is conventionally used. This may simplify and minimize the cost of manufacturing outer housing 27e compared those costs and complexities encountered when manufacturing an outer housing comprising a plurality of layers. Further electrically insulative pouch 190 may be used with existing implantable devices, e.g., INS 26, without requiring any modification of housing 27e.

While not depicted in FIG. 14, electrically insulative pouch 190 may also be disposed inside of housing 27e and may encapsulate components housed in housing 27e, such as, for example, electrical circuitry and/or wiring. In some cases, the electrical circuitry and/or wiring may not be electrically connected to housing 27e, and electrically insulative pouch 190 may electrical insulate of the circuitry and/or wiring from housing 27e. In this way, electrically insulative pouch 190 disposed within housing 27e around components may eliminate any direct electrical connection between the circuitry and or/wiring and housing 27e, and may reduce any capacitive or inductive electrical coupling between the circuitry and wiring and housing 27e. In some examples, INS 26 includes an electrically insulative layer or an electrically insulative pouch 190 that substantially fully covers or encapsulates an outer surface of housing 27e in addition to an electrically insulative pouch 190 that encapsulates components housed in housing 27e. In other example, INS 26 may not include an electrically insulative layer or electrically insulative pouch 190 that substantially fully covers or encapsulates an outer surface of housing 27e in addition to an electrically insulative pouch 190 that encapsulates components housed in housing 27e.

FIGS. 15-20 are conceptual diagrams illustrating various examples of shunt-current mitigation circuitry 119 (FIG. 7) that may be used to reduce shunt-current received by INS 26 through an electrical path including electrodes 124 due to the delivery of stimulation by ICD 16. FIGS. 15-20 illustrate stimulation generator 114 disposed within housing 27 of INS 26. For purposes of illustration and clarity, the additional components of INS 26, such as switching module 116 and processor 110, are not illustrated in FIGS. 15-20. Although FIGS. 15-20 illustrate an example in which shunt-current mitigation circuitry 119 is external to housing 27, in other examples, shunt-current mitigation circuitry 119 may be enclosed within housing 27, connector block 42 (FIG. 1) or otherwise electrically coupled to electrodes 124.

Figure 15:
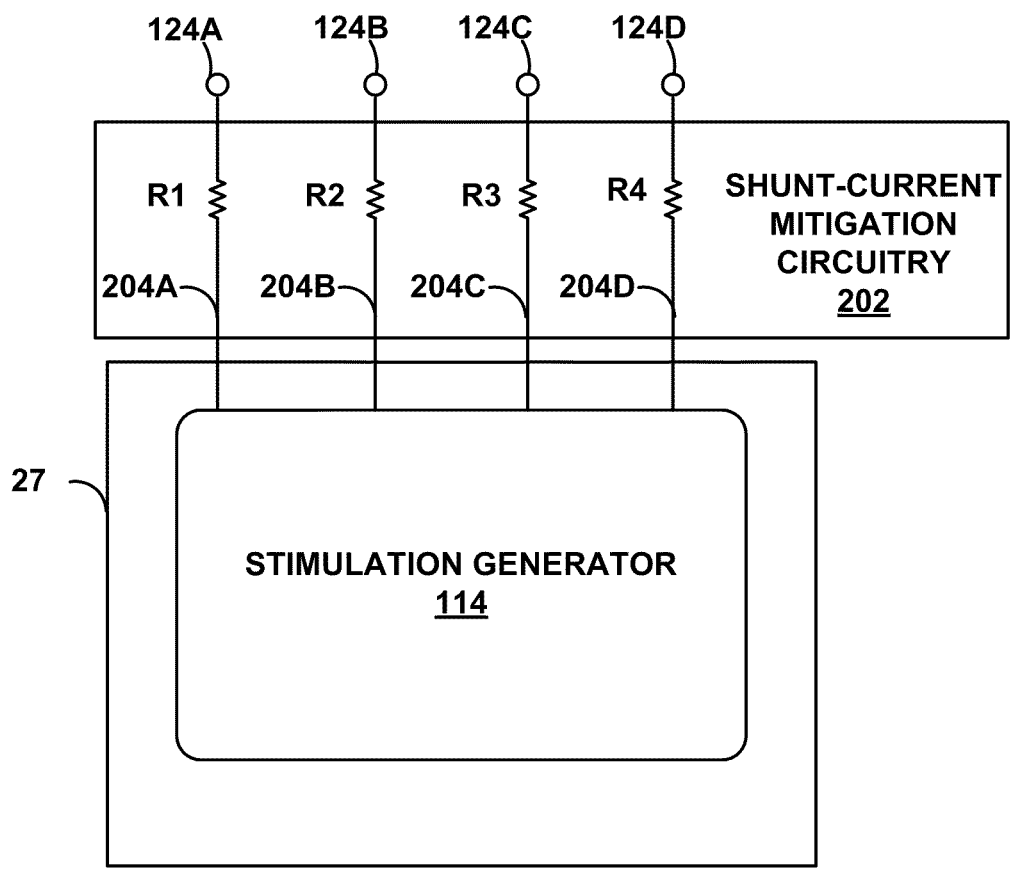
FIG. 15 is a block diagram illustrating an example implantable medical device (IMD) that includes shunt-current mitigation components.

FIG. 15 is a conceptual block diagram that illustrates an example of shunt-current mitigation circuitry 202, which is an example of shunt-current mitigation circuitry 119 (FIG. 7) that may be used with INS 26. In the example shown in FIG. 15, electrodes 124A-124D of lead 28 (FIG. 7) are electrically coupled to stimulation generator 114 with a respective conductor 204A-204D (collectively "conductors 204"). Conductors 204 may be enclosed in a common lead body (e.g., lead 28) or separate lead bodies. In the example shown in FIG. 15, shunt-current mitigation circuitry 202 comprises resistors R1-R4, which are electrically coupled to a respective one of the conductors 204. As shown in FIG. 15, resistors R1-R4 are external to housing 27. In some examples, resistors R1-R4 may be internal to housing 27. Additionally, while not shown in FIG. 15, in some examples, stimulation circuitry 114 or another component of INS 26 may be electrically coupled to an electrically conductive layer 122 of housing 27 by a wire or other conductive element, similar to wire 134 illustrated in FIG. 7.

Resistors R1-R4 may comprise relatively high impedance (or "resistance") resistors. Resistors R1-R4 may each have a resistance of about one kiloohm to about 10 kiloohms, although other resistance values are contemplated. In some examples, conductors 204 may comprise low impedance wires. In some other examples, conductors 204 may comprise high impedance wires. Example values of the impedance of conductors 204 may be about 10 ohms to 10 kiloohms, about 10 ohms to 100 ohms, or about 3.5 kiloohms to 10 kiloohms, although other impedance values are contemplated. Furthermore, in some examples, shunt-current mitigation circuitry 202 may not include resistors R1-R4, but the shunt-current mitigation may be provided by high-impedance wires comprised by conductors 204. In such examples, the high impedance wires of conductors 204 may be considered shunt-current mitigation circuitry 202.

Resistors R1-R4 and/or relatively high impedance wires of conductors 204 increase an impedance of the shunt-current path through electrodes 124. Accordingly, the presence of resistors R1-R4 may reduce the amount shunt-current that flows through an electrical path including electrodes 124 into INS 26 from the delivery of electrical stimulation by ICD 16. In this way, increasing the impedance of the electrical path between electrodes 124 and stimulation generator 114 of INS 26 may help reduce the amount of shunt-current that is introduced into stimulation generator 114, as well as reduce the possibility that tissue between INS 26 and ICD 16 may be unintentionally stimulated or stressed due to the flow of shunt-current through electrodes 124.

The flow of shunt-current into stimulation generator 114 through an electrical path including electrodes 124 may be undesirable because stimulation generator 114 may be intended only to source electrical current as stimulation signals and not to sink electrical current. The shunt-current may cause stimulation generator 114 to sink current, which may stress the stimulation generator if stimulation generator 114 is only configured to source current. Moreover, the shunt-current and the stimulation current generated by stimulation generator 114 may flow in opposite directions. For example, the shunt-current may flow into electrodes 124 while the stimulation current may flow out of electrodes 124. Thus, the flow of shunt-current into electrodes 124 may reduce the amount of stimulation that is actually provided by the stimulation generator 114, which may affect the efficacy of the therapy provided by INS 26.

Although not shown in FIG. 15, in some examples, shunt-mitigation circuitry 202 includes a plurality of switches, whereby at least one switch is coupled to a respective resister R1-R4. The switches may comprise any one or more of electronic switches, FET switches, reed switches, optical isolators, SCRs, or other forms of switches. When closed, each one of switches may provide a low impedance electrical path for a stimulation signal generated by ICD 16 (FIG. 1) or another source. The switches can generally remain open except for when electrodes 124 need to be electrically connected to components within INS 26. For example, the switches may remain open except for when stimulation generator 114 is delivering a stimulation signal via electrodes 124, when a sensing module within INS 26 is sensing one or more physiological parameters of patient 12 via electrodes 124, or when processor 110 (FIG. 7) of INS 26 determines an impedance of an electrical path including electrodes 124, e.g., for lead integrity determinations. When stimulation generator 114 is about to transmit a neurostimulation signal, processor 110 of INS 26 may toggle the switches closed, thereby creating a low impedance electrical path for the neurostimulation signal. When the switches are open, no shunt-current may flow through the switches, and all the shunt-current may only flow through resistors R1-R4.

Figure 16:
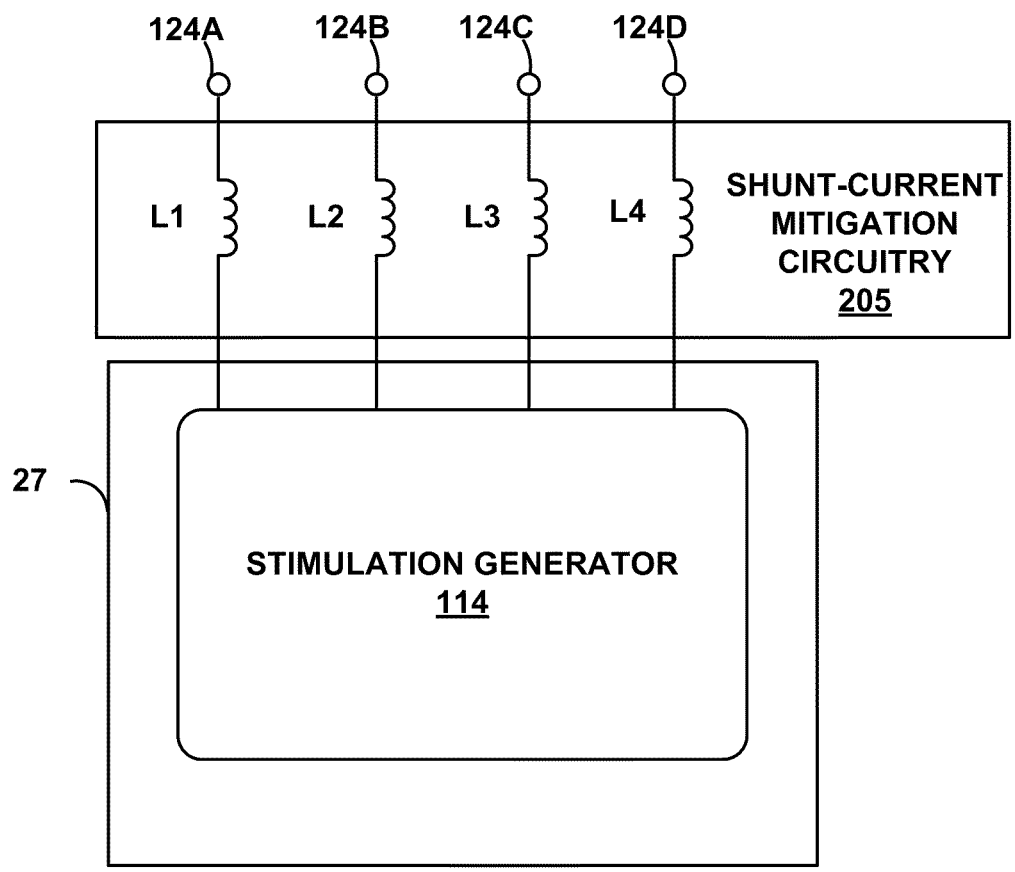
FIG. 16 is a block diagram illustrating another example IMD that includes shunt-current mitigation components

FIG. 16 is a block diagram illustrating another example of shunt-current mitigation circuitry 205. In the example shown in FIG. 16, shunt-current mitigation circuitry 205 comprises inductors L1-L4, which are electrically coupled to stimulation generator 114 of INS 26 and electrodes 124. Electrodes 124A-124D are electrically coupled to stimulation generator 114 via inductors L1-L4, respectively. As shown in FIG. 16, inductors L1-L4 are located externally to housing 27. In other examples, inductors L1-L4 may be internal, e.g., enclosed within housing 27. In some examples, inductors L1-L4 may be provided by conductors 204 themselves. In such examples, conductors 204 may be considered shunt-current mitigation circuitry 205. Additionally, while not shown in FIG. 16, in some examples, stimulation circuitry 114 may be electrically coupled to an electrically conductive layer 122 of housing 27 by a wire or other conductive element, similar to wire 134 illustrated in FIG. 7

Inductors L1-L4 may mitigate shunt-current from flowing to stimulation generator 114 by inhibiting instantaneous changes in currents flowing through electrodes 124 and conductors 204. In some examples, inductors L1-L4 may be formed by coiling conductors 204. In some examples, inductors L1-L4 may be used in combination with resistors R1-R4 or resistive conductors 204 comprising a relatively high impedance wire. Examples values of the inductance of inductors L1-L4 may be about 0.1 millihenry (mH) to about 100 mH, although other inductance values are contemplated.

Figure 17:
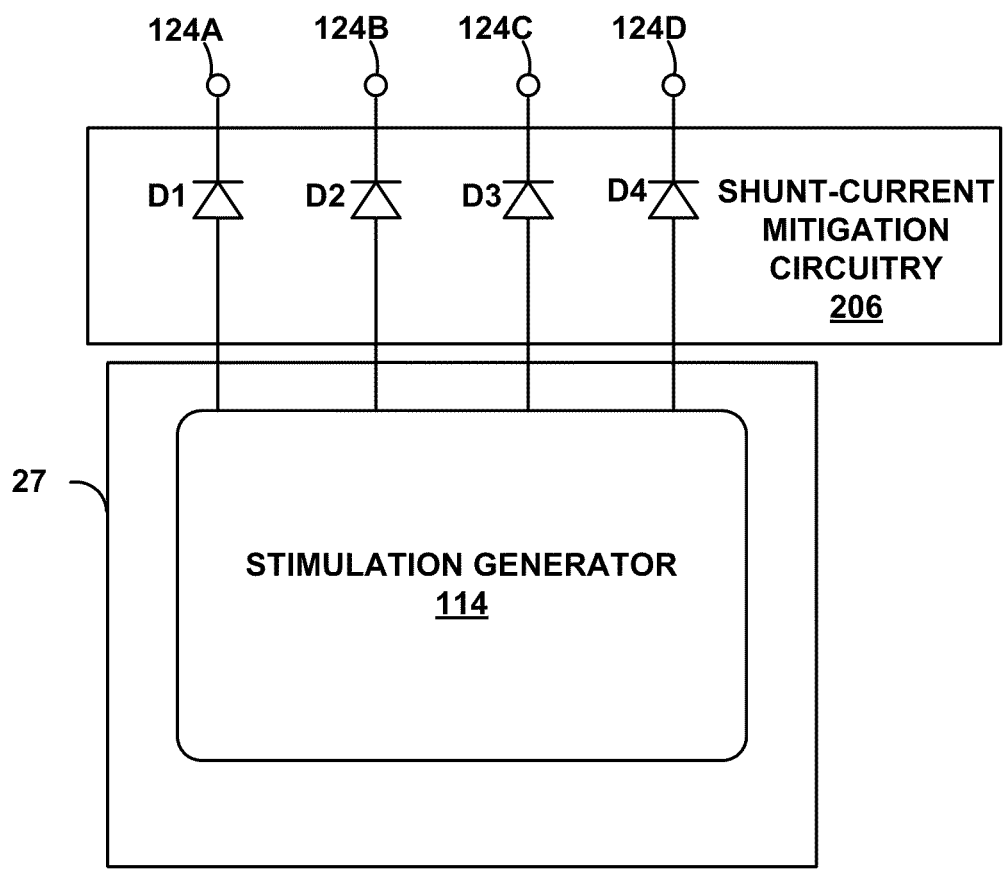
FIG. 17 is a block diagram illustrating another example IMD that includes shunt-current mitigation components.

FIG. 17 is a block diagram illustrating another example of shunt-current mitigation circuitry 206. In the example shown in FIG. 17, shunt-current mitigation circuitry 206 comprises diodes D1-D4, which are electrically coupled to stimulation generator 114 of INS 26 and electrodes 124. Electrodes 124A-124D are electrically coupled to stimulation generator 114 via diodes D1-D4, respectively. As shown in FIG. 16, diodes D1-D4 are located externally to housing 27. In other examples, diodes D1-D4 may be internal, e.g., enclosed within housing 27. In some examples, diodes D1-D4 may comprise diodes that are configured to conduct in two directions. For example, diodes D1-D4 may comprise transient absorber diodes, Zener diodes, or the like. Diodes D1-D4 may allow the current generated by stimulation generator 114 to flow to electrodes 124 via conductors within lead 28. However, diodes D1-D4 may limit the amount of current that may flow from electrodes 124 to stimulation generator 114. Additionally, while not shown in FIG. 17, in some examples, stimulation circuitry 114 may be electrically coupled to an electrically conductive layer 122 of housing 27 by a wire or other conductive element, similar to wire 134 illustrated in FIG. 7

In some examples, diodes D1-D4 may be leaky diodes that allow charge that is built up on electrodes 124 to dissipate into housing 27. Because diodes D1-D4 only allow current to flow in one direction, electrodes 124 may build up charge which may cause electrodes 124 to corrode. The leaky characteristic of diodes D1-D4 may allow the built up charge to dissipate into housing 27 and minimize the corrosion of electrodes 124.

Diodes D1-D4 may generate a high impedance path for a shunt-current to flow from electrodes 124 into stimulation generator 114. The impedance of the electrical path including electrodes 124 may be higher with diodes D1-D4 than without diodes D1-D4. Accordingly, the presence of diodes D1-D4 may reduce the amount of shunt-current that flows from ICD 16 through an electrical path including electrodes 124 to INS 26. In this way, placing diodes D1-D4 in the electrical path between electrodes 124 and stimulation generator 114 may help reduce the amount of shunt-current that is introduced into stimulation generator 114, as well as reduce the possibility that tissue adjacent electrodes 124 may be unintentionally stimulated or otherwise stressed due to the flow of shunt-current through electrodes 124.

FIG. 18 is a conceptual block diagram illustrating another example shunt-current mitigation circuit 208, which includes switches S1-S4 that are electrically coupled to a respective electrode 124A-124D, respectively. Switches S1-S4 may comprise any one or more of electronic switches, FET switches, reed switches, optical isolators, SCRs, and the like. Switches S1-S4 may be controlled by processor 110 (FIG. 7) of INS 26. In some examples, ICD 16 may transmit a communication signal to INS 26 via the respective telemetry modules 98 (FIG. 6), 118 (FIG. 7), where the communication signal indicates prospective therapy delivery by ICD 16. The therapy delivery may be, for example, the delivery of a defibrillation shock to heart 14 (FIG. 1) of patient 12. In some other examples, ICD 16 may transmit a communication signal to programmer 24 (FIG. 1) via telemetry module 98 (FIG. 6), where the communication signal is indicative of prospective therapy delivery by ICD 16. Programmer 24 may transmit the communication signal to INS 26, which may receive the communication signal via telemetry module 118. The communication signal may or may not provide therapeutic benefits to patient 12. In response to receiving the communication signal from ICD 16, processor 110 of INS 26 may toggle switches S1-S4 open in order to limit or even stop the current flow through switches S1-S4. In this way, the opening of switches S1-S4 may reduce the flow of shunt-current from the stimulation generated by ICD 16 through an electrical path including electrodes 124 and into stimulation generator 114. While not shown in FIG. 18, in some examples, stimulation circuitry 114 may be electrically coupled to an electrically conductive layer 122 of housing 27 by a wire or other conductive element, similar to wire 134 illustrated in FIG. 7

Figure 19:
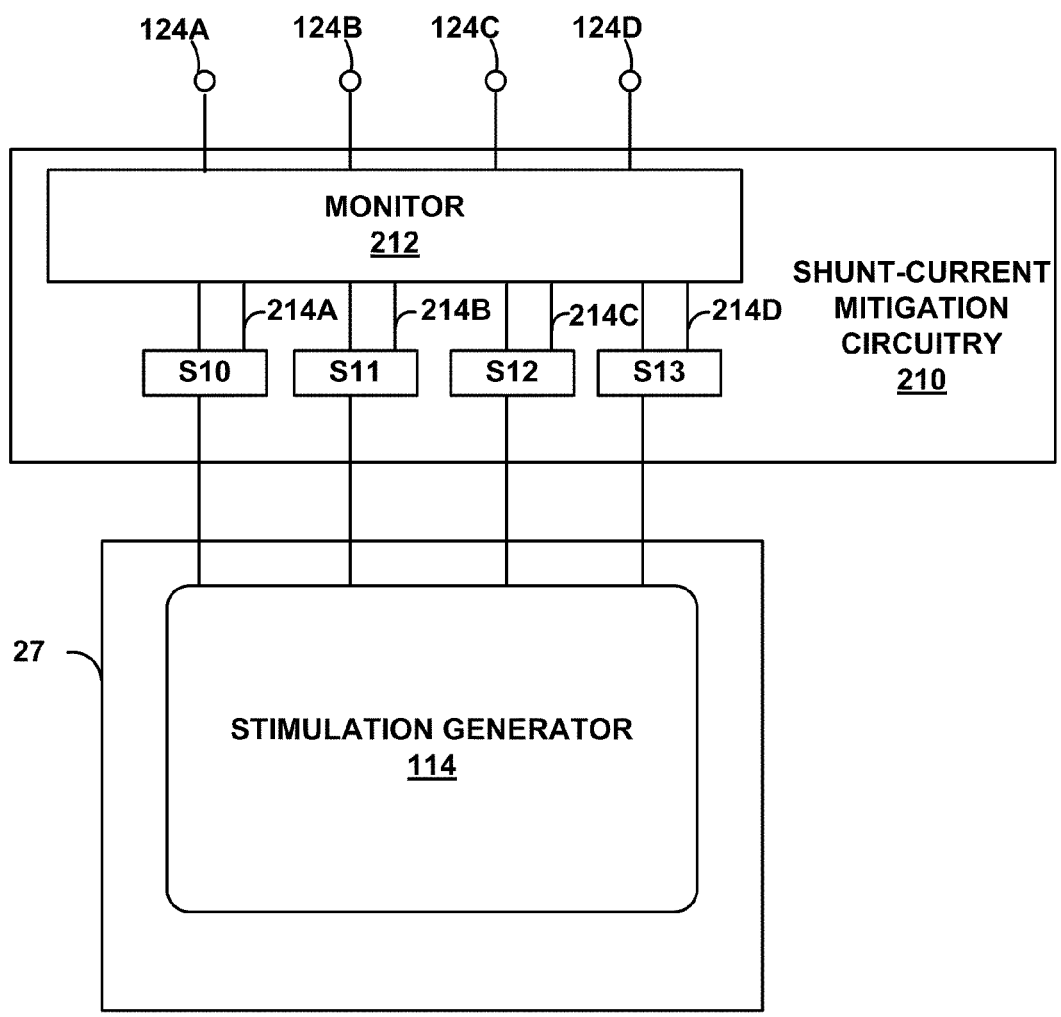
FIG. 19 is a block diagram illustrating another example IMD that includes shunt-current mitigation components.

FIG. 19 is a block diagram illustrating another example of shunt-current mitigation circuitry 210, which includes monitor 212 and switches S10-S13. Monitor 212 monitors an electrical parameter value at one or more of the electrodes 124. The electrical parameter value may be a voltage at each one of electrodes 124, a current through each one of electrodes 124, or a voltage across at least two of electrodes 124. In the example shown in FIG. 19, electrodes 124A-124D are electrically coupled to stimulation generator 114 via monitor 212 and switches S10-S13, respectively. Monitor 212 may include a voltage monitor or a current monitor. In some examples, monitor 212 comprises a plurality of current monitors or voltage monitors that monitor the current flowing through a respective one of electrodes 124, or monitor the voltage at each one of electrodes 124. A current monitor may monitor the current in series with the current flow through electrodes 124, and a voltage monitor may monitor voltage in parallel with the current flow through electrodes 124. Accordingly, in examples in which monitor 212 comprises one or more voltage monitors, each one of the voltage monitors may comprise a low impedance resistor. Each one of the voltage monitors may measure the voltage across the low impedance resistor.

In other examples in which monitor 212 comprises one or more voltage monitors, the voltage monitor may not measure the voltage at electrodes 124. Instead, the voltage monitor may measure the voltage across two of electrodes 124. For example, one voltage monitor may measure the voltage across electrode 124A and 124B, and a second voltage monitor may measure the voltage across electrode 124C and 124D. Measuring the voltage across two electrodes may be beneficial where electrodes 124 are bipolar electrodes.

In examples in which monitor 212 comprises a current monitor, if the current that flows through one or more of the electrodes 124 is greater than or equal to a predetermined threshold value, monitor 212 may transmit a signal via a respective control line 214A-214D to toggle switches S10-S13 open. Switches S10-S13 may be substantially similar to switches S1-S4 (FIG. 17). A clinician may select the threshold current value that triggers the opening of switches S10-S13. In some examples, the threshold current value may be within the range of about 1 milliamp to about 200 milliamps, such as about 10 milliamps to about 50 milliamps, although other threshold current values are contemplated. As previously discussed, the threshold current value may be selected based on various factors, such as the amount of current and/or energy that the circuitry within INS 26 is designed to withstand without substantial damage, the type of tissue in which electrodes 124 are implanted, or the surface area of electrodes 124.

In examples in which monitor 212 comprises a voltage monitor, if the voltage across the low impedance resistor within the voltage monitor is greater than or equal to a predetermined threshold voltage value or if the voltage across two of electrodes 124 is greater than the threshold voltage value, monitor 212 may transmit a signal via control line 214A-214D to toggle open switches S10-S13. Again, a clinician may select the threshold voltage value, which may be, for example, in a range of about 15 volts to about 1000 volts, such as about 15 volts to about 50 volts. However, other threshold voltage values are contemplated. Additionally, while not shown in FIG. 19, in some examples, stimulation circuitry 114 may be electrically coupled to an electrically conductive layer 122 of housing 27 by a wire or other conductive element, similar to wire 134 illustrated in FIG. 7

Figure 20:
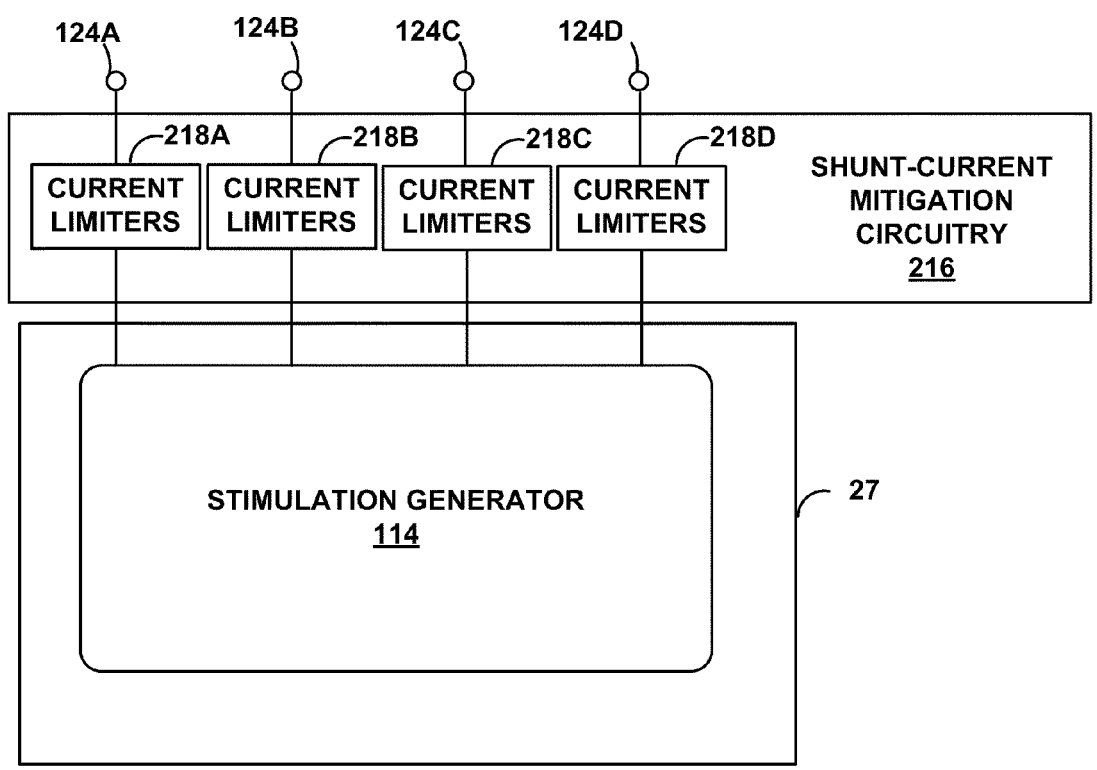
FIG. 20 is a block diagram illustrating another example IMD that includes shunt-current mitigation components.

FIG. 20 is a block diagram illustrating another example of shunt-current mitigation circuitry 216, which may be an example of shunt-current mitigation circuitry 119 (FIG. 7). In the example shown in FIG. 20, shunt-current mitigation circuitry 216 comprises current limiters 218A-218D (collectively referred to as "current limiters 218"), which are electrically coupled to stimulation generator 114 and electrodes 124. Each one of current limiters 218 may comprise a fuse or a bimetallic circuit breaker, in one aspect. One example of a fuse is a resettable fuse.

Current limiters 218 may limit the amount of current that may flow from electrodes 124 to stimulation generator 114. If the current that may flow from electrodes 124 is greater than a threshold current for current limiters 218, current limiters 218 may provide a high impedance for the current, thereby limiting the amount of current that may flow from electrodes 124 to stimulation generator 114. For example, at least one of the current limiters 218 may comprise a resettable fuse. The resettable fuse may activate and may provide high impedance when the shunt-current is greater than the threshold current. The resettable fuse provides high impedance path by blocking substantially all current, e.g., creating an open circuit. In such a manner, the resettable fuse activates to keep the shunt-current within or nearer to a desirable level, thereby reducing or avoiding stress to the tissue.

After activation, in some examples, the resettable fuse deactivates by itself or by a control signal provided by processor 110 (FIG. 7) of INS 26. Accordingly, the presence of current limiters 218 may limit the amount of shunt-current that flows from ICD 16 to INS 26. In this way, placing current limiters 218 in the electrical path between electrodes 124 and stimulation generator 114 may help limit the amount of shunt-current that is introduced into stimulation generator 114, as well as reduce the possibility that tissue adjacent electrodes 124 may be unintentionally stimulated or stressed due to the flow of shunt-current through electrodes 124. Additionally, while not shown in FIG. 20, in some examples, stimulation circuitry 114 may be electrically coupled to an electrically conductive layer 122 of housing 27 by a wire or other conductive element, similar to wire 134 illustrated in FIG. 7

Various shunt-current mitigation circuitries (or components) are described in FIGS. 15-20. In some examples, stimulation generator 114 may be coupled to one or more of the shunt-current mitigation circuitries described with respect to FIGS. 15-20. For example, stimulation generator 114 may be coupled to each one of electrodes 124 via a resistive wire, a resistor, a switch, and a monitor. As another example, stimulation generator 114 may be coupled to each one of electrodes 124 via only a resistive wire and a switch. Other permutations and combinations may be possible, and are contemplated by this disclosure.

Figure 21:
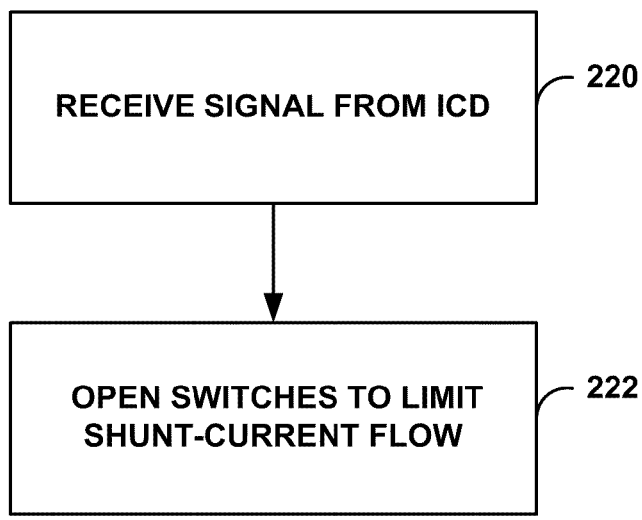
FIG. 21 is a flow diagram illustrating an example technique that may be implemented to reduce shunt-current that may flow through an electrical path connected to an IMD.

FIG. 21 is a flow diagram illustrating an example technique that INS 26 may implement in order to limit shunt-current. For purposes of illustration, reference will be made to shunt-current mitigation circuitry 208 described with respect to FIG. 18. In accordance with the technique shown in FIG. 21, INS 26 may receive a signal from ICD 16 indicating prospective therapy delivery by ICD 16 (220). For example, the signal may indicate INS 26 is about to provide a stimulation signal. The communication signal may be provided by telemetry module 98 (FIG. 6) and received by telemetry module 118 (FIG. 7). For example, ICD 16 may transmit a communication signal to programmer 24 (FIG. 1) via telemetry module 98 (FIG. 6), where the communication signal is indicative of prospective therapy delivery by ICD 16. In response to receiving the communication signal from ICD 16, processor 110 may control one or more switches S1-S4 to toggle open in order to limit the current that may feed into INS 26 via switches S1-S4 (22). In this way, the opening of switches S1-S4 may reduce the flow of shunt-current from the stimulation generated by ICD 16 into stimulation generator 114.

Figure 22:
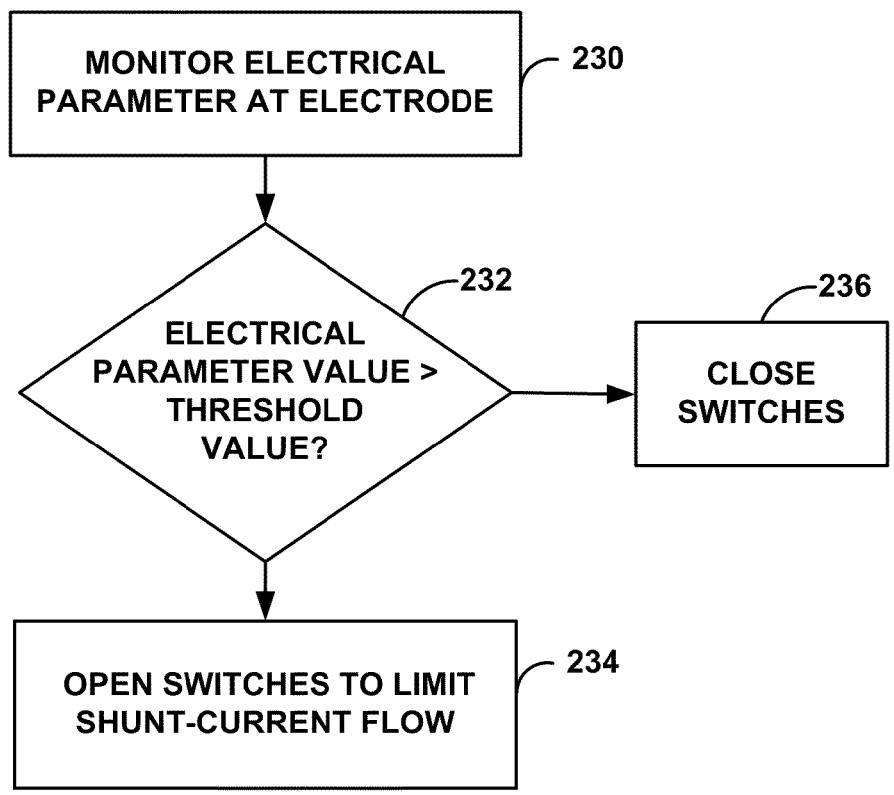
FIG. 22 is a flow diagram illustrating another example technique that may be implemented to reduce shunt-current that may flow through an electrical path connected to an IMD.

FIG. 22 is a flow diagram illustrating another example technique that INS 26 may implement in order to limit shunt-current. For purposes of illustration, reference will be made to shunt-current mitigation circuitry 210 illustrated in FIG. 19. In accordance with the technique shown in FIG. 21, monitor 212 monitors an electrical parameter value at one or more of electrodes 124. The electrical parameter value may be a voltage at each one of electrodes 124, a current through each one of electrodes 124, or a voltage across at least two of electrodes 124.

Processor 110 of INS 26 or a processor within monitor 212 may monitor an electrical parameter at one or more of electrodes 124 electrically connected to stimulation generator 114 of INS 26 (230), where the parameter may be either a current or voltage. Processor 110 or a processor within monitor 212 may determine whether the measured parameter value (e.g., current or voltage) is greater than or equal to a threshold value (232). The threshold value may, in some instances, be stored within memory 112, or may be stored within monitor 152 or a separate device. If the measured parameter value is greater than or equal to the threshold value, monitor 212 may control switches S10-S13 (FIG. 19) to toggle open to limit the current that feeds into INS 26 (234). If the measured parameter value is less than or equal to the threshold value, monitor 212 may control switches S10-S13 to toggle close (236).

The techniques described in this disclosure, including those attributed to ICD 16 (FIG. 1), INS 26 (FIG. 1), ICD 82 (FIG. 5), programmer 24 (FIG. 1), or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 90 of ICD 16, processor 110 of INS 26, and/or processor 130 of programmer 24, any one or more parts of the techniques described herein may be implemented by a processor of one of the devices 16, 26, programmer 24 or another computing device, alone or in combination with ICD 16, INS 26, or programmer 24.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described in the disclosure. These and other examples are within the scope of the following claims.

The invention claimed is:

1. A system comprising:
   a first implantable medical device (IMD) configured to deliver electrical stimulation to a first tissue site within a patient, wherein the first IMD comprises an outer housing that includes:
   an electrically conductive layer comprising an internal surface and an external surface; and
   an electrically insulative layer substantially fully covering at least one of the internal surface or the external surface of the electrically conductive layer, wherein the electrically insulative layer is configured to mitigate electrical shunt-current flowing through the outer housing of the first IMD; and
   a second IMD configured to deliver electrical stimulation to a second tissue site within the patient.

2. The system of claim 1, wherein the second implantable medical device (IMD) is configured to generate the electrical shunt-current, and wherein the electrically insulative layer is configured to mitigate the electrical shunt-current flowing from the second IMD to the first IMD through the outer housing of the first IMD.

3. The system of claim 1, wherein the electrically conductive layer comprises at least one of titanium or stainless steel.

4. The system of claim 1, wherein the electrically insulative layer comprises at least one of aluminum oxide, silicon dioxide, silicon nitride, aluminum nitride, titanium dioxide, or diamond.

5. The system of claim 1, wherein the electrically insulative layer comprises an electrically insulative polymer.

6. The system of claim 5, wherein the polymer comprises at least one of silicone, polycarbonate, or a biocompatible thermoplastic.

7. The system of claim 1, wherein the outer housing further comprises a third layer formed over the electrically insulative layer, the electrically insulative layer being positioned between the third layer and the electrically conductive layer.

8. The system of claim 7, wherein the third layer comprises metal.

9. The system of claim 7, wherein the electrically insulative layer comprises a first electrically insulative layer, and wherein the third layer comprises a second electrically insulative layer.

10. The system of claim 1, wherein the electrically insulative layer comprises a thickness of approximately 2.54 micrometers to approximately 1016 micrometers.

11. The system of claim 1, wherein the first tissue site comprises at least one of a nonmyocardial tissue site or a nonvascular cardiac tissue site.

12. The system of claim 1, wherein the first tissue site comprises at least one of an extravascular tissue site or a tissue site proximate to a nerve of the patient.

13. The system of claim 1, wherein the first implantable medical device (IMD) is electrically coupled to an electrode and comprises a processor enclosed within the outer housing and shunt-current mitigation circuitry coupled to the electrode, wherein the shunt-current mitigation circuitry is configured to reduce shunt-current that is introduced into the first IMD via the electrode, and wherein the shunt-current mitigation circuitry comprises a monitor electrically coupled to the electrode via a wire and a switch coupled to the monitor, wherein the monitor is configured to monitor an electrical parameter value at the electrode, and wherein the processor is configured to open the switch when the electrical parameter value is greater than or equal to a threshold value.

14. The system of claim 13, wherein the shunt-current mitigation circuitry further comprises at least one of a resistor or an inductor coupled to the switch.

15. The system of claim 13, wherein the second implantable medical device (IMD) is configured to transmit a communication signal to the processor that indicates prospective therapy delivery to the patient by the second IMD, and wherein the processor is configured to open the switch in response to receiving the communication signal from the second IMD.

16. The system of claim 13, wherein the electrode comprises a first electrode, and wherein the first implantable medical device is electrically coupled to a second electrode, and wherein the electrical parameter value comprises at least one of a voltage at the first electrode, a current through the first electrode or a voltage across at least the first and second electrodes.

17. The system of claim 1, wherein the second implantable medical device comprises an implantable cardiac device that is configured to deliver at least one of a pacing, cardioversion or defibrillation therapy to a heart of a patient.

18. The system of claim 1, wherein the first implantable medical device comprises at least one of an implantable electrical stimulator or an implantable neurostimulator.

19. The system of claim 1, wherein the first IMD is configured to communicate with the second IMD directly or via a programmer.

20. A system comprising:
a first implantable medical device (IMD) configured to deliver electrical stimulation to a first tissue site within a patient, wherein the first IMD comprises an outer housing that includes an electrically conductive portion;
an electrically insulative pouch physically separate from the first IMD and substantially fully encapsulating at least the electrically conductive portion of the outer housing, wherein the electrically insulative pouch is configured to reduce electrical shunt-current to the electrically conductive layer; and
a second IMD configured to deliver electrical stimulation to a second tissue site within the patient.

21. The system of claim 20, wherein the second implantable medical device (IMD) is configured to generate the electrical shunt-current, and wherein the electrically insulative pouch is configured to mitigate or substantially eliminate electrical shunt-current from flowing from the second IMD to the first IMD through the outer housing of the first IMD.

22. The system of claim 20, wherein the electrically insulative pouch comprises at least one of silicone, polycarbonate, or a biocompatible thermoplastic.

23. The system of claim 20, wherein the first IMD is configured to communicate with the second IMD directly or via a programmer.

24. A method of reducing electrical shunt-current between a first implantable medical device (IMD) configured to deliver electrical stimulation to a first tissue site within a patient and a second IMD configured to deliver electrical stimulation to a second tissue site within the patient, wherein the first IMD and second IMD are implanted within the patient, the method comprising substantially fully covering at least one of an internal surface or an external surface of an electrically conductive layer of an outer housing of the first IMD with at least one of an electrically insulative layer or an electrically insulative pouch, wherein the at least one of the electrically insulative layer or the electrically insulative pouch is configured to mitigate electrical shunt-current flowing to the electrically conductive layer.

25. The method of claim 24, wherein substantially fully covering at least one of an internal surface or an external surface of the electrically conductive layer of the outer housing of the first implantable medical device (IMD) with an electrically insulative layer comprises substantially fully covering at least one of an internal surface or an external surface of the electrically conductive layer of the outer housing of the first IMD with at least one of aluminum oxide, silicon dioxide, silicon nitride, aluminum nitride, titanium dioxide, or diamond.

26. The method of claim 24, wherein substantially fully covering at least one of an internal surface or an external surface of the electrically conductive layer of the outer housing of the first implantable medical device (IMD) with an electrically insulative layer comprises substantially fully covering at least one of an internal surface or an external surface of the electrically conductive layer of the outer housing of the first IMD with silicone.

27. The method of claim 24, wherein the first implantable medical device (IMD) comprises a processor enclosed within the outer housing, an electrode, and shunt-current mitigation circuitry coupled to the electrode, wherein the shunt-current mitigation circuitry is configured to reduce a shunt-current that is introduced into the first IMD via the electrode, wherein the shunt-current mitigation circuitry comprises a monitor electrically coupled to the electrode via a wire, wherein the monitor is configured to monitor an electrical parameter value at the electrode and a switch coupled to the monitor, and wherein the processor is configured to open the switch when the electrical parameter value is greater than or equal to a threshold value.

28. A method comprising:

implanting in a body of a patient a first implantable medical device (IMD) that delivers electrical stimulation to a first tissue site within the patient, wherein the first IMD comprises an outer housing that comprises an electrically conductive layer comprising an internal surface and an external surface and an electrically insulative layer substantially fully covering at least one of the internal surface or the external surface of the electrically conductive layer, wherein the electrically insulative layer is configured to reduce electrical shunt-current flowing through the outer housing of the first IMD; and implanting in the body of the patient a second IMD that delivers electrical stimulation to a second tissue site within the patient.

29. The method of claim 28, wherein the electrically insulative layer comprises at least one of aluminum oxide, silicon dioxide, silicon nitride, aluminum nitride, titanium dioxide, or diamond.

30. The method of claim 28, wherein the electrically insulative layer comprises at least one of silicone, polycarbonate, or a biocompatible thermoplastic.

31. A system comprising:

a first means for delivering electrical stimulation to a first tissue site within a patient, wherein the first means for delivering electrical stimulation comprises:

an outer housing means for housing components of the first IMD, wherein the outer housing means for housing components of the first IMD comprises:

a means for defining an internal surface and an external surface, wherein the means for defining is electrically conductive, and a means for electrically insulating the means for defining, wherein the means for electrically insulating substantially fully covers at least one of the internal surface or the external surface of the means for defining, and wherein the means for electrically insulating the means for defining is configured to mitigate electrical shunt-current flowing through the outer housing means of the first IMD; and a second means for delivering electrical stimulation to a second tissue site within the patient.

32. The system of claim 31, wherein the means for electrically insulating comprises at least one of silicone, polycarbonate, a biocompatible thermoplastic, aluminum oxide, silicon dioxide, silicon nitride, aluminum nitride, titanium dioxide, or diamond.

* * * * *